(12) United States Patent
Pennell et al.

(10) Patent No.: US 7,838,650 B2
(45) Date of Patent: Nov. 23, 2010

(54) PROMOTER, PROMOTER CONTROL ELEMENTS, AND COMBINATIONS, AND USES THEREOF

(75) Inventors: Roger Pennell, Malibu, CA (US); Kenneth A. Feldmann, Newbury Park, CA (US); Yu-Ping Lu, Camarillo, CA (US); Yiwen Fang, Los Angeles, CA (US); Shing Kwok, Woodland Hills, CA (US); Van-Dinh Dang, Oak Park, CA (US); Zhihong Cook, Woodland Hills, CA (US); Jack Okamuro, Oak Park, CA (US); Nestor Apuya, Culver City, CA (US); Richard Schneeberger, Carlsbad, CA (US); Emilio Margolles-Clark, Thousand Oaks, CA (US); Edward A. Kiegle, Chester, VT (US); Leonard Medrano, Azusa, CA (US)

(73) Assignee: Ceres, Inc., Thousand Oaks, CA (US)

( * ) Notice: Subject to any disclaimer, the term of this patent is extended or adjusted under 35 U.S.C. 154(b) by 626 days.

(21) Appl. No.: 11/602,163

(22) Filed: Nov. 20, 2006

(65) Prior Publication Data

US 2007/0226830 A1 Sep. 27, 2007

Related U.S. Application Data

(62) Division of application No. 11/172,703, filed on Jun. 30, 2005, now Pat. No. 7,214,789.

(60) Provisional application No. 60/583,691, filed on Jun. 30, 2004, provisional application No. 60/583,609, filed on Jun. 30, 2004.

(51) Int. Cl.
*C12N 15/82* (2006.01)
*C12N 15/63* (2006.01)
*C12N 15/11* (2006.01)
*A01H 5/00* (2006.01)

(52) U.S. Cl. ............... 536/24.1; 536/23.1; 800/278; 800/287; 435/320.1

(58) Field of Classification Search .............. None
See application file for complete search history.

(56) References Cited

U.S. PATENT DOCUMENTS 6,476,296 B1 * 11/2002 Fischer et al. ............ 800/290

FOREIGN PATENT DOCUMENTS

WO WO-02/06487 1/2002

OTHER PUBLICATIONS

Kim et al 1994, Plant Molecular Biology 24:105-117.*
Donald et al 1990, EMBO J. 9:1717-1726.*
Dolferus et al 1994, Plant Physiology 105:1075-1087.*
Lin et al 2000. Genbank Accession AC079733, submitted Sep. 8, 2000.*
Rognes, Sven Erik et al. "Transcriptional and biochemical regulation of a novel *Arabidopsis thaliana* bifunctional aspertate kinase-homoserine dehydrogenase gene isolated by functional complementation of a yeast hom5 mutant," Plant Molecular Biology, vol. 51, No. 2, Jan. 2003, pp. 281-294, XP002363935.
Kuusk, Sandra at al., "STY1 and STY2 promote the formation of apical tissues during *Arabidopsis* gynoecium development," Development (Cambridge), vol. 29, No. 20, Oct. 2002, pp. 4707-4717, XP002363936.
Jinn, Tsung-Luo et al., "Haesa, an *Arabidopsis* leucine-rich repeat receptor kinase, controls floral organ abscission," Genes and Development, vol. 14, No. 1, Jan. 1, 2000, pp. 108-117, XP002363937.
Hong, Seung-Beom et al., "Analysis of gene promoters for two tomato polygalacturonases epressed in abscission zones and the stigma," Plant Physiology (Rockville), vol. 123, No. 3, Jul. 2000, pp. 869-881, XP002363938.
Nazoa, Patricia et al., "Regulation of the nitrate transporter gene AtNRT2.1 in *Arabidopsis thaliana*: Responses to nitrate, amino acids and developmental stage," Plant Molecular Biology, vol. 52, No. 3, Jun. 2003, pp. 689-703, XP002363939.
Schuenmann, P H D et al., "Characterization of promoter expression patterns derived from the Pht1 phosphate transporter genes of barley (*Hordeum vulgare* L.)," Journal of Experimental Botany, vol. 55, No. 398, Apr. 2004, pp. 855-865, XP002363940.

* cited by examiner

*Primary Examiner*—Anne Marie Grunberg
*Assistant Examiner*—Brent Page
(74) *Attorney, Agent, or Firm*—Birch, Stewart, Kolasch, and Birch, LLP

(57) ABSTRACT

The present invention is directed to promoter sequences and promoter control elements, polynucleotide constructs comprising the promoters and control elements, and methods of identifying the promoters, control elements, or fragments thereof. The invention further relates to the use of the present promoters or promoter control elements to modulate transcript levels.

9 Claims, 1 Drawing Sheet

PROMOTER, PROMOTER CONTROL ELEMENTS, AND COMBINATIONS, AND USES THEREOF

Figure 1:
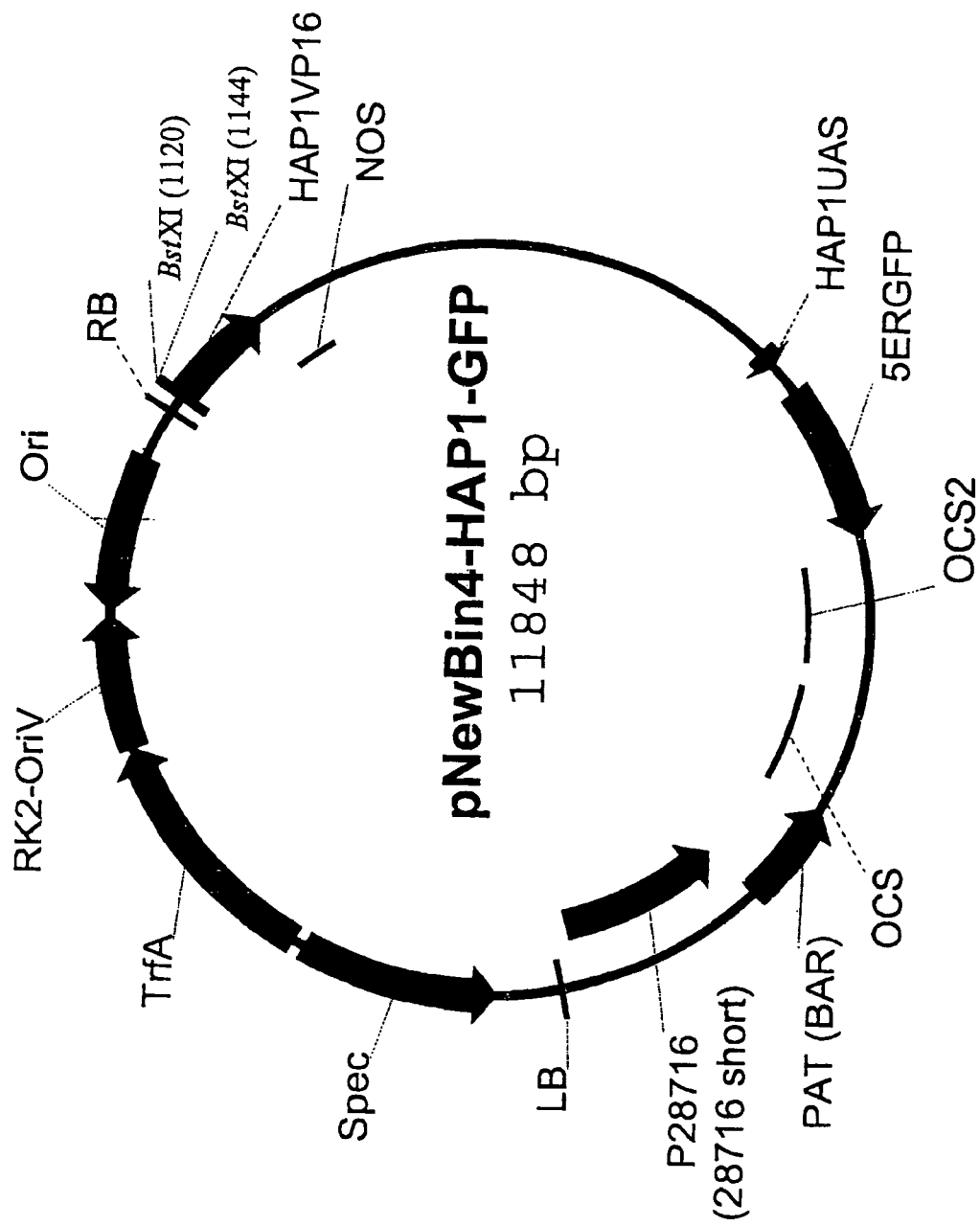

This Nonprovisional application claims priority under 35 U.S.C. §119(e) on U.S. application Ser. No: 11/172,703, filed on Jun. 30, 2005, which claims priority to Provisional Application No(s). 60/583,691 and 60/583,609 both filed on Jun. 30, 2004, the entire contents of which are hereby incorporated by reference.

FIELD OF THE INVENTION

The present invention relates to promoters and promoter control elements that are useful for modulating transcription of a desired polynucleotide. In order to modulate in vivo and in vitro transcription of a polynucleotide such promoters and promoter control elements can be included in polynucleotide constructs, expression cassettes, vectors or inserted into the chromosome or exist in the plant cell as an exogenous element. Host cells with polynucleotides comprising the promoters and promoter control elements of the present invention which have desired traits or characteristics resulting therefrom are also a part of the invention. This includes plant cells and plants regenerated therefrom.

BACKGROUND OF THE INVENTION

This invention relates to the field of biotechnology and in particular to specific promoter sequences and promoter control element sequences which are useful for the transcription of polynucleotides in a host cell or transformed host organism.

One of the primary goals of biotechnology is to obtain organisms such as plants, mammals, yeast and prokaryotes that have particular desired characteristics or traits. Examples of these characteristics or traits abound and in plants may include, for example, virus resistance, insect resistance, herbicide resistance, enhanced stability, enhanced biomass, enhanced yield or additional nutritional value.

Recent advances in genetic engineering have enabled researchers in the field to incorporate polynucleotide sequences into host cells to obtain the desired qualities in the organism of choice. This technology permits one or more polynucleotides from a source different than the organism of choice to be transcribed by the organism of choice. If desired, the transcription and/or translation of these new polynucleotides can be modulated in the organism to exhibit a desired characteristic or trait. Alternatively, new patterns of transcription and/or translation of polynucleotides endogenous to the organism can be produced. Both approaches can be used at the same time.

SUMMARY OF THE INVENTION

The present invention is directed to isolated polynucleotide sequences that comprise promoters and promoter control elements from plants, especially *Arabidopsis thaliana, Glycine max, Oryza sativa* and *Zea mays*, and other promoters and promoter control elements that function in plants.

It is an object of the present invention to provide isolated polynucleotides that are promoter sequences. These promoter sequences comprise, for example, (1) a polynucleotide having a nucleotide sequence as set forth in the Sequence Listing or a fragment thereof, (2) a polynucleotide having a nucleotide sequence having at least 80% sequence identity to a sequence as set in the Sequence Listing or a fragment thereof, and (3) a polynucleotide having a nucleotide sequence which hybridizes to a sequence as set forth in the Sequence Listing under a condition establishing a Tm-20° C.

It is another object of the present invention to provide isolated polynucleotides that are promoter control element sequences. These promoter control element sequences comprise, for example, (1) a polynucleotide having a nucleotide sequence as set forth in the Sequence Listing or a fragment thereof, (2) a polynucleotide having a nucleotide sequence having at least 80% sequence identity to a sequence as set forth in the Sequence Listing or a fragment thereof, and (3) a polynucleotide having a nucleotide sequence which hybridizes to a sequence as set forth in the Sequence Listing under a condition establishing a Tm-20° C.

Promoter or promoter control element sequences of the present invention are capable of modulating preferential transcription.

In another embodiment, the present promoter control elements are capable of serving as or fulfilling the function of, for example, a core promoter, a TATA box, a polymerase binding site, an initiator site, a transcription binding site, an enhancer, an inverted repeat, a locus control region, or a scaffold/matrix attachment region.

It is yet another object of the present invention to provide a polynucleotide that includes at least a first and a second promoter control element. The first promoter control element is a promoter control element sequence as discussed above and the second promoter control element is heterologous to the first control element. Moreover, the first and second control elements are operably linked. Such promoters may modulate transcript levels preferentially in a tissue or under particular conditions.

In another embodiment, the present isolated polynucleotide comprises a promoter or a promoter control element as described above, wherein the promoter or promoter control element is operably linked to a polynucleotide to be transcribed.

In another embodiment of the present vector, the promoter and promoter control elements of the instant invention are operably linked to a heterologous polynucleotide that is a regulatory sequence.

It is another object of the present invention to provide a host cell comprising an isolated polynucleotide or vector as described above or a fragment thereof. Host cells include, for instance, bacterial, yeast, insect cells, mammalian cells and plant cells. The host cell can comprise a promoter or promoter control element exogenous to the genome. Such a promoter can modulate transcription in cis- and in trans-orientation to the polynucletide.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free system of transcription or a host cell. This method comprises providing a polynucleotide or vector according to the present invention as described above and contacting the sample of the polynucleotide or vector with conditions that permit transcription.

In another embodiment of the present method, the polynucleotide or vector preferentially modulates
- (a) constitutive transcription,
- (b) stress induced transcription,
- (c) light or shade induced transcription,
- (d) dark induced transcription,
- (e) leaf transcription,
- (f) root transcription,
- (g) stem or shoot transcription,
- (h) silique or seed transcription,
- (i) callus transcription,
- (j) flower transcription,
- (k) immature bud and inflorescence-specific transcription, or
- (l) senescence induced transcription
- (m) germination transcription.

Other and further objects of the present invention will be made clear or become apparent from the following description.

BRIEF DESCRIPTION OF THE TABLES AND FIGURES

Table 1

Table 1 consists of the Expression Reports for each promoter of the invention and provides the nucleotide sequence for each promoter as well as details for GFP expression driven by each of the nucleic acid promoter sequences as observed in transgenic plants. The results are presented as summaries of the spatial expression, which provides information as to gross and/or specific expression in various plant organs and tissues. The observed expression pattern is also presented, which gives details of expression during different generations or different developmental stages within a generation. Additional information is provided regarding the associated gene, the GenBank reference, the source organism of the promoter and the vector and marker genes used for the construct. The following symbols are used consistently throughout the Table:

T1: First generation transformant

T2: Second generation transformant

T3: Third generation transformant (L): low expression level (M): medium expression level (H): high expression level Each row of the table begins with heading of the data to be found in the section. The following provides a description of the data to be found in each section:

| Heading in Table 1 | Description |
|---|---|
| Promoter Expression Report | Identifies the particular promoter report |
| Promoter tested in | Identifies the organism used for analysis |
| Spatial expression summary: | Identifies the organs and tissues where expression was observed and estimates the strength of expression |
| Observed expression pattern: | Presents expression pattern observed for various generations of plants and developmental stages |
| Expected expression pattern: | Identifies the pattern expected from other experiments |
| Selection Criteria: | Provides details on cloning the polynucleotide |

-continued

| Heading in Table 1 | Description |
|---|---|
| Gene: | Provides information concerning the gene modulated by the promoter |
| GenBank: | This field gives the Locus Number of the gene as well as the accession number. |
| Source Promoter Organism: | Identifies the organism from which the promoter was cloned. |
| Vector: | Identifies the vector into which the promoter was cloned. |
| Marker Type: | Identifies the type of marker linked to the promoter. The marker is used to determine patterns of gene expression in plant tissue. |
| Generation screened: T1 Mature T2 Seedling T2 Mature T3 Seedling | Identifies the plant generation(s) used in the screening process. T1 plants are those plants subjected to the transformation event while the T2 generation plants are from the seeds collected from the T1 plants and T3 plants are from the seeds of T2 plants. |
| Plant Expression | Identifies the generation and developmental stage of the plants analyzed |
| Events Screened Events Expressing | Provides the number of independent transformation events analyzed and the number which expressed the marker gene |
| GFP Expression Detected | This section lists the various organs analyzed and, where expression was observed, indicates the strength of the expression |
| X in the . . . | This field summarizes the expression pattern from digital images of the cells |
| Promoter Utility: | Identifies a specific function or functions that can be modulated using the promoter cDNA. |
| Trait-Subtrait Area: | Provides information as to what agronomic traits could be altered |
| Construct: | Provides the Ceres identifier number for the construct |
| Promoter Candidate I.D.: | Provides the Ceres identifier number for the promoter isolated |
| cDNA ID: | Provides the Ceres identifier number associated with the cDNA that corresponds to the endogenous cDNA sequence of the promoter. |
| T1 lines expressing (T2 seed): | Provides the identifier numbers for the events analyzed |
| Sequence | Provides the nucleotide sequence for the promoter described in the report |

Table 2

Table 2 provides a partial summary of the expression for some of the constructs of the invention.

FIG. 1

FIG. 1 is a schematic representation of the vector pNew-Bin4-HAP1-GFP. The definitions of the abbreviations used in the vector map are as follows:

Ori—the origin of replication used by an *E. coli* host

RB—sequence for the right border of the T-DNA from pMOG800

BstXI—restriction enzyme cleavage site used for cloning

HAP1VP16—coding sequence for a fusion protein of the HAP1 and VP16 activation domains NOS—terminator region from the nopaline synthase gene HAP1UAS—the upstream activating sequence for HAP1

5ERGFP—the green fluorescent protein gene that has been optimized for localization to the endoplasmic reticulum OCS2—the terminator sequence from the octopine synthase 2 gene OCS—the terminator sequence from the octopine synthase gene p28716 (a.k.a 28716 short)—promoter used to drive expression of the PAT (BAR) gene PAT (BAR)—a marker gene conferring herbicide resistance LB—sequence for the left border of the T-DNA from pMOG800

Spec—a marker gene conferring spectinomycin resistance

TrfA—transcription repression factor gene

RK2-OriV—origin of replication for *Agrobacterium*

DETAILED DESCRIPTION OF THE INVENTION

1. Definitions

Chimeric: The term "chimeric" is used to describe polynucleotides or genes, as defined supra, or constructs wherein at least two of the elements of the polynucleotide or gene or construct are heterologous to each other, such as the promoter and the polynucleotide to be transcribed and/or other regulatory sequences and/or filler sequences and/or complements thereof.

Constitutive Promoter: Promoters referred to herein as "constitutive promoters" actively promote transcription under most, but not necessarily all, environmental conditions and is essentially all cells in the vegetative stage and/or flowers and essentially all states of cell differentiation. Examples of constitutive promoters include the cauliflower mosaic virus (CaMV) 35S transcript initiation region and the 1' or 2' promoter derived from T-DNA of *Agrobacterium tumefaciens* as well as other transcription initiation regions from various plant genes known to those of skill in the art, such as the maize ubiquitin-1 promoter.

Core Promoter: This is the minimal stretch of contiguous DNA sequence that is sufficient to direct accurate initiation of transcription by the RNA polymerase II machinery (for review see: Struhl, 1987, *Cell* 49: 295-297; Smale, 1994, *In Transcription: Mechanisms and Regulation* (eds R. C. Conaway and J. W. Conaway), pp 63-81/Raven Press, Ltd., New York; Smale, 1997, *Biochim. Biophys. Acta* 1351: 73-88; Smale et al., 1998, *Cold Spring Harb. Symp. Quant. Biol.* 58: 21-31; Smale, 2001, *Genes & Dev.* 15: 2503-2508; Weis and Reinberg, 1992, *FASEB J.* 6: 3300-3309; Burke et al., 1998, *Cold Spring Harb. Symp. Quant. Biol* 63: 75-82). There are several sequence motifs, including the TATA box, initiator (Inr), TFIIB recognition element (BRE) and downstream core promoter element (DPE), that are commonly found in core promoters. Not all of these elements, however, occur in all promoters. That is, there are no universal core promoter elements (Butler and Kadonaga, 2002, *Genes & Dev.* 16: 2583-2592).

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of amino acid domains include, without limitation, AP2, helicase, homeobox, zinc finger, etc. Examples of nucleotide domains include, without limitation, TATA box, CAAT box, etc.

Endogenous: The term "endogenous" within the context of the current invention refers to any polynucleotide, polypeptide or protein sequence which is a natural part of a cell or organism regenerated from said cell. In the context of promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below and include *Agrobacterium*-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques and the like. Such a plant containing the exogenous nucleic acid is referred to here as a $T_0$ for the primary transgenic plant and $T_1$ for the first generation transformant. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function (see SCHEMATIC 1). Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other.

Homologous: In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

Inducible Promoter: An "inducible promoter" in the context of the current invention refers to a promoter the activity of which is influenced by certain conditions such as light, temperature, chemical concentration, protein concentration, conditions in an organism, cell, or organelle, etc. A typical example of an inducible promoter, which can be utilized with the polynucleotides of the present invention, is PARSK1, the promoter from an *Arabidopsis* gene encoding a serine-threonine kinase enzyme which is induced by dehydration, abscissic acid and sodium chloride (Wang and Goodman, Plant J. 8:37 (1995)). Examples of environmental conditions that may affect transcription by inducible promoters include anaerobic conditions, elevated temperature, the presence or absence of a nutrient or other chemical compound and/or the presence of light.

Modulate Transcription Level: As used herein, the phrase "modulate transcription" describes the biological activity of a promoter sequence or promoter control element. Such modulation includes, without limitation, up- and down-regulation of initiation of transcription, rate of transcription and/or transcription levels.

Mutant: In the current invention "mutant" refers to a heritable change in a mutation sequence at a specific location. Mutant genes of the current invention may or may not have an associated identifiable phenotype.

Operable Linkage: An "operable linkage" is a linkage in which a promoter sequence or promoter control element is connected to a polynucleotide sequence(s) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoded by the polynucleotide and if the nature of the linkage between the two DNA sequences does not (1) result in the introduction of a frame-shift mutation, (2) interfere with the ability of the promoter sequence to direct the expression of the protein, antisense RNA or ribozyme or (3) interfere with the ability of the DNA template to be transcribed. Thus, a promoter sequence would be operably linked to a polynucleotide sequence if the promoter was capable of effecting transcription of that polynucleotide sequence.

Optional Promoter Fragments: The phrase "optional promoter fragments" is used to refer to any sub-sequence of the promoter that is not required for driving transcription of an operationally linked coding region. These fragments comprise the 5' UTR and any exon(s) of the endogenous coding region. The optional promoter fragments may also comprise any exon(s) and the 3' or 5' UTR of the gene residing upstream of the promoter (that is, 5' to the promoter). Optional promoter fragments also include any intervening sequences that are introns or sequence that occurs between exons or an exon and the UTR.

Orthologous: "Orthologous" is a term used herein to describe a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultrastructure of a cell). Generally it is believed that orthologous structures share a common evolutionary origin.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad Sci.* (*USA*) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid sequences were searched against subject nucleic acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill in the art.

Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, immediately upstream to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible via the worldwide web). The database at the NCBI FTP site uses "gi" numbers assigned by NCBI as a unique identifier for each sequence in the database, thereby providing a non-redundant database for sequence from various databases, including GenBank, EMBL, DBBJ, (DNA Database of Japan) and PDB (Brookhaven Protein Data Bank).

Regulatory Sequence: The term "regulatory sequence," as used in the current invention, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

Related Sequences: "Related sequences" refer to either a polypeptide or a nucleotide sequence that exhibits some degree of sequence similarity with a reference sequence.

Specific Promoters: In the context of the current invention, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present invention, are: PTA29, a promoter which is capable of driving gene transcription specifically in tapetum and only during anther development (Koltonow et al., Plant Cell 2:1201 (1990); RCc2 and RCc3, promoters that direct root-specific gene transcription in rice (Xu et al., Plant Mol. Biol. 27:237 (1995); and TobRB27, a root-specific promoter from tobacco (Yamamoto et al., Plant Cell 3:371 (1991)). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription".

Stringency: "Stringency" as used herein is a function of probe length, probe composition (G+C content) and salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% \ G+C)-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log \{[Na^+]/(1+0.7[Na^+])\}+0.41(\% \ G+C)-500/L0.63(\% \ formamide) \quad (2)$$

where L is the length of the probe in the hybrid (P. Tijessen, "Hybridization with Nucleic Acid Probes" in *Laboratory Techniques in Biochemistry and Molecular Biology*, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al. (1973) J. Mol. Biol. 81:123), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene can be substantially free of other plant genes. Other examples include, but are not limited to, ligands substantially free of receptors (and vice versa), a growth factor substantially free of other growth factors and a transcription binding factor substantially free of nucleic acids.

Suppressor: See "Enhancer/Suppressor"

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present invention, a "translational start site" is usually an ATG or AUG in a transcript, often the first ATG or AUG. A single protein encoding transcript, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc). Likewise, polynucleotide variants can consist of changes that add or delete a specific UTR or exon sequence. It will be understood that there may be sequence variations within sequence or fragments used or disclosed in this application. Preferably, variants will be such that the sequences have at least 80%, preferably at least 90%, 95, 97, 98, or 99% sequence identity. Variants preferably measure the primary biological function of the native polypeptide or protein or polynucleotide.

2. Introduction

The polynucleotides of the invention comprise promoters and promoter control elements that are capable of modulating transcription.

Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:

(a) antisense;

(b) ribozymes;

(c) coding sequences; or (d) fragments thereof.

The promoter also can modulate transcription in a host genome in cis- or in trans-.

In an organism such as a plant, the promoters and promoter control elements of the instant invention are useful to produce preferential transcription which results in a desired pattern of transcript levels in particular cells, tissues or organs or under particular conditions.

3. Table of Contents

The following description of the present invention is outlined in the following table of contents.

A. Identifying and Isolating Promoter Sequences of the Invention (1) Cloning Methods (2) Chemical Synthesis B. Isolating Related Promoter Sequences (1) Relatives Based on Nucleotide Sequence Identity (2) Relatives Based on Coding Sequence Identity (3) Relatives Based on Common Function C. Identifying Control Elements
(1) Types of Transcription Control Elements
(2) Those Described by the Examples
(3) Those Identifiable by Bioinformatics
(4) Those Identifiable by In Vitro and In Vivo Assays
(5) Non-Natural Control Elements
D. Constructing Promoters and Control Elements
(1) Combining Promoters and Promoter Control Elements
(2) Number of Promoter Control Elements
(3) Spacing Between Control Elements
E. Vectors
(1) Modification of Transcription by Promoters and Promoter Control Elements
(2) Polynucleotide to be Transcribed
(3) Other Regulatory Elements
(4) Other Components of Vectors
F. Insertion of Polynucleotides and Vectors Into a Host Cell
(1) Autonomous of the Host Genome
(2) Integrated into the Host Genome
G. Utility A. Identifying and Isolating Promoter Sequences of the Invention The promoters and promoter control elements of the present invention are presented in the Sequence Listing and were identified from *Arabidopsis thaliana* or *Oryza sativa*. Additional promoter sequences encompassed by the invention can be identified as described below.

(1) Cloning Methods

Isolation from genomic libraries of polynucleotides comprising the sequences of the promoters and promoter control elements of the present invention is possible using known techniques.

For example, polymerase chain reaction (PCR) can amplify the desired polynucleotides utilizing primers designed from sequences in the row titled "Sequences". Polynucleotide libraries comprising genomic sequences can be constructed according to Sambrook et al., *Molecular Cloning: A Laboratory Manual*, 2$^{nd}$ Ed. (1989) Cold Spring Harbor Press, Cold Spring Harbor, N.Y.), for example.

Other procedures for isolating polynucleotides comprising the promoter sequences of the invention include, without limitation, tail-PCR and 5' rapid amplification of cDNA ends (RACE). For tail-PCR see, for example, Liu et al. (1995) Plant J 8(3): 457-463; Liu et al. (1995) Genomics 25: 674-681; Liu et al. (1993) Nucl. Acids Res. 21(14): 3333-3334; and Zoe et al. (1999) BioTechniques 27(2): 240-248; for RACE see, for example, *PCR Protocols: A Guide to Methods and Applications*, (1990) Academic Press, Inc.

(2) Chemical Synthesis

In addition, the promoters and promoter control elements described in the Sequence Listing can be chemically synthesized according to techniques in common use. See, for example, Beaucage et al. (1981) Tet. Lett. 22: 1859 and U.S. Pat. No. 4,668,777.

Such chemical oligonucleotide synthesis can be carried out using commercially available devices, such as Biosearch 4600 or 8600 DNA synthesizer by Applied Biosystems, a division of Perkin-Elmer Corp. (Foster City, Calif., USA) and Expedite by Perceptive Biosystems (Framingham, Mass., USA).

Synthetic RNA, including natural and/or analog building blocks, can be synthesized on the Biosearch 8600 machines (see above).

Oligonucleotides can be synthesized and then ligated together to construct the desired polynucleotide.

B. Isolating Related Promoter Sequences

Included in the present invention are promoter and promoter control elements that are related to those described in the Sequence Listing. Such related sequences can be isolated using
(a) nucleotide sequence identity,
(b) coding sequence identity or
(c) common function or gene products.

Relatives can include both naturally occurring promoters and non-natural promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

According to current knowledge, promoter sequences and promoter control elements exist as functionally important regions, such as protein binding sites and spacer regions. These spacer regions are apparently required for proper positioning of the protein binding sites. Thus, nucleotide substitutions, insertions and deletions can be tolerated in the spacer regions to a certain degree without loss of function.

In contrast, less variation is permissible in the functionally important regions since changes in the sequence can interfere with protein binding. Nonetheless, some variation in the functionally important regions is permissible so long as function is conserved.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Relatives Based on Nucleotide Sequence Identity

Included in the present invention are promoters exhibiting nucleotide sequence identity to those described in the Sequence Listing.

DEFINITION

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in the Sequence Listing. Such sequence identity can be calculated by the algorithms and computers programs described above.

Usually, such sequence identity is exhibited in an alignment region that is at least 75% of the length of a sequence shown in the Sequence Listing or corresponding full-length sequence; more usually at least 80%; more usually, at least 85%, more usually at least 90%, and most usually at least 95%, yet even more usually, at least 96%, 97%, 98% or 99% of the length of a sequence shown in the Sequence Listing.

The percentage of the alignment length is calculated by counting the number of bases of the sequence in the region of strongest alignment, e.g. a continuous region of the sequence that contains the greatest number of bases that are identical to the bases between two sequences that are being aligned. The number of bases in the region of strongest alignment is divided by the total base length of a sequence in the Sequence Listing.

These related promoters generally exhibit similar preferential transcription as those promoters described in the Sequence Listing and as described in the "observed expression pattern" and "expected expression pattern" fields of the reports of Table 1.

Construction of Polynucleotides

Naturally occurring promoters that exhibit nucleotide sequence identity to those shown in the Sequence Listing can be isolated using the techniques as described above. More specifically, such related promoters can be identified, for example, with typical hybridization procedures such as Southern blots or probing of polynucleotide libraries using varying stringencies (see above).

Non-natural promoter variants of those shown in the Sequence Listing can be constructed using cloning methods that incorporate the desired nucleotide variation. For example see Ho et al. (1989) Gene 77:51-59, which describes a site directed mutagenesis procedure using PCR.

Any related promoter showing sequence identity to those shown in the Sequence Listing can be chemically synthesized as described above.

Also, the present invention includes non-natural promoters that exhibit the above-sequence identity to those in the Sequence Listing.

The promoters and promoter control elements of the present invention may also be synthesized with 5' or 3' extensions to facilitate additional manipulation, for instance.

Testing of Polynucleotides

Polynucleotides of the invention were tested for activity by cloning the sequence into an appropriate vector, transforming plants with the construct and assaying for marker gene expression. Recombinant DNA constructs were prepared which comprise the polynucleotide sequences of the invention inserted into a vector suitable for transformation of plant cells. The construct can be made using standard recombinant DNA techniques (Sambrook et al. 1989) and can be introduced to the species of interest by Agrobacterium-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) Proc. Natl. Acad. Sci. USA 89: 8794-8797; Hamilton et al. (1996) Proc. Natl. Acad. Sci. USA 93: 9975-9979;

(b) YAC: Burke et al. (1987) Science 236:806-812;

(c) PAC: Sternberg N. et al. (1990) Proc Natl Acad Sci U S A. 87(1):103-7;

(d) Bacteria-Yeast Shuttle Vectors: Bradshaw et al. (1995) Nucl Acids Res 23: 4850-4856;

(e) Lambda Phage Vectors: Replacement Vector, e.g., Frischauf et al. (1983) J. Mol Biol 170: 827-842; or Insertion vector, e.g., Huynh et al., In: Glover NM (ed) DNA Cloning: A practical Approach, Vol. 1 Oxford: IRL Press (1985); T-DNA gene fusion vectors: Walden et al. (1990) Mol Cell Biol 1: 175-194; and (g) Plasmid vectors: Sambrook et al., infra.

Typically, the construct comprises a vector containing a sequence of the present invention operationally linked to any marker gene. The polynucleotide was identified as a promoter by the expression of the marker gene. Although many marker genes can be used, Green Fluroescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin or herbicide resistance, such as resistance to chlorosulfuron or phosphinotricin. Vectors can also include origins of replication, scaffold attachment regions (SARs), markers, homologous sequences, introns, etc.

Promoter Control Elements of the Invention

The promoter control elements of the present invention include those that comprise a sequence shown in the Sequence Listing or fragments thereof. The size of the fragments can range from 5 bases to 10 kilobases (kb). Typically, the fragment size is no smaller than 8 bases; more typically, no smaller than 12; more typically, no smaller than 15 bases; more typically, no smaller than 20 bases; more typically, no smaller than 25 bases; even more typically, no more than 30, 35, 40 or 50 bases.

Usually, the fragment size is no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Relatives Based on Nucleotide Sequence Identity

Included in the present invention are promoter control elements exhibiting nucleotide sequence identity to those described in the Sequence Listing or fragments thereof.

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in the Sequence Listing. Such sequence identity can be calculated by the algorithms and computers programs described above.

Promoter Control Element Configuration

A common configuration of the promoter control elements in RNA polymerase II promoters is described in "Models for prediction and recognition of eukaryotic promoters", T. Werner (1999) Mammalian Genome 10, 168-175.

Promoters are generally modular in nature. Promoters can consist of a basal promoter which functions as a site for assembly of a transcription complex comprising an RNA polymerase, for example RNA polymerase II. A typical transcription complex will include additional factors such as $TF_{II}B$, $TF_{II}D$ and $TF_{II}E$. Of these, $TF_{II}D$ appears to be the only one to bind DNA directly. The promoter might also contain one or more promoter control elements such as the elements discussed above. These additional control elements may function as binding sites for additional transcription factors that have the function of modulating the level of transcription with respect to tissue specificity, of transcriptional responses to particular environmental or nutritional factors and the like.

One type of promoter control element is a polynucleotide sequence representing a binding site for proteins. Typically, within a particular functional module, protein binding sites constitute regions of 5 to 60, preferably 10 to 30, more preferably 10 to 20 nucleotides. Within such binding sites, there are typically 2 to 6 nucleotides which specifically contact amino acids of the nucleic acid binding protein.

The protein binding sites are usually separated from each other by 10 to several hundred nucleotides, typically by 15 to 150 nucleotides, often by 20 to 50 nucleotides.

Further, protein binding sites in promoter control elements often display dyad symmetry in their sequence. Such elements can bind several different proteins and/or a plurality of sites can bind the same protein. Both types of elements may be combined in a region of 50 to 1,000 base pairs.

Binding sites for any specific factor have been known to occur almost anywhere in a promoter. For example, functional AP-1 binding sites can be located far upstream, as in the rat bone sialoprotein gene where an AP-1 site located about 900 nucleotides upstream of the transcription start site suppresses expression (Yamauchi et al. (1996) Matrix Biol. 15, 119-130). Alternatively, an AP-1 site located close to the transcription start site plays an important role in the expression of Moloney murine leukemia virus (Sap et al. (1989) Nature 340, 242-244.

(2) Those Identifiable by Bioinformatics

Promoter control elements from the promoters of the instant invention can be identified utilizing bioinformatic or computer driven techniques.

One method uses a computer program AlignACE to identify regulatory motifs in genes that exhibit common preferential transcription across a number of time points. The program identifies common sequence motifs in such genes. See, Roth et al. (1998) Nature Biotechnol. 16: 949-945; Tavazoie et al. (1999) Nat Genet Jul.; 22 (3):281-5;

Genomatix also makes available a GEMS Launcher program and other programs to identify promoter control elements and configuration of such elements. Genomatix is located in Munich, Germany.

Other references also describe detection of promoter modules by models independent of overall nucleotide sequence similarity. See, for instance, Klingenhoff et al. (1999) Bioinformatics 15: 180-186.

Protein binding sites of promoters can be identified as reported in "Computer-assisted prediction, classification, and delimitation of protein binding sites in nucleic acids", Frech et al. (1993) Nucleic Acids Research 21(7): 1655-1664.

Other programs used to identify protein binding sites include, for example, Signal Scan (Prestridge et al. (1996) Comput. Appl. Biosci. 12: 157-160); Matrix Search (Chen et al. (1995) Comput. Appl. Biosci. 11: 563-566), available as part of Signal Scan 4.0; MatInspector (Ghosh et al. (1993) Nucl. Acid Res. 21: 3117-3118) available via the internet; ConsInspector (Frech et al. (1993) Nucl. Acids Res. 21: 1655-1664), available via the internet; TFSearch and TESS.

Frech et al. (1997) "Software for the analysis of DNA sequence elements of transcription", Bioinformatics & Sequence Analysis, Vol. 13, no. 1, 89-97 is a review of different software for analysis of promoter control elements. This paper also reports the usefulness of matrix-based approaches to yield more specific results.

For other procedures, see Fickett et al. (2000) Curr. Op. Biotechnol. 11: 19-24 and Quandt et al. (1995) Nucleic Acids Res. 23: 4878-4884.

(3) Those Identifiable by In-Vitro and In-Vivo Assays

Promoter control elements can also be identified with in-vitro assays such as transcription detection methods and with in-vivo assays such as enhancer trapping protocols.

In-Vitro Assays

Examples of in-vitro assays include detection of binding of protein factors that bind promoter control elements. Fragments of the instant promoters can be used to identify the location of promoter control elements. Another option for obtaining a promoter control element with desired properties is to modify known promoter sequences. This is based on the fact that the function of a promoter is dependent on the interplay of regulatory proteins that bind to specific, discrete nucleotide sequences ("motifs") in the promoter. Such interplay subsequently affects the general transcription machinery and regulates transcription efficiency. These regulatory proteins are positive regulators or negative regulators (repressors) and one protein can have a dual role depending on the context (Johnson and McKnight, (1989) Annu. Rev. Biochem. 58:799-839).

One type of in-vitro assay uses a known DNA binding factor to isolate DNA fragments that bind. If a fragment or promoter variant does not bind, then a promoter control element has been removed or disrupted. For specific assays, see, for instance, Luo et al. (1997) J. Mol. Biol. 266:470, Chusacultanachai et al. (1999) J. Biol. Chem. 274:23591, Fabbro et al. (1995) Biochem. Biophys. Res. Comm 213:781).

Alternatively, a DNA fragment suspected of conferring a particular pattern of expression can be examined for the ability to bind transcription factors responsible for generating the particular pattern using methods such as DNA footprinting (e.g. Cousins et al. (2000) Immunology 99:101 and V. Kolla et al. (1999) Biochem. Biophys. Res. Comm 266:5) or "mobility-shift" assays (Fabiani et al. (2000) J. Biochem 347:147 and Sugiura et al. (2000) J. Biochem 347:155) or fluorescence polarization (e.g. Royer et al. U.S. Pat. No. 5,445,935). Both mobility shift and DNA footprinting assays can also be used to identify portions of large DNA fragments that are bound by proteins in unpurified transcription extracts prepared from tissues or organs of interest.

Cell-free transcription extracts can be prepared and used to directly assay in a reconstitutable system (Narayan et al. (2000) Biochemistry 39:818).

In-Vivo Assays

Promoter control elements can be identified with reporter genes in in-vivo assays with the use of fragments of the instant promoter, polynucleotides or variants thereof. That is, a fragment(s) comprising a basal or "core" promoter operably linked to a reporter sequence can be inserted into a vector. When transcribed, a detectable label is produced. Examples of reporter genes include those encoding luciferase, green fluorescent protein, GUS, neo, cat and bar. Alternatively, the transcribed reporter sequence can be detected with AFLP and microarray techniques.

In promoter probe vector systems, genomic DNA fragments are inserted upstream of the coding sequence of a reporter gene which is expressed only when the cloned fragment contains DNA having transcription modulation activity (Neve et al. (1979) Nature 277:324-325). No transcription occurs when control elements are present in the fragment or when control elements present are disrupted. Probe vectors have been designed for assaying transcription modulation in E. coli (An et al. (1979) J. Bact. 140:400-407) and other bacterial hosts (Band et al. (1983) Gene 26:313-315 and Achen (1986) Gene 45:45-49), yeast (Goodey et al. (1986) Mol. Gen. Genet. 204:505-511) and mammalian cells (Pater et al. (1984) J. Mol. App. Gen. 2:363-371).

A different design of a promoter/control element trap includes packaging into retroviruses for more efficient delivery into cells. One type of retroviral enhancer trap was described by von Melchner et al. (Genes Dev. (1992); U.S. Pat. No. 5,364,783). The basic design of this vector includes a reporter protein coding sequence engineered into the U3 portion of the 3' LTR. No splice acceptor consensus sequences are included, limiting its utility to work as an enhancer trap only. A different approach to a gene trap using retroviral vectors was pursued by Friedrich and Soriano (Genes Dev. 1991) who engineered a lacZ-neo fusion protein linked to a splicing acceptor. LacZ-neo fusion protein expression from trapped loci allows not only for drug selection, but also for visualization of β-galatactosidase expression using the chromogenic substrate, X-gal.

A general review of tools for identifying transcriptional regulatory regions of genomic DNA is provided by J. W. Fickett et al. (Curr. Opn. Biotechnol (2000) 11:19).

(4) Non-Natural Control Elements

Non-natural control elements can be constructed by inserting, deleting or substituting nucleotides into the promoter control elements described above. Such control elements are capable of transcription modulation that can be determined using any of the assays described above.

C. Constructing Promoters with Control Elements (1) Combining Promoters and Promoter Control Elements The promoter polynucleotides and promoter control elements of the present invention, both naturally occurring and synthetic, can be combined with each other to produce the desired preferential transcription. In addition, the polynucleotides of the invention can be combined with other known sequences to generate promoters useful for modulating, for example, tissue-specific transcription or condition-specific transcription. Such preferential transcription can be determined using the techniques or assays described above.

The relatives, fragments and variants as well as full-length sequences shown in the Sequence Listing are useful alone or in combination.

The location and relation of promoter control elements within a promoter can affect the ability of the promoter to modulate transcription. The order and spacing of control elements is a factor when constructing promoters.

(2) Number of Promoter Control Elements

Promoters can contain any number of control elements. For example, a promoter can contain multiple transcription binding sites or other control elements. One element may confer tissue or organ specificity, another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

(3) Spacing Between Control Elements

Spacing between control elements or the configuration or control elements can be determined or optimized to permit the desired polynucleotide or protein-polynucleotide interactions to occur.

For example, if two transcription factors bind to a promoter simultaneously or relatively close in time, the binding sites are spaced to allow each factor to bind without steric hinderance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to form a hairpin or loop so as to permit the two elements to bind. The spacing between two such hybridizing control elements can be as small as a t-RNA loop, to as large as 10 kb.

Typically, the spacing is no smaller than 5 bases, more typically no smaller than 8, more typically no smaller than 15 bases, more typically no smaller than 20 bases, more typically no smaller than 25 bases, even more typically no more than 30, 35, 40 or 50 bases.

Usually, the fragment size in no larger than 5 kb bases, more usually no larger than 2 kb, more usually no larger than 1 kb, more usually no larger than 800 bases, more usually no larger than 500 bases, even more usually no more than 250, 200, 150 or 100 bases.

Such spacing between promoter control elements can be determined using the techniques and assays described above.

(4) Other Promoters

The following are promoters that are induced under stress conditions and can be combined with those of the present invention: 1dh1 (oxygen stress, tomato see Germain and Ricard (1997) Plant Mol Biol 35:949-54), GPx and CAT (oxygen stress, mouse, see Franco et al. (1999) Free Radic Biol Med 27:1122-32), ci7 (cold stress, potato, see Kirch et al. (1997) Plant Mol Biol. 33:897-909), Bz2 (heavy metals, maize, see Marrs and Walbot (1997) Plant Physiol 113:93-102), HSP32 (hyperthermia, rat, see Raju and Maines (1994) Biochim Biophys Acta 1217:273-80); MAPKAPK-2 (heat shock, *Drosophila*, see Larochelle and Suter (1995) Gene 163:209-14).

In addition, the following promoters are examples those induced by the presence or absence of light and can be used in combination with those of the present invention: Topoisomerase II (pea, see Reddy et al. (1999) Plant Mol Biol 41:125-37), chalcone synthase (soybean, see Wingender et al. (1989) Mol Gen Genet 218:315-22), mdm2 gene (human tumor, see Saucedo et al. (1998) Cell Growth Differ 9:119-30), Clock and BMAL1 (rat, see Namihira et al. (1999) Neurosci Lett 271:1-4), PHYA (Arabidopsis, see Canton and Quail 1999 Plant Physiol 121:1207-16), PRB-1b (tobacco, see Sessa et al. (1995) Plant Mol Biol 28:537-47) and Ypr10 (common bean, see Walter et al. (1996) Eur J Biochem 239: 281-93).

The promoters and control elements of the following genes can be used in combination with the present invention to confer tissue specificity: for roots MipB (iceplant, Yamada et al. (1995) Plant Cell 7:1129-42) and SUCS (root nodules, broadbean, Kuster et al. (1993) Mol Plant Microbe Interact 6:507-14), for leaves OsSUT1 (rice, Hirose et al. (1997) Plant Cell Physiol 38:1389-96), for siliques Msg (soybean, Stomvik et al. (1999) Plant Mol Biol 41:217-31) and for inflorescence (*Arabidopsis*, Shani et al. (1997) Plant Mol Biol 34(6): 837-42) and ACT11 (*Arabidopsis*, Huang et al. (1997) Plant Mol Biol 33:125-39).

Still other promoters are affected by hormones or participate in specific physiological processes, which can be used in combination with those of present invention. Some examples are the ACC synthase gene that is induced differently by ethylene and brassinosteroids (mung bean, Yi et al. (1999) Plant Mol Biol 41:443-54), the TAPG1 gene that is active during abscission (tomato, Kalaitzis et al. (1995) Plant Mol Biol 28:647-56) and the 1-aminocyclopropane-1-carboxylate synthase gene (carnation, Jones et al. (1995) Plant Mol Biol 28:505-12) and the CP-2/cathepsin L gene (rat, Kim and Wright (1997) Biol Reprod 57:1467-77), which are both active during senescence.

E. Vectors

Vectors are a useful component of the present invention. In particular, vectors can deliver the present promoters and/or promoter control elements to a cell. For the purposes of this invention, such delivery ranges from randomly introducing the promoter or promoter control element alone into a cell to integrating the vector containing the promoter or promoter control element into a cell's genome. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are preferred vectors for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al. (1985) Nature 317: 741-744; Gordon-Kamm et al. (1990) Plant Cell 2: 603-618; and Stalker et al. (1988) Science 242: 419-423). Other marker genes exist which provide hormone responsiveness.

(1) Modification of Transcription by Promoters and Promoter Control Elements

The promoter or promoter control element of the present invention may be operably linked to a polynucleotide to be transcribed. In this manner, the promoter or promoter control element modifys transcription by modulating transcript levels of that polynucleotide when inserted into a genome.

The promoter or promoter control element need not be linked, operably or otherwise, to a polynucleotide to be transcribed before being inserted into a genome. For example, the promoter or promoter control element can be inserted into the genome in front of a polynucleotide already present therein. Here, the promoter or promoter control element modulates the transcription of a polynucleotide that was already present in the genome. This polynucleotide may be native to the genome or inserted at an earlier time.

Alternatively, the promoter or promoter control element can simply be inserted into a genome or maintained extrachromosomally as a way to divert the transcription resources of the system to itself. See, for example, Vaucheret et al. (1998) Plant J 16: 651-659. This approach may be used to downregulate the transcript levels of a group of polynucleotide(s).

(2) Polynucleotide to be Transcribed

The nature of the polynucleotide to be transcribed is not limited. Specifically, the polynucleotide may include sequences that will have activity as RNA as well as sequences that result in a polypeptide product. These sequences may include, but are not limited to antisense sequences, ribozyme sequences, spliceosomes, amino acid coding sequences and fragments thereof.

Specific coding sequences may include, but are not limited to endogenous proteins or fragments thereof, or heterologous proteins including marker genes or fragments thereof.

Promoters and control elements of the present invention are useful for modulating metabolic or catabolic processes. Such processes include, but are not limited to secondary product metabolism, amino acid synthesis, seed protein storage, oil development, pest defense and nitrogen usage. Some examples of genes, transcripts, peptides or polypeptides participating in these processes which can be modulated by the present invention: are tryptophan decarboxylase (tdc), strictosidine synthase (str1), dihydrodipicolinate synthase (DH-DPS), aspartate kinase (AK), 2S albumin, alpha-, beta-, and gamma-zeins, ricinoleate, 3-ketoacyl-ACP synthase (KAS), Bacillus thuringiensis (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon that encodes the first methionine. Thus, when constructing a recombinant polynucleotide for expressing a protein product according to the present invention, it is preferable to ensure that no intervening codons encoding a methionine are contained within the linkage between the polynucleotide to be transcribed, or a functional derivative thereof, and the 3' portion of the promoter, preferably including the TATA box.

The vector of the present invention may contain additional components. For example, an origin of replication that allows for replication of the vector in a host cell may be added. In addition, homologous sequences flanking a target location in the genome may be added to allow for site-specific recombination of a specific sequence contained in the vector. T-DNA sequences also allow for insertion of a specific sequence randomly into a target genome, but in a random manner.

The vector may also contain a plurality of restriction sites for insertion of the promoter and/or promoter control elements of the present invention as well as any polynucleotide to be transcribed. The vector can additionally contain selectable marker genes. The vector can also contain a transcriptional and translational initiation region and/or a transcriptional and translational termination region that functions in the host cell. The termination region may be native with the transcriptional initiation region, may be native with the polynucleotide to be transcribed or may be derived from another source. Convenient termination regions are available from the Ti-plasmid of *A. tumefaciens*, such as the octopine synthase and nopaline synthase termination regions. See also, Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; Joshi et al. (1987) Nucleic Acid Res. 15:9627-9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436, 391 and Murray et al. (1989) Nucleic Acids Res. 17:477-498.

Additional sequence modifications include elimination of sequences encoding spurious polyadenylation signals, exon intron splice site signals, transposon-like repeats and other such sequences well characterized as deleterious to expression. The G-C content of the polynucleotide may be adjusted to the average levels for a given cellular host, as calculated by reference to known genes expressed in the host cell. The polynucleotide sequence may be modified to avoid hairpin secondary mRNA structures.

A general description of expression vectors and reporter genes can be found in Gruber et al., "Vectors for Plant Transformation", in Methods in Plant Molecular Biology & Biotechnology (1993) Glich et al. eds., pp. 89-119, CRC Press). Moreover GUS expression vectors and GUS gene cassettes are available from Clonetech Laboratories, Inc. (Palo Alto, Calif.) while luciferase expression vectors and luciferase gene cassettes are available from Promega Corp. (Madison, Wis.). GFP vectors are available from Aurora Biosciences.

F. Polynucleotide Insertion Into A Host Cell

The polynucleotides according to the present invention can be inserted into a host cell. A host cell includes but is not limited to a plant, mammalian, insect, yeast and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

(1) Polynucleotides Autonomous of the Host Genome

The polynucleotides of the present invention can exist autonomously or independent of the host cell genome. Vectors of these types are known in the art and include, for example, certain types of non-integrating viral vectors, autonomously replicating plasmids, artificial chromosomes and the like.

Additionally, in some cases transient expression of a polynucleotide may be desired.

(2) Polynucleotides Integrated into the Host Genome

The promoter sequences, promoter control elements or vectors of the present invention can be transformed into host cells. These transformations can be into protoplasts or isolated cells or intact tissues. Preferably, expression vectors are introduced into intact tissue. General methods of culturing plant tissues are provided for example by Maki et al. ("Procedures for Introducing Foreign DNA into Plants" in Methods in Plant Molecular Biology & Biotechnology (1993) Glich et al. eds., pp. 67-88 CRC Press) and by Phillips et al. "Cell-Tissue Culture and In-Vitro Manipulation" in Corn & Corn Improvement, 3rd Edition 10Sprague et al. (1998) eds. pp. 345-387) American Society of Agronomy Inc. et al.

Methods of introducing polynucleotides into plant tissue include the direct infection or co-cultivation of a plant cell with *Agrobacterium tumefaciens* (Horsch et al. (1985) Science 227:1229). Descriptions of *Agrobacterium* vector systems and methods for *Agrobacterium*-mediated gene transfer are provided by Gruber et al. supra.

Alternatively, polynucleotides are introduced into plant cells or other plant tissues using a direct gene transfer method such as microprojectile-mediated delivery, DNA injection, electroporation and the like. More preferably, polynucleotides are introduced into plant tissues using the microprojectile media delivery with the biolistic device. See, for example, Tomes et al., "Direct DNA transfer into intact plant cells via microprojectile bombardment" In: Plant Cell, Tissue and Organ Culture: Fundamental Methods (1995) Gamborg and Phillips eds. Springer Verlag, Berlin.

In another embodiment of the current invention, expression constructs can be used for gene expression in callus culture for the purpose of expressing marker genes encoding peptides or polypeptides that allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media. Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP) and β-glucuronidase (GUS), etc. Some of the promoters in the Seqeunce Listing will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art such as by homologous sequences or T-DNA discussed above or by using the cre-lox system (Vergunst et al. (1998) Plant Mol. Biol. 38:393).

G. Utility

Common Uses

In yet another embodiment, the promoters of the present invention can be used to further understand developmental mechanisms. For example, promoters that are specifically induced during callus formation, somatic embryo formation, shoot formation or root formation can be used to explore the effects of overexpression, repression or ectopic expression of target genes, or for isolation of trans-acting factors.

The vectors of the invention can be used not only for expression of coding regions but may also be used in exon-trap cloning, or promoter trap procedures to detect differential gene expression in various tissues. See Lindsey et al (1993) "Tagging Genomic Sequences That Direct Transgene Expression by Activation of a Promoter Trap in Plants," Transgenic Research 2:3347 and Auch et al. "Exon Trap Cloning: Using PCR to Rapidly Detect and Clone Exons from Genomic DNA Fragments," Nucleic Acids Research, 18:674.

Entrapment vectors, first described for use in bacteria (Casadaban and Cohen (1979) Proc. Nat. Aca. Sci. U.S.A. 76: 4530 and Casadaban et al. (1980) J. Bacteriol. 143: 971) permit selection of insertional events that lie within coding sequences. Entrapment vectors can be introduced into pluripotent ES cells in culture and then passed into the germline via chimeras (Gossler et al. (1989) Science 244: 463 and Skarnes (1990) Biotechnology 8: 827). Promoter or gene trap vectors often contain a reporter gene, e.g. lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene that is coupled to a reporter gene. The DNA constructs are inserted into a bacterial strain otherwise lacking the metabolic gene and the resulting bacteria are used to infect the host organism. Only bacteria expressing the metabolic gene survive in the host organism. Consequently, inactive constructs can be eliminated by harvesting only bacteria that survive for some minimum period in the host. At the same time, constitutively active constructs can be eliminated by selecting only bacteria that do not express the reporter gene under laboratory conditions. The bacteria selected by such a method contain constructs that are selectively induced only during infection of the host. The IVET approach can be modified in plants to identify genes induced in either the bacteria or the plant cells upon pathogen infection or root colonization. For information on IVET see the following articles: Mahan et al. (1993) Science 259:686-688, Mahan et al. (1995) PNAS USA 92:669-673, Heithoff et al. (1997) PNAS USA 94:934-939, and Wang et al. (1996) PNAS USA. 93:10434.

Constitutive Transcription

Promoters and control elements providing constitutive transcription are desired for modulation of transcription in most cells of an organism under most environmental conditions. In a plant, for example, constitutive transcription is useful for modulating genes involved in defense, pest resistance, herbicide resistance, etc.

Constitutive up-regulation and down-regulation of transcription are useful for these applications. For instance, genes, transcripts and/or polypeptides that increase defense, pest and herbicide resistance may require constitutive up-regulation of transcription. In contrast, constitutive down-regulation of transcriptional may be desired to inhibit those genes, transcripts, and/or polypeptides that lower defense, pest and herbicide resistance.

Typically, promoter or control elements that provide constitutive transcription produce transcription levels that are statistically similar in many tissues and environmental conditions observed.

Calculation of P-value from the different observed transcript levels is one means of determining whether a promoter or control element is providing constitutive up-regulation. P-value is the probability that the difference of transcript levels is not statistically significant. The higher the P-value, the more likely the difference of transcript levels is not significant. One formula used to calculate P-value is as follows:

$$\int \varphi(x)dx \text{ integrated from } a \text{ to } \infty,$$

where $\varphi(x)$ is a normal distribution, where $a = \dfrac{|Sx - \mu|}{\sigma \text{ (all Samples except } Sx\text{)}};$ where $Sx$ = the intensity of the sample of interest where $\mu$ = is the average of the intensities of all samples sample except $Sx$, $$= \dfrac{\left(\sum S1 \ldots Sn\right) - Sx}{n - 1}$$

where $\sigma(S1 \ldots S11$, not including $Sx)$ = the standard deviation of all sample intensities except $Sx$ The P-value from the formula ranges from 1.0 to 0.0.

Usually, each P-value of the transcript levels produced by the promoter or control element and observed in a majority of cells, tissues or organs under various environmental conditions is greater than $10^{-8}$; more usually, greater than $10^{-7}$; even more usually, greater than $10^{-6}$; even more usually, greater than $10^{-5}$ or $10^{-4}$.

For up-regulation of transcription, promoter and control elements produce transcript levels that are above background of the assay.

Stress Induced Preferential Transcription

Promoters and control elements providing modulation of transcription under oxidative, drought, oxygen, wound and methyl jasmonate stress are particularly useful for producing host cells or organisms that are more resistant to biotic and abiotic stresses. For example, in a plant modulation of genes, transcripts and/or polypeptides in response to oxidative stress can protect cells against damage caused by oxidative agents such as hydrogen peroxide and other free radicals.

Drought induction of genes, transcripts and/or polypeptides are useful to increase the viability of a plant, for example when water is a limiting factor. In contrast, genes, transcripts and/or polypeptides induced during oxygen stress can help the flood tolerance of a plant.

The promoters and control elements of the present invention can modulate the plant's response to stresses. Examples of some genes involved in stress condition responses are VuPLD1 (drought stress, Cowpea; Pham-Thi et al. (1999) Plant Mol. Biol 1257-65), pyruvate decarboxylase (oxygen stress, rice; Rivosal et al. (1997) Plant Physiol. 114(3): 1021-29), and the chromoplast specific carotenoid gene (oxidative stress, Capsicum; see Bouvier et al. (1998) J Biol Chem 273: 30651-59).

Promoters and control elements providing preferential transcription during wounding or that are induced by methyl jasmonate can produce a defense response in host cells or organisms. In a plan, preferential modulation of genes, transcripts and/or polypeptides under such conditions is useful to induce a defense response to mechanical wounding, pest or pathogen attack or treatment with certain chemicals.

Promoters and control elements of the present invention also can trigger a response similar to those described for cf9 (viral pathogen, tomato; O'Donnell et al. (1998) Plant J 14(1): 137-42), hepatocyte growth factor activator inhibitor type 1 (HAI-1), which enhances tissue regeneration (tissue injury, human; Koono et al. (1999) J Histochem Cytochem 47: 673-82), copper amine oxidase (CuAO) induced during ontogenesis and wound healing (wounding, chick-pea; Rea et al. (1998) FEBS Letters 437: 177-82), proteinase inhibitor II (wounding, potato; Pena-Cortes et al. (1988) Planta 174: 84-89), protease inhibitor II (methyl jasmonate, tomato; Farmer and Ryan (1990) Proc Natl Acad Sci USA 87: 7713-7716) and two vegetative storage protein genes VspA and VspB (wounding, jasmonic acid and water deficit; soybean; Mason and Mullet (1990) Plant Cell 2: 569-579).

Up-regulation and down-regulation of transcription are useful for these applications. For instance, genes, transcripts and/or polypeptides that increase oxidative, flood or drought tolerance may require up-regulation of transcription. In contrast, transcriptional down-regulation may be desired to inhibit those genes, transcripts and/or polypeptides that lower such tolerance.

Typically, promoter or control elements which provide preferential transcription in wounding or under methyl jasmonate induction produce transcript levels that are statistically significantly altered as compared to cell types, organs or tissues under other conditions.

For preferential up-regulation of transcription, promoter and control elements produce transcript levels that are above background of the assay.

Light Induced Preferential Transcription

Promoters and control elements providing preferential transcription when induced by light exposure can be utilized to modulate growth, metabolism and development to increase drought tolerance and to decrease damage from light stress for host cells or organisms. In a plant, modulation of genes, transcripts and/or polypeptides in response to light is useful (1) to increase the photosynthetic rate;

(2) to increase storage of certain molecules in leaves or green parts only, e.g. silage with high protein or starch content;

(3) to modulate production of exogenous compositions in green tissue, e.g. certain feed enzymes;

(4) to induce growth or development, such as fruit development and maturity, during extended exposure to light;

(5) to modulate guard cells to control the size of stomata in leaves to prevent water loss, or (6) to induce accumulation of beta-carotene to help plants cope with light induced stress.

The promoters and control elements of the present invention can also trigger responses similar to those described for: abscisic acid insensitive3 (ABI3) (dark-grown *Arabidopsis* seedlings, Rohde et al. (2000) Plant Cell 12: 35-52), asparagine synthetase (pea root nodules, Tsai, Coruzzi, (1990) EMBO J 9: 323-32) and mdm2 gene (human tumor; Saucedo et al. (1998) Cell Growth Differ 9: 119-30).

Up-regulation and down-regulation of transcription are useful for these applications. For instance, genes, transcripts and/or polypeptides that increase drought or light tolerance may require up-regulation of transcription. In contrast, transcriptional down-regulation may be desired to inhibit those genes, transcripts and/or polypeptides that lower such tolerance.

Typically, promoter or control elements which provide preferential transcription in cells, tissues or organs exposed to light produce transcript levels that are statistically significantly altered as compared to cells, tissues or organs under decreased light exposure (intensity or length of time).

For preferential up-regulation of transcription, promoter and control elements produce transcript levels that are above background of the assay.

Dark Induced Preferential Transcription

Promoters and control elements providing preferential transcription when induced by dark or decreased light intensity or decreased light exposure time can be utilized to time growth, metabolism and development and to modulate photosynthesis capabilities for host cells or organisms. In a plant, modulation of genes, transcripts and/or polypeptides in response to dark is useful (1) to induce growth or development, such as fruit development and maturity, despite lack of light;

(2) to modulate genes, transcripts and/or polypeptide active at night or on cloudy days; or (3) to preserve the plastid ultra structure present at the onset of darkness.

The present promoters and control elements can also trigger response similar to those described in the section above.

Up-regulation and down-regulation of transcription are useful for these applications. For instance, genes, transcripts and/or polypeptides that increase growth and development may require up-regulation of transcription. In contrast, transcriptional down-regulation may be desired to inhibit those genes, transcripts and/or polypeptides that modulate photosynthesis capabilities.

Typically, promoter or control elements which provide preferential transcription under exposure to dark or decreased light intensity or decreased exposure time produce transcript levels that are statistically significantly altered.

For preferential up-regulation of transcription, promoter and control elements produce transcript levels that are above background of the assay.

Leaf Preferential Transcription

Promoters and control elements providing preferential transcription in a leaf can modulate growth, metabolism and development or modulate energy and nutrient utilization in host cells or organisms. In a plant, preferential modulation of genes, transcripts and/or polypeptide in a leaf is useful (1) to modulate leaf size, shape, and development;

(2) to modulate the number of leaves; or (3) to modulate energy or nutrient usage in relation to other organs and tissues.

Up-regulation and down-regulation of transcription are useful for these applications. For instance, genes, transcripts and/or polypeptides that increase growth may require up-regulation of transcription. In contrast, transcriptional down-regulation may be desired to inhibit energy usage in a leaf and to redirect it to the fruit instead, for instance.

Typically, promoter or control elements which provide preferential transcription in the cells, tissues, or organs of a leaf produce transcript levels that are statistically significantly altered as compared to other cells, organs or tissues.

For preferential up-regulation of transcription, promoter and control elements produce transcript levels that are above background of the assay.

Root Preferential Transcription

Promoters and control elements providing preferential transcription in a root can modulate growth, metabolism, development, nutrient uptake, nitrogen fixation or modulate energy and nutrient utilization in host cells or organisms. In a plant, for example, preferential modulation of genes, transcripts, and/or in a leaf, is useful (1) to modulate root size, shape, and development;

(2) to modulate the number of roots, or root hairs;

(3) to modulate mineral, fertilizer, or water uptake;

(4) to modulate transport of nutrients; or (4) to modulate energy or nutrient usage in relation to other organs and tissues.

Up-regulation and down-regulation of transcription are useful for these applications. For instance, genes, transcripts and/or polypeptides that increase growth may require up-regulation of transcription. In contrast, transcriptional down-regulation may be desired to inhibit nutrient usage in a root and to redirect it to the leaf instead, for instance.

Typically, promoter or control elements which provide preferential transcription in cells, tissues or organs of a root produce transcript levels that are statistically significantly altered as compared to other cells, organs or tissues.

For preferential up-regulation of transcription, promoter and control elements produce transcript levels that are above background of the assay.

Stem/Shoot Preferential Transcription

Promoters and control elements providing preferential transcription in a stem or shoot can modulate growth, metabolism and development or modulate energy and nutrient utilization in host cells or organisms. In a plant, preferential modulation of genes, transcripts and/or a polypeptide in a stem or shoot is useful (1) to modulate stem/shoot size, shape, and development; or (2) to modulate energy or nutrient usage in relation to other organs and tissues Up-regulation and down-regulation of transcription are useful for these applications. For instance, genes, transcripts and/or polypeptides that increase growth may require up-regulation of transcription. In contrast, transcriptional down-regulation may be desired to inhibit energy usage in a stem/shoot and to redirect it to the fruit instead, for instance.

Typically, promoter or control elements which provide preferential transcription in the cells, tissues or organs of a stem or shoot produce transcript levels that are statistically significant as compared to other cells, organs or tissues.

For preferential up-regulation of transcription, promoter and control elements produce transcript levels that are above background of the assay.

Fruit and Seed Preferential Transcription

Promoters and control elements providing preferential transcription in a silique or fruit can time growth, development, or maturity; or modulate fertility; or modulate energy and nutrient utilization in host cells or organisms. In a plant preferential modulation of genes, transcripts and/or polypeptides in a fruit is useful (1) to modulate fruit size, shape, development, and maturity;
(2) to modulate the number of fruit or seeds;
(3) to modulate seed shattering;
(4) to modulate components of seeds, such as, storage molecules, starch, protein, oil, vitamins, anti-nutritional components, such as phytic acid;
(5) to modulate seed and/or seedling vigor or viability;
(6) to incorporate exogenous compositions into a seed, such as lysine rich proteins;
(7) to permit similar fruit maturity timing for early and late blooming flowers; or
(8) to modulate energy or nutrient usage in relation to other organs and tissues.

Up-regulation and down-regulation of transcription are useful for these applications. For instance, genes, transcripts, and/or polypeptides that increase growth may require up-regulation of transcription. In contrast, transcriptional down-regulation may be desired to inhibit late fruit maturity, for instance.

Typically, promoter or control elements which provide preferential transcription in the cells, tissues or organs of siliques or fruits produce transcript levels that are statistically significantly altered as compared to other cells, organs or tissues.

For preferential up-regulation of transcription, promoter and control elements produce transcript levels that are above background of the assay.

Callus Preferential Transcription

Promoters and control elements providing preferential transcription in a callus can be useful to modulating transcription in dedifferentiated host cells. In a plant transformation, for example, preferential modulation of genes or transcript in callus is useful to modulate transcription of a marker gene, which can facilitate selection of cells that are transformed with exogenous polynucleotides.

Up-regulation and down-regulation of transcription are useful for these applications. For instance, genes, transcripts and/or polypeptides that increase marker gene detectability-may require up-regulation of transcription. In contrast, transcriptional down-regulation may be desired to increase the ability of the calluses to differentiate, for instance.

Typically, promoter or control elements which provide preferential transcription in callus produce transcript levels that are statistically significantly altered as compared to other cell types, tissues, or organs. Calculation of P-value from the different observed transcript levels is one means of determining whether a promoter or control element is providing such preferential transcription.

Usually, each P-value of the transcript levels observed in callus as compared to at least one other cell type, tissue or organ, is less than $10^4$; more usually, less than $10^{-5}$; even more usually, less than $10^{-6}$; even more usually, less than $10^{-7}$ or $10^{-8}$.

For preferential up-regulation of transcription, promoter and control elements produce transcript levels that are above background of the assay.

Flower Specific Transcription

Promoters and control elements providing preferential transcription in flowers can modulate pigmentation or modulate fertility in host cells or organisms. In a plant, preferential modulation of genes, transcripts and/or polypeptides in a flower is useful, (1) to modulate petal color; or
(2) to modulate the fertility of pistil and/or stamen.

Up-regulation and down-regulation of transcription are useful for these applications. For instance, genes, transcripts and/or polypeptides that increase pigmentation may require up-regulation of transcription. In contrast, transcriptional down-regulation may be desired to inhibit fertility, for instance.

Typically, promoter or control elements which provide preferential transcription in flowers produce transcript levels that are statistically significantly altered as compared to other cells, organs or tissues.

For preferential up-regulation of transcription, promoter and control elements produce transcript levels that are above background of the assay.

Immature Bud and Inflorescence Preferential Transcription

Promoters and control elements providing preferential transcription in an immature bud or inflorescence can time growth, development or maturity or modulate fertility or viability in host cells or organisms. In a plant, preferential modulation of genes, transcripts, and/or polypeptide in an immature bud or inflorescence is useful, (1) to modulate embryo development, size, and maturity;
(2) to modulate endosperm development, size, and composition;
(3) to modulate the number of seeds and fruits; or
(4) to modulate seed development and viability.

Up-regulation and down-regulation of transcription is useful for these applications. For instance, genes, transcripts and/or polypeptides that increase growth may require up-regulation of transcription. In contrast, transcriptional down-regulation may be desired to decrease endosperm size, for instance.

Typically, promoter or control elements which provide preferential transcription in immature buds and inflorescences produce transcript levels that are statistically significantly altered as compared to other cell types, organs or tissues.

For preferential up-regulation of transcription, promoter and control elements produce transcript levels that are above background of the assay.

Senescence Preferential Transcription

Promoters and control elements providing preferential transcription during senescence can be used to modulate cell degeneration, nutrient mobilization and scavenging of free radicals in host cells or organisms. Other types of responses that can be modulated include, for example, senescence associated genes (SAG) that encode enzymes thought to be involved in cell degeneration and nutrient mobilization (*Arabidopsis*; Hensel et al. (1993) Plant Cell 5: 553-64), and the CP-2/cathepsin L gene (rat; Kim and Wright (1997) Biol Reprod 57: 1467-77). Both of these genes are induced during senescence.

In a plant, preferential modulation of genes, transcripts and/or polypeptides during senescencing is useful to modulate fruit ripening.

Up-regulation and down-regulation of transcription are useful for these applications. For instance, genes, transcripts and/or polypeptides that increase scavenging of free radicals may require up-regulation of transcription. In contrast, transcriptional down-regulation may be desired to inhibit cell degeneration, for instance.

Typically, promoter or control elements which provide preferential transcription in cells, tissues or organs during senescence produce transcript levels that are statistically significantly altered as compared to other conditions.

For preferential up-regulation of transcription, promoter and control elements produce transcript levels that are above background of the assay.

Germination Preferential Transcription

Promoters and control elements providing preferential transcription in a germinating seed can time growth, development or maturity or modulate viability in host cells or organisms. In a plant, preferential modulation of genes, transcripts and/or polypeptide in a germinating seed is useful (1) to modulate the emergence of they hypocotyls, cotyledons and radical; or (2) to modulate shoot and primary root growth and development;

Up-regulation and down-regulation of transcription is useful for these applications. For instance, genes, transcripts and/or polypeptides that increase growth may require up-regulation of transcription. In contrast, transcriptional down-regulation may be desired to decrease endosperm size, for instance.

Typically, promoter or control elements which provide preferential transcription in a germinating seed produce transcript levels that are statistically significantly altered as compared to other cell types, organs or tissues.

For preferential up-regulation of transcription, promoter and control elements produce transcript levels that are above background of the assay.

Results

GFP Experimental Procedures and Results

The polynucleotide sequences of the present invention were tested for promoter activity using Green Fluorescent Protein (GFP) assays in the following manner.

Approximately 1-2 kb of genomic sequence occurring immediately upstream of the ATG translational start site of the gene of interest was isolated using appropriate primers tailed with BstXI restriction sites. Standard PCR reactions using these primers and genomic DNA were conducted. The resulting product was isolated, cleaved with BstXI and cloned into the BstXI site of an appropriate vector, such as pNew-Bin4-HAP1-GFP (see FIG. 1).

Transformation

The following procedure was used for transformation of plants

1. Stratification of WS-2 Seed.

Add 0.5 ml WS-2 (CS2360) seed to 50 ml of 0.2% Phytagar in a 50 ml Corning tube and vortex until seeds and Phytagar form a homogenous mixture.

Cover tube with foil and stratify at 4° C. for 3 days.

2. Preparation of Seed Mixture.

Obtain stratified seed from cooler.

Add seed mixture to a 1000 ml beaker.

Add an additional 950 ml of 0.2% Phytagar and mix to homogenize.

3. Preparation of Soil Mixture.

Mix 24 L SunshineMix #5 soil with 16 L Therm-O-Rock vermiculite in cement mixer to make a 60:40 soil mixture.

Amend soil mixture by adding 2 Tbsp Marathon and 3 Tbsp Osmocote and mix contents thoroughly.

Add 1 Tbsp Peters fertilizer to 3 gallons of water and add to soil mixture and mix thoroughly.

Fill 4-inch pots with soil mixture and round the surface to create a slight dome.

Cover pots with 8-inch squares of nylon netting and fasten using rubber bands.

Place 14 4-inch pots into each no-hole utility flat.

4. Planting.

Using a 60 ml syringe, aspirate 35 ml of the seed mixture.

Exude 25 drops of the seed mixture onto each pot.

Repeat until all pots have been seeded.

Place flats on greenhouse bench, cover flat with clear propagation domes, place 55% shade cloth on top of flats and subirrigate by adding 1 inch of water to bottom of each flat.

5. Plant Maintenance.

3 to 4 days after planting, remove clear lids and shade cloth.

Subirrigate flats with water as needed.

After 7-10 days, thin pots to 20 plants per pot using forceps.

After 2 weeks, subirrigate all plants with Peters fertilizer at a rate of 1 Tsp per gallon water.

When bolts are about 5-10 cm long, clip them between the first node and the base of stem to induce secondary bolts.

6 to 7 days after clipping, perform dipping infiltration.

6. Preparation of *Agrobacterium*.

Add 150 ml fresh YEB to 250 ml centrifuge bottles and cap each with a foam plug (Identi-Plug).

Autoclave for 40 min at 121° C.

After cooling to room temperature, uncap and add 0.1 ml each of carbenicillin, spectinomycin and rifampicin stock solutions to each culture vessel.

Obtain *Agrobacterium* starter block (96-well block with *Agrobacterium* cultures grown to an $OD_{600}$ of approximately 1.0) and inoculate one culture vessel per construct by transferring 1 ml from appropriate well in the starter block.

Cap culture vessels and place on Lab-Line incubator shaker set at 27° C. and 250 RPM.

Remove after *Agrobacterium* cultures reach an $OD_{600}$ of approximately 1.0 (about 24 hours), cap culture vessels with plastic caps, place in Sorvall SLA 1500 rotor and centrifuge at 8000 RPM for 8 min at 4° C.

Pour out supernatant and put bottles on ice until ready to use.

Add 200 ml Infiltration Media (IM) to each bottle, resuspend *Agrobacterium* pellets and store on ice.

7. Dipping Infiltration.

Pour resuspended *Agrobacterium* into 16 oz polypropylene containers.

Invert 4-inch pots and submerge the aerial portion of the plants into the *Agrobacterium* suspension and let stand for 5 min.

Pour out *Agrobacterium* suspension into waste bucket while keeping polypropylene container in place and return the plants to the upright position.

Place 10 covered pots per flat.

Fill each flat with 1-inch of water and cover with shade cloth.

Keep covered for 24 hr and then remove shade cloth and polypropylene containers.

Resume normal plant maintenance.

When plants have finished flowering cover each pot with a ciber plant sleeve.

After plants are completely dry, collect seed and place into 2.0 ml micro tubes and store in 100-place cryogenic boxes.

Recipes:

0.2% Phytagar 2 g Phytagar

1 L nanopure water

Shake until Phytagar suspended

Autoclave 20 min

YEB (for 1 L)
- 5 g extract of meat
- 5 g Bacto peptone
- 1 g yeast extract
- 5 g sucrose
- 0.24 g magnesium sulfate
- While stirring, add ingredients, in order, to 900 ml nanopure water
- When dissolved, adjust pH to 7.2
- Fill to 1 L with nanopure water
- Autoclave 35 min Infiltration Medium (IM) (for 1 L)
- 2.2 g MS salts
- 50 g sucrose
- 5 ul BAP solution (stock is 2 mg/ml)
- While stirring, add ingredients in order listed to 900 ml nanopure water
- When dissolved, adjust pH to 5.8.
- Volume up to 1 L with nanopure water.
- Add 0.02% Silwet L-77 just prior to resuspending *Agrobacterium*

High Throughput Screening—T1 Generation

1. Soil Preparation. Wear gloves at all times.

In a large container, mix 60% autoclaved SunshineMix #5 with 40% vermiculite.

Add 2.5 Tbsp of Osmocote, and 2.5 Tbsp of 1% granular Marathon per 25 L of soil.

Mix thoroughly.

2. Fill Com-Packs With Soil.

Loosely fill D601 Com-Packs level to the rim with the prepared soil.

Place filled pot into utility flat with holes, within a no-hole utility flat.

Repeat as necessary for planting. One flat set should contain 6 pots.

3. Saturate Soil.

Evenly water all pots until the soil is saturated and water is collecting in the bottom of the flats.

After the soil is completely saturated, dump out the excess water.

4. Plant the Seed.

5. Stratify the Seeds.

After sowing the seed for all the flats, place them into a dark 4° C. cooler.

Keep the flats in the cooler for 2 nights for WS seed. Other ecotypes may take longer. This cold treatment will help promote uniform germination of the seed.

6. Remove Flats From Cooler and Cover With Shade Cloth. (Shade cloth is only needed in the greenhouse)

After the appropriate time, remove the flats from the cooler and place onto growth racks or benches.

Cover the entire set of flats with 55% shade cloth. The cloth is necessary to cut down the light intensity during the delicate germination period.

The cloth and domes should remain on the flats until the cotyledons have fully expanded. This usually takes about 4-5 days under standard greenhouse conditions.

7. Remove 55% Shade Cloth and Propagation Domes.

After the cotyledons have fully expanded, remove both the 55% shade cloth and propagation domes.

8. Spray Plants With Finale Mixture. Wear gloves and protective clothing at all times.

Prepare working Finale mixture by mixing 3 ml concentrated Finale in 48 oz of water in the Poly-TEK sprayer.

Completely and evenly spray plants with a fine mist of the Finale mixture.

Repeat Finale spraying every 3-4 days until only transformants remain. (Approximately 3 applications are necessary.)

When satisfied that only transformants remain, discontinue Finale spraying.

9. Weed Out Excess Transformants.

Weed out excess transformants such that a maximum number of five plants per pot exist evenly spaced throughout the pot.

GFP Assay

Tissues are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

| | |
|---|---|
| Flower | Pedice, l receptacle, nectary, sepal, petal, filament, anther, pollen, carpel, style, papillae, vascular, epidermis, stomata, trichome |
| Silique | Stigma, style, carpel, septum, placentae, transmitting tissue, vascular, epidermis, stomata, abscission zone, ovule |
| Ovule | Pre-fertilization: inner integument, outer integument, embryo sac, funiculus, chalaza, micropyle, gametophyte<br>Post-fertilization: zygote, inner integument, outer integument, seed coat, primordial, chalaza, micropyle, early endosperm, mature endosperm, embryo |
| Embryo | Suspensor, preglobular, globular, heart, torpedo, late, mature, provascular, hypophysis, radicle, cotyledons, hypocotyl |
| Stem | epidermis, cortex, vascular, xylem, phloem, pith, stomata, trichome |
| Leaf | Petiole, mesophyll, vascular, epidermis, trichome, primordial, stomata, stipule, margin |

T1 Mature: These are the T1 plants resulting from independent transformation events. These are screened between stage 6.50-6.90 (means the plant is flowering and that 50-90% of the flowers that the plant will make have developed) which is 4-6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal micsrocopy.

T2 Seedling: Progeny are collected from the T1 plants giving the same expression pattern and the progeny (T2) are sterilized and plated on agar-solidified medium containing M&S salts. In the event that there was no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings were screened until two seedlings were observed to have the same pattern. Generally found the same expression pattern was found in the first two seedlings. However, up to 6 seedlings were screened before "no expression pattern" was recorded. All constructs are screened as T2 seedlings even if they did not have an expression pattern in the T1 generation.

T2 Mature: The T2 mature plants were screened in a similar manner to the T1 plants. The T2 seeds were planted in the greenhouse, exposed to selection and at least one plant screened to confirm the T1 expression pattern. In instances where there were any subtle changes in expression, multiple plants were examined and the changes noted in the tables.

T3 Seedling: This was done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Instrumentation:

Microscope
Inverted Leica DM IRB
Fluorescence filter blocks:
Blue excitation BP 450-490; long pass emission LP 515.
Green excitation BP 515-560; long pass emission LP 590

Objectives
HCPL FLUOTAR 5X/0.5
HCPL APO 10X/0.4 IMM water/glycerol/oil
HCPL APO 20X/0.7 IMM water/glycerol/oil
HCXL APO 63X/1.2 IMM water/glycerol/oil Leica TCS SP2 Confocal Scanner
Spectral range of detector optics 400-850 nm.
Variable computer controlled pinhole diameter.
Optical zoom 1-32X.
Four simultaneous detectors:
Three channels for collection of fluorescence or reflected light.
One channel for transmitted light detector.
Laser sources:
Blue Ar 458/5 mW, 476 nm/5 mW, 488 nm/20 mW, 514 nm/20 mW.
Green HeNe 543 nm/1.2 mW
Red HeNe 633 nm/10 mW Results The section in Table 1 entitled "The spatial expression of the promoter-marker-vector" presents the results of the GFP assays as reported by their corresponding cDNA ID number, construct number and line number. Unlike the microarray results, which measure the difference in expression of the endogenous cDNA under various conditions, the GFP data gives the location of expression that is visible under the imaging parameters. Table 3 summarizes the results of the spatial expression results for each promoter.

Explanation of Table 1

Table 1 includes various information about each promoter or promoter control element of the invention including the nucleotide sequence, the spatial expression pattern associated with each promoter and the corresponding results from different expression experiments.

Lengthy table referenced here

US07838650-20101123-T00001

Please refer to the end of the specification for access instructions.

Lengthy table referenced here

US07838650-20101123-T00002

Please refer to the end of the specification for access instructions.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

LENGTHY TABLES

The patent contains a lengthy table section. A copy of the table is available in electronic form from the USPTO web site (http://seqdata.uspto.gov/?pageRequest=docDetail&DocID=US07838650B2). An electronic copy of the table will also be available from the USPTO upon request and payment of the fee set forth in 37 CFR 1.19(b)(3).

SEQUENCE LISTING

```
<160> NUMBER OF SEQ ID NOS: 117

<210> SEQ ID NO 1
<211> LENGTH: 2039
<212> TYPE: DNA
<213> ORGANISM: Arabidopsis thaliana
<220> FEATURE:
<221> NAME/KEY: misc_feature
<223> OTHER INFORMATION: Ceres Promoter construct YP0001 as found in
      Promoter Report #1
<220> FEATURE:
<221> NAME/KEY: misc_feature
```

```
<223> OTHER INFORMATION: T1 Mature Plant Expression: GFP expression
      observed in Sepal (Se), Receptacle (Re), Pedicel (Pd)
      in the upper part of the receptacle of the flower
<220> FEATURE:
<221> NAME/KEY: misc_feature
<223> OTHER INFORMATION: T2 Mature Plant Expression: GFP expression
      observed in Pedicel (Pd) and Stem (Sm) in the inflorescence
      meristem, Epidermis (Ep), Pedicel (Pd) and Stem (Sm)
      in the pedicel junction of the stem, the flower
<220> FEATURE:
<221> NAME/KEY: misc_feature
<223> OTHER INFORMATION: T3 Seedling Expression: GFP expression observed
      in the junction of the Cotyledons (Co), the Cotyledons
      and the Hypocotyl (Hy), the vasculature of the root,
      the Epidermis of the root tip
<220> FEATURE:
<221> NAME/KEY: misc_feature
<222> LOCATION: (2023)..(2023)
<223> OTHER INFORMATION: n is a, c, t, g, unknown, or other

<400> SEQUENCE: 1
ctgcattcac acatattttg ggctctcacg tgtttgtgaa tttaatatat ttgactacac      60
gatctttcaa cgtatgaaaa agttttatac tactattttc gtttgagtgg gaaataaaca     120
aatgatagct acagttatct atatggtata attttacact tttataacta ataatgatga     180
gtgatgacaa tcgagtgtcg gatataacag gccaacaagt ggaatggact tatgtaactt     240
tttaatcacg ggattaaatc acgtaaccca atgtcctaat tggtatttaa ttttgattat     300
ctcgatgcta catattgtca taggactcat atctttgatc acgtgccgct accaatccag     360
acattttagt atacaaaaaa aagaagdata caaacttaag atatggaata tatatcagaa     420
ctatcagttt tagactttaa taattcgaat tgaataacta cgatcaatat ataaattggc     480
aaatagattg gtcaattgta gtgcaagaaa tttgtgaact ttattacagt acgaagagag     540
taagagaagc aagatccggt ttttaggcaa caagtaacat ttttgagttc agagagtttg     600
cttcttactt taagttacgt cactacaaaa gccaagttcc tacttcttag gtctaaagtc     660
aatttcgaa tattcagaaa aattgtactc tactagatcg aatagttttc accggtgaaa     720
cgatatataa atgaagacta caatattttt taattttttt aagcgtatga gttctagacc     780
tttggcacgt aaatttctcc ggtacctggg accaatcgtt gataatatca cgtttaagat     840
ttaatcatcc atcccaagta gagttgaact agtaaccttg agcactttt ctcgagacaa      900
ctaaaccatc atccacttag tgcaataaag cgtcattctt ttttttcttt tcaaaaattc     960
gtatttaatt ttaatttatt aaaaatattt cttttgtttt aaattgggac agaattatca    1020
tttaacatat ttaaaattta tattttaat taaaaatagg gtaaaatata tttttcaaac     1080
aaaaattcaa aaataggcga attttcaaaa tcatccattc ttaaatctaa agtcggctac    1140
agtctttcg ttgttttgtt gctaatttca atttatatac atgcaaatta caaaatataa    1200
tagttttgg gggataatta tcttcttgcg cctttttatt aaattaatat gctcatatag    1260
cagttcttac aattaatata actagggttt taaatttcaa tatcgagttg acaaaatgaa    1320
ttgtttacaa gttttttct tttcaatatg cattgttcat cacgtattcg tagtgatgca    1380
aaacaaact ataaattata attgcactag tgagattagc aagaagtgtt ataaattaga    1440
ataaacggaa ctatcaaact gtgttatgta caccatttat ttttgttaaa gaatatgtgt    1500
agtagttaga aaactgatca aattaaactg aaaattcaca ttacggagat caagttacat    1560
tgtctattga tgaaaaaaac aaaataaatc caaatggcac taaaagttgt agaaattgaa    1620
agaagaaaat agatttttgt ctaggaataa aagtcaaaat gggaaagaca aaaaaaagag    1680
aggcaaataa gcagtgatgg agctaaagca acgcttact cttttaatta tgaattattt    1740
```

-continued

```
gatttgacct ccactcgcct ggctttttt ggttgttctt tatagaaaag taaaataaca    1800
caattagcac ataacatgag ttatcgagaa accaattctc tttgtggtgt tttagttaat    1860
ttctataact tatgaaacca ttttctcagt ttatcatgat aattgatcct ctatttaaaa    1920
ccctaaagtt tatattttgt ttgttcaaac acagtcgcca ttgcactggg atccaacaat    1980
gtcctccgac tcgtccaaga tcaagaggaa gcggaaccgc atncctttaa cgaaggcga    2039
```

<210> SEQ ID NO 2
<211> LENGTH: 1129
<212> TYPE: DNA
<213> ORGANISM: Arabidopsis thaliana
<220> FEATURE:
<221> NAME/KEY: misc_feature
<223> OTHER INFORMATION: Ceres Promoter construct YP0007 as found in
      Promoter Report #2
<220> FEATURE:
<221> NAME/KEY: misc_feature
<223> OTHER INFORMATION: T1 Mature Plant Expression: GFP expression
      observed in the Endosperm (En) and Inner integument (Ii) of the
      fertilized Ovule (Ov)
<220> FEATURE:
<221> NAME/KEY: misc_feature
<223> OTHER INFORMATION: T2 Seedling Expression: GFP expression observed
      in the root transition zone of the Root (Rt), Atrichoblast (At)
      within the root differentiation zone of the root,
      T3 Seedling Expression, cotyledons

<400> SEQUENCE: 2

```
agcagaacaa ctatatttat tgtgtcacat aaatctgaga tcatttataa ccaccaaaga      60
acctatacac agtaaatgac aaatgtatct ccctctatct ctattgccca tatgtagatg     120
ctaaagtaag atttctcttt tttttaatgt acttttttt gtataaagta tattccataa     180
gaaaaaggaa aagcttgttt atggatcaat tgaccccaaa aaaagttttt agatcaaagc     240
ccaatataaa aaaaaaacac agtagtgaca caaaggaact taaataaacc atgaattgat     300
ctataaacag tagagatcga taaggcgaac attttccatg tgaagtgtct tctttcatct     360 ataatattt tgacatccaa taatttcctc tataatatca ttcacataat tgatagaaac     420
attatgttag aattgtccac atcatttgag ctgtaatata ttctgtttta acaaattata     480
tggtagttgc ttaatcttat gtccatcttc ttctatgcat cgttttcgcg cctagttgtc     540
cagtccattt caactaccta cctctaattc ttatcttaaa acaacatttt ttaatttaag     600
tattatgctc aaagactaac tagatagaaa accgttatta aacattaaac gaattaaaag     660
tcttacatgg aaaatgtagg tttataaacc acgagttatg attgacaata aaaaaatgc      720 aaatcatcaa tcaaaagaga cttgagtgcg actctatatc aaccattgca attaaaatta     780
tctatcacaa aaattttaga cagattaagt taatttagtc taaattcact aatttattt      840 ctataattag taattaacta tatttatttta tttacacatt ttctgataat ttagaaattt     900
gcatgaataa caaatataag attttggaaa ttagtagcaa atttaattaa taattatttt     960
tgcctaaatg aaccaaacta taaaacctcc acatacacca gtcatcaaat ttacagagac    1020
aacaaactaa agttggtggt gatagagtga gagagaaaca ccattgcact gggatccaac    1080
aatgtcctcc gactcgtcca agatcaagag gaagcggaac cgcatcccg               1129
```

<210> SEQ ID NO 3
<211> LENGTH: 1035
<212> TYPE: DNA
<213> ORGANISM: Arabidopsis thaliana
<220> FEATURE:
<221> NAME/KEY: misc_feature

```
<223> OTHER INFORMATION: Ceres Promoter construct G0013 as found in
      Promoter Report #3
<220> FEATURE:
<221> NAME/KEY: misc_feature
<223> OTHER INFORMATION: T1 Mature Plant Expression: GFP expression
      observed in the Vascular (Vs) of the leaf
<220> FEATURE:
<221> NAME/KEY: misc_feature
<223> OTHER INFORMATION: T3 Seedling Expression: GFP expression observed
      in the Epidermis of the Hypocotyl (Hy),
      the Vasculature (Vs) of the root,
      the root tip and lateral root tip

<400> SEQUENCE: 3
atcttgtgat acacaattta ttactatttg gtacattttg aagtatttgt ttttgcatga      60
tatatgacgt taatttgaac tgatattagt caatttatgg gtacaaaagt tgaaagttta    120
gagcactatg ttggatttat taaaaatgat atcatacaat ggttcaatat atatatattt    180
ttttccacgt ttttaataac attttttgtaa acaagtcttc tactattgtc tttattgtta   240
atgagtttct agtacctaat taggaatttt gaggatatac gatacattaa tgagttacat    300
tatcccgaaa acaaaatctt gaaaacgaac aaagataatt tggacattac tcgttatgta    360
tacgtatgga attggataga gccgttgaac catcaagtgg gtcttcaagt caacgaactg    420 aatttgatt tacactcatg tacatcggcc acaattttat tcacacacta ctaacacctc    480
tggtgtccac ttttttcttt ctctagattg atgtgttaag attttttgttg caattcattt    540 attcaggtat ttttatatat atatatatat aaattagaat aaactaattt aaagaaagat    600
atagcaatta tgtttcacat tttaacattc tcaatcattt ataaaactaa tgtggtgatg    660
aatggtatat atatatatat atatatatat atatacatat atatatttg ttgtgaacta    720 atggtaaata tttaaaataa gacatacgta cataaatcca cgggctctta aagtcatgat    780
gcggttaata aatgttcaca taacggtaac caagtggctc aaaatcatga aacaacgtca    840 cataattttat cttataatgt ggataattag taccgcatta tttgtaagaa aattaaatta    900
attatagatt cacagctaag aaaatacgaa aagacagctc aacactttc cacttctatt    960 ccccactgtc tatataactc tgataaataa tctctgatct ctccaccatt gcactggtcc   1020
aggagataaa caaga                                                    1035

<210> SEQ ID NO 4
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0097 as found in
      Promoter Report #4
<220> FEATURE:
<221> NAME/KEY: misc_feature
<223> OTHER INFORMATION: T1 Mature Plant Expression: GFP expression
      observed in the Embryo and Suspensor of the four day embryo,
      the globular Embryo, the heart stage embryo and
      the torpedo stage embryo
<220> FEATURE:
<221> NAME/KEY: misc_feature
<223> OTHER INFORMATION: T1 Mature Plant Expression: GFP expression
      observed in the Embryo and Outer Integument of the ovule,
      the Funiculus and Placenta of the ovary,
<220> FEATURE:
<221> NAME/KEY: misc_feature
<223> OTHER INFORMATION: T2 Seedling Expression: GFP expression
      observed in the Epidermis (Ep) of the hypocotylin the Cotyledon
      (Co), the Stipules (Ss), the lateral root initial, the lateral
      root cap

<400> SEQUENCE: 4
```

-continued

| | |
|---|---|
| ttcatcttta tatttaagag tttaaaaact gcaacttttg ttttctttc actaagtctt | 60 |
| atggccacag ttaattaaaa gcagatgaaa ggtggtccaa tggaaaagga gaatgtgatt | 120 |
| gggctagttg ggagagttct gatgtctagt gttgggtaca cgtgtccgtc agttacacat | 180 |
| agcattaaat cagacggcat gtcattattc aaatctagtt cacatagtac gactaatagc | 240 |
| tgataaatta atgattatac agcatatgaa ttatgaattc aaaaaaaaaa aaaaattgaa | 300 |
| aatgttaagg agatgctata ttttacaaaa ttcatcgcaa tgctttctac taatttgcta | 360 |
| agtggtcttc tccagttagt cttgtcgatt ccaagcgata ttattaaatc ttgaagcatc | 420 |
| gctcaaagca ttatagctta agataaccaa attgttatta aaacaccta gtgaaatttt | 480 |
| taaattaaaa caattttgat atctttgtaa tatctaatac tactctttct gtgtctaaaa | 540 |
| ggattaattt tcaaaaattt cacacatatt aaaaaaaaaa aaaaattact agctaaacaa | 600 |
| ttttcaataa tcataaaaca atagtaactt aataatttt ttttattttc aaaatagtcc | 660 |
| ttcaagttta caattcattt tagtattata atcaacaaaa tttgtattaa aaagttggaa | 720 |
| aattaatctt tgtggaacaa aaaaatctag aaatcatttt ttagaattag agagaggttt | 780 |
| gataaaaaaa aataaaaaaa aatagagaga ggtagtacat actaaacgat gtgatactac | 840 |
| tattgacaaa atcttaattc tcagtttagt agaataaact agaaggaatg aatgaagtaa | 900 |
| atgcgaatcc aactactaac aaaccctact tagtcatcat attttcccat atgaaatccc | 960 |
| tatataaacc catcatcatc tcccactttt ttcatatcca | 1000 |

<210> SEQ ID NO 5
<211> LENGTH: 1068
<212> TYPE: DNA
<213> ORGANISM: Arabidopsis thaliana
<220> FEATURE:
<221> NAME/KEY: misc_feature
<223> OTHER INFORMATION: Ceres Promoter construct YP0111 as found in
      Promoter Report #5
<220> FEATURE:
<221> NAME/KEY: misc_feature
<223> OTHER INFORMATION: T1 Mature Plant Expression: GFP expression
      observed in the Endosperm (En) and Seed Coat (Sc) of ovules
<220> FEATURE:
<221> NAME/KEY: misc_feature
<223> OTHER INFORMATION: T2 Seedling Expression: GFP expression observed
      in the Endodermis (Ed), Epidermis (Ep),
      Lateral root primordium (Lr) of the root,
      the Pericycle (EP, PE) of the Stele (St)
<220> FEATURE:
<221> NAME/KEY: misc_feature
<223> OTHER INFORMATION: T2 Mature Plant Expression: GFP expression
      observed in T2 Mature tissue expressions similar to T1 expression
      data, the Inner Integument (Ii) of developing seed, the maturing
      seed

<400> SEQUENCE: 5

| | |
|---|---|
| cgattggatt tagtctatac attatagggc gcaagtttgt ggatttaaga attatataaa | 60 |
| aacttgaaat atatagtttt tatgcattct cctcttgtgt aatacataaa ccaaatatga | 120 |
| gataggttaa tctgtatttc agataatatt aaattccaaa caatattttt acttgttata | 180 |
| agaaggcaat taatatctct ctgttaatgg caagtggtac caagtagtat taaactatta | 240 |
| atgcaatgga agagtactgt tggaaattat aatcctctat cacacattca aacgatctc | 300 |
| ctgaaatctt ctcttccaaa cttgtacttc tctgatccaa atgtaggctc caaaatatag | 360 |
| acatttacca tttactaagt ccacaactcc tttcttgtct ccttcaaaaa tgactcttgt | 420 |
| gtaaccacca tatgactccg acagttcggc attgccatga tgagagctta aaaattcacc | 480 |

-continued

```
ttcctgagca tttcaagtct tcactcccttt agcttgacct gaaccaagat aaaatgcctt      540
tgtcgtcccg taatatccat cctgctttgg acggcatcat agttacattc gatccatcct      600
atttacaatg ttattttagt attaaaaaca tgacaataaa tttgttgtta aacatattca      660
aatacaatat gattggattt ataagtaatt gtaatatgaa atgtccttag taatatgtta      720
aaaaatacat agatacacac acgtactaaa agaggcaacg cgggagatgt cattagagga      780
agaactagga agcagagcgt tcatgcaaaa tgctaccaaa acgttaatg caatatctca       840 actaatcagc acagtccatt tcatactgag aatgtaaaaa ccaatcagca tcgtccattt      900
tttcatctaa ttatttgtta actcttaatt ggccacaact tccaaccaca tgacgctctt      960
tctattccct ttatatattc ccatctcaaa tgttcttgga gacacaaaat atcataaaca     1020
tataaacata aacgccaatc gcagcttttg tactttggc ggtttaca                    1068
```

<210> SEQ ID NO 6
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter construct YP0104 as found in
      Promoter Report #6
<220> FEATURE:
<221> NAME/KEY: misc_feature
<223> OTHER INFORMATION: T1 Mature Plant Expression: GFP expression
      observed in the Pedicel (Pd) of the inflorescence meristem, the
      stem
<220> FEATURE:
<221> NAME/KEY: misc_feature
<223> OTHER INFORMATION: T2 Seedling Expression: GFP expression observed
      in the Epidermis (Ep) of the hypocotyl,
      the Epidermis (Ep) of the cotyledon petiole,
      the Epidermis (Ep) and Cortex (Cr) of the hypocotyl

<400> SEQUENCE: 6

```
tttattttat tttttgaatg aaaatgtctt ctttattcgt aattttaaac tcactggtgg       60
tggatatatt gttatgtccc caattcgtct ggcaactctc gtatattagt gagaaaaatt      120
tgtccattat ttactgcact attaccctgt gttaattttt tgtattgaaa ttgttttttt      180
agtaattcac gtcatatagc gaatgattct ttaattttaa aaattcagtc ttaagtttac      240
aaattaaata acgctactgt aaccaactct gtacgaccaa catgttcgag ttttgtata      300 tacggccata tatgtacata ttttactata aagcgaaaaa atccataaat tatttaatta      360
atatataaag gtgccattct atttccaatg tgcttaggaa aatgcagaac ctcgtgctat      420
atctctgtcg ccacgtgcaa atataacaat atgaaataga actagcaaat cttgaaatct      480
aactcttaag actaattcaa gcacatacgt agagaaagtt gaccaacggt tatcagcatt      540
ttaacatgga ccttatcaac attttaacaa agtccacaaa caaccagtct tacaatcgca      600
ttggtacaag ataatcgaat tcatcttcca tataacaaaa cctaaacctt ggtgtgaaaa      660
ggagaagata tgtatgttaa aggccgccta tgcctctggt ttggggtata tgattctaag      720
attagggttt gaatattttc gttagcctgc catgagatat attttatgtga taatttagag     780 cctcttatgc attaatgcat aaccgactag atccatgtgg tattcagcta atcagtacac      840
acaagacaaa gtagtaaatg agtttgatga agactgtggt ctgataattc ctatcaacgt     900
taaatctgtc ggggccaggc agccagcaac attttgccta ccaacgctct gaattcaatt    960
gaacctaggc tatataatag caggctaact taactaagag tt                         1002
```

<210> SEQ ID NO 7

<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0075 as found in
      Promoter Report #7
<220> FEATURE:
<221> NAME/KEY: misc_feature
<223> OTHER INFORMATION: T1 Mature Plant Expression: GFP expression
      observed in the Guard cell (Gc) and Vasculature (Vs) of the petal
      and sepal in the flower, the Lateral vasculature (Lv) and
      Medial vasculature, of the silique, the Guard cell of the pedicel
<220> FEATURE:
<221> NAME/KEY: misc_feature
<223> OTHER INFORMATION: T2 Seedling Expression: GFP expression observed
      in the Guard cell (Gc), that define the
      Stomata (So) of the cotyledon
<220> FEATURE:
<221> NAME/KEY: misc_feature
<223> OTHER INFORMATION: T2 Mature Plant Expression: GFP expression
      observed in previous generation, T2 Mature tissue expression,
      the Epidermis (Ep), Guard Cells (Gc) and  Vasculature (Vs)
      of the proximal, mid and distal siliques
<220> FEATURE:
<221> NAME/KEY: misc_feature
<223> OTHER INFORMATION: T2 Mature Plant Expression: GFP expression
      observed in the Epidermis (Ep) and Guard cells (Gc) of the
      mid region of the siliques and the stem
<220> FEATURE:
<221> NAME/KEY: misc_feature
<223> OTHER INFORMATION: T3 Seedling Expression: GFP expression observed
      in T2 Mature tissue expression (if different expression pattern)

<400> SEQUENCE: 7
tggattacaa atcattaagc taatatcttc gatgaattaa aagataagt ggataacaag      60 tacctaaccg caatagtcca taaattaaaa cattaatgta tttgtcgttg aaaatttggc    120
cgacttttat ttgttattct agtttccaca tcaaaaatgt ttgtacttcg tagcaatcca    180
tccacctaaa ccccaaatct taatttatat ttgttgcgtt taaatttggg tgagatttga    240
ttctaagtag ttgagataaa ttgatattct attcattagt aaaatgatag agaaattggt    300
ttataataat tttaccctag aacatgacat gatattggta accattaatc aaagaaagag    360
caaagcattt aatttaccct actctccaac cactccagcc tttattagtt gcagttggga    420
atcatttctt tatgattctt atgtcattgt ctcctaaatc aatgaagtgc cttgaccttg    480
ttactaattc gaacatagca aagccaacta catagatcct ttacaaagtt ctaaaaacag    540
gttgtttagg cgtctagaca aacaaaacca ttttgtacga ttcaacaaat tggtccatag    600
aatgttattg atctttcttg tttaggcatt cgataaatcg gctaatacat tattttttg    660 ttttgctttt tccttattaa aaatatgcaa agtattatga tgtttaacct gaactgaatt    720
ttacatttaa ctggatatag gaaaatattg ggttgaattt aataattaag caattgtcac    780
gtaaatcaaa ttgggcttaa tatatattgt tgatttcagc aaagacaaag ttgggccgtt    840
tcaatagtct tcacgcgatg taagcgttca ctaaccaact agagaagaca atcaaatgaa    900
tacgttccac gtgacgctta cgaacttgtc agtcactttg gtaatatgac agacagtaac    960 cagtaaaacta ctaatctctt tcgctaacga acacacaaaa                        1000

<210> SEQ ID NO 8
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter construct YP0016 as found in
      Promoter Report #8

-continued

```
<220> FEATURE:
<221> NAME/KEY: misc_feature
<223> OTHER INFORMATION: T1 Mature Plant Expression: GFP expression
      observed in the Receptacle (Re) and Vasculature (Vs) of the
      flower, the Phloem (Ph) of the leaf
<220> FEATURE:
<221> NAME/KEY: misc_feature
<223> OTHER INFORMATION: T2 Seedling Expression: GFP expression observed
      in the Phloem (Ph) of the root differentiation zone
<220> FEATURE:
<221> NAME/KEY: misc_feature
<223> OTHER INFORMATION: T2 Mature Plant Expression: GFP expression
      observed in similiar tissues to T1 mature expression data plus the
      hydathode region of mature leaves
<220> FEATURE:
<221> NAME/KEY: misc_feature
<223> OTHER INFORMATION: T3 Seedling Expression: GFP expression observed
      in T3 Seedling tissue expressions similar to T2 seedling
      expression plus, the Epidermis of the root transition zone of the
      hypocotyl, the Vasculature of the root, the Hydathode and
      Vasculature of the root

<400> SEQUENCE: 8
aaacatgttt tatgtaacta ctttgcttat gtgattgcct gaggatacta ttattctctg      60
tctttattct cttcacacca catttaaata gtttaagagc atataaatta attatcttca     120 aaaggtgat tatatgcatg caaaatagca caccatttat gtttatattt tcgaattatt     180
taatacattt caatatttca taagtgtgat tttttttttt tttgtcaatt tcataagtgt     240
gatttgtcat ttgtattaaa caattgtatc gcgcagtaca aataaacagt gggagaggtg     300
aaaatgcagt tataaaactg tccaataatt tactaacaca tttaaatatc taaaaagagt     360
gtttcaaaaa aaattctttt gaataagaa aagtgataga tattttacg ctttcgtctg     420 aaaataaaac aataatagtt tattagaaaa atgttatcac cgaaaattat tctagtgcca     480
ctcgctcgga tcgaaattcg aaagttatat tctttctctt tacctaatat aaaaatcaca     540
agaaaaatca atccgaatat atctatcaac atagtatatg cccttacata ttgtttctga     600
cttttctcta tccgaatttc tcgcttcatg gtttttttt aacatattct catttaattt     660
tcattactat tatataacta aaagatggaa ataaaataaa gtgtctttga gaatcgaacg     720
tccatatcag taagatagtt tgtgtgaagg taaaatctaa aagatttaag ttccaaaaac     780
agaaaataat atattacgct aaaaaagaag aaaataatta aatacaaaac agaaaaaaat     840
aatatacgac agacacgtgt cacgaagata ccctacgcta tagacacagc tctgttttct     900
cttttctatg cctcaaggct ctcttaactt cactgtctcc tcttcggata atcctatcct     960
tctcttccta taaatacctc tccactcttc ctcttcct                            998

<210> SEQ ID NO 9
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0094 as found in
      Promoter Report #9
<220> FEATURE:
<221> NAME/KEY: misc_feature
<223> OTHER INFORMATION: T1 Mature Plant Expression: GFP expression
      observed in Chalaza, developing floral buds (numbered), Embryo
      (Em), Inflorescence meristem (Im), Micropyle (Mp), and Phloem (Ph)
<220> FEATURE:
<221> NAME/KEY: misc_feature
<223> OTHER INFORMATION: T2 Seedling Expression: GFP expression observed
      in Cortex (Cr), Cotyledon (Co), Epidermis (Ep), Hypocotyl (Hy),
      Lateral root (Lr), Pericycle (Pr), Rosette leaf (Rl), Phloem (Ph),
      Vascular bundle
<220> FEATURE:
```

```
<221> NAME/KEY: misc_feature
<223> OTHER INFORMATION: T3 Seedling Expression: GFP expression observed
      in Root vasculature

<400> SEQUENCE: 9
taaagatcag aagaggaagg tttcgccgcg gcggttgcat cttcaccgtc gatttcatcg      60
ttacagcgac gccggtaatt cctaggttgc ttagttccca ttctctctct aaaattaggg    120
ctcgaaatga attgttgaac aagatagaga tcttttttctg atccccgtcg aacatttatt   180
caaggccaaa aaaagcacac gggaatttag agtaccaata catatcaaaa cctaatgggc    240
tttgaatggt tgcatgtgtg tgtttatttc tgatatgcaa agcgatcgat agtcttttcc    300
atacaagtgt aaactgtaaa caacgtaatt aagcataaca atacaactct ttcttctctt    360 ttttttttgta aacacaaaat aaaattacat caattcatgc tttcctagt tcatctgaca    420 ttttccaaaa ttcatgttcc attgagtccc taatacttgt tcatattcat attagggtac    480
atgaataaaa gttatcattc ttgaaactac taaattttca tagtttatt ttcttctttt     540 cgtttcactt tcgaacaaaa cactacgcgt ggcatttgca atgaattcca cattatatgg    600
aataacacca tgatgaacat tctacatata taattattat gtttaagcac ttagacagca    660
taaattcttt ctaattatat aaatctaacc ttgttacatt gtacatctat aaattacttg    720
aagaaataac gagttctatt tctttttaaa aattaaaaat actataccat atctcagtga    780
ttaagttgaa ccaaaaggta cggaggagaa acaagcattt gattcttcct tatttatt     840 tattcatctc tcactaatga tggtggagaa aaaagaaaa tacctaacaa acaaatatat     900
attgtcatac aaaaatattt ctatattttt agttaattag tttatattcc tcacttttca    960
gggcttatat aagaaagtga gcaaacacaa atcaaaatgc                         1000

<210> SEQ ID NO 10
<211> LENGTH: 691
<212> TYPE: DNA
<213> ORGANISM: Arabidopsis thaliana
<220> FEATURE:
<221> NAME/KEY: misc_feature
<223> OTHER INFORMATION: Ceres Promoter construct YP0033 as found in
      Promoter Report #10
<220> FEATURE:
<221> NAME/KEY: misc_feature
<223> OTHER INFORMATION: T2 Mature Plant Expression: GFP expression
      observed in the Vasculature (Vs) of the sepal of the flower, the
      Guard cell of the pedicel, the Guard cell (Gc) of the silique
<220> FEATURE:
<221> NAME/KEY: misc_feature
<223> OTHER INFORMATION: T3 Seedling Expression: GFP expression observed
      in the Guard cells of the leaf, the Root hair and Epidermis
      of the root transition zone between hypocotyl and root,
      the Atrichoblast and Trichoblast of the root differentiation zone

<400> SEQUENCE: 10
gtcgattgga acttccaatt tctaaacgga tgcaataaga acttacatat tctctttcat      60
tagtcattta ttggccagat ttattaaaaa aagtttact caatgaccaa ggattagagt     120
taaagataat atagattatt acatatatta ttcgaaaaaa tacccatg tccgactttt      180 taaacctcaa aaatatcaaa accagaaaag atgatacaac acaaaaaaac aataaaataa   240
taagtggaag agatatcatc ggacaacagt acaagtacag caccagctct gccaaaagcc   300
aaaaccattt gtcaattaca gaaagatact aatgtttgaa attactaaat taccccctcgg  360 actttacaaa agcatctcta acttatccac gtgtcagtca tctattgatt gtttcaatac   420
caccttgtat taacgcccca cgattcgtgg ttgggtacac ctgatagtcc gaggatattt   480
```

```
aaatctcacg cgctcgtgtc tataattcga ctgtactcgc ttttcttgtc gtgattttag    540
caatttacga agtcaaatgt ttgactcaat cagacttgcg cataggagag cgagtataaa    600
tgtttactat actcacgcaa gtggggcttt attgaaacta ctcttttgta ataaaaccag    660
cagtggtttt gttctgaatc cgctctcttg c                                   691
```

```
<210> SEQ ID NO 11
<211> LENGTH: 992
<212> TYPE: DNA
<213> ORGANISM: Arabidopsis thaliana
<220> FEATURE:
<221> NAME/KEY: misc_feature
<223> OTHER INFORMATION: Ceres Promoter construct YP0049 as found in
      Promoter Report #11
<220> FEATURE:
<221> NAME/KEY: misc_feature
<223> OTHER INFORMATION: T1 Mature Plant Expression: GFP expression
      observed in the Sepal (Se) and Pedicel (Pd) of the flower,
      the Epidermis (Ep) and Phloem (Ph) of the sepal,
      the Epidermis (Ep) and Phloem (Ph) of the petal
<220> FEATURE:
<221> NAME/KEY: misc_feature
<223> OTHER INFORMATION: T3 Seedling Expression: GFP expression observed
      in the Phloem (Ph) and Epidermis (Ep) of the hypocotyl,
      the Phloem (Ph) of the root transition zone of the hypocotyl,
      the Guard cells (Gc) of the primary leaf
<220> FEATURE:
<221> NAME/KEY: misc_feature
<223> OTHER INFORMATION: T3 Seedling Expression: GFP expression observed
      in the Phloem (Ph) and Epidermis (Ep) of the Cotyledon (Co),
      the Phloem (Ph) of the root elongation zone
      and root differentiation zone
<220> FEATURE:
<221> NAME/KEY: misc_feature
<223> OTHER INFORMATION: T2 Mature Plant Expression: GFP expression
      observed in T2 Mature tissue expressions similar to T1 expression
      data, the Vasculature (Vs) of the stem
```

```
<400> SEQUENCE: 11
ttccaaattc ttatggttct ctagtgtcat gattttgaga atcactcaac tccaaaaata     60
taatccacga tcccgtgtta attattgaag aatcaatcgt ttttaatttc tcaccaatag    120
atgttgctct tattacttaa aacaaattgt tcggacaaat gtagcaagtg tgatactttg    180
tgggatctta aagacgattt ctcctataac agaggacaaa acaggtcggt caattacaat    240
gtcatccctc tttgccctgt ctttttttt cttcttaaaa cctaaccatt tgattgtttc     300
taaaggtatt tcaagaatat atgatcaatc tagatgaata ctataccgac gatgactaca    360
cacacaagga aatatatata tcagctttct tttcacctaa aagtggtccc ggtttagaat    420
ctaattcctt tatctctcat tttcttctgc ttcacattcc cgctagtcaa atgttaataa    480
gtgcacacaa cgtttctcg aagcattaga atgtcctcct cttaattaat ctccttctga    540
ttagattctc aatagagttt aaatttgtta atggagagat atattgggac cctcaaggct    600
tctaattata ccacgtttgg cataattctc tatcgtttgg ggccacatct ttcacacttc    660
attaccttat caccaaaaca taaatcaat caactttttt ttgccttatt gattgtgttg     720
gatccctcca aaattaaaac ttgtgttccc cacaaaagct tacccaattt cacttcaatc    780
ttaacaaata ggaccaccac taccacgtac ggtttgcatc atacaaacca caaactcctt    840
cttcattaca attattatat catctactaa aacctctttc tccctctctc tttcttgttc    900
ttagtgctaa attttctttg ttcaggagaa atatccattg cactgggatc caacaatgtc    960
atccgactcg tccaagatca agaggaaagc gg                                  992
```

```
<210> SEQ ID NO 12
```

```
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0060 as found in
      Promoter Report #12
<220> FEATURE:
<221> NAME/KEY: misc_feature
<223> OTHER INFORMATION: T2 Mature Plant Expression: GFP expression
      observed in the Guard Cells (Gc) and Vasculature (Vs) of the
      sepals of the flower, the Vasculature (Vs) of the Pedicel (Pd),
      the Vasculature (Vs) of the petiole
<220> FEATURE:
<221> NAME/KEY: misc_feature
<223> OTHER INFORMATION: T3 Seedling Expression: GFP expression observed
      in the Guard Cells (Gc) and Vascular (Vs) tissue of the Cotyledon
      (Co), the Phloem (Ph) of the petiole, the Vascular (Vs) tissue of
      the primary leaf, the Root hair (Rh) of the root transition zone

<400> SEQUENCE: 12
tggagcttta ttgaaatgca agaaagtaaa caaaggaaga tctttagatt gtcaccaaga      60
gtggtctgaa actctcataa cactcaatcc tcctcctcct catcaccacc actacaaaat     120
attatattct ctatctctca atctatgagg agatgtattc tatcaagcat ttgaaatgat     180
aagaaactgg cgatcatcct ctacgtcacc atcactccaa aattatcctc tttctaggtt     240
taagttttgt aatgatcgcc tttatttgtt gagatctcta acttctcgca tttccaaaat     300
gttaagtcca ataactgcat tggttaagtt ggggcgttac tagtcggctt aaatccaaat     360
atggatttga ttccatatgt atgtgacagt ttcttaacgt tcatattaca atgaatgatg     420
gatccttgac tagacaaaga gaaatggat tgtcacttcg taggaaaaat agaaattctc      480
cacgaaggct ggtctccttt atttaacgac aaattcactc atagtctcat tcacaatttg     540
aacttgtcta acacaatgtg ttatatactc gcgaaaagaa gcataatagg ctcttaaggg     600
taatccacga aaccaaaaca catataaaac attaatattt ttctctaaat ttattcatat     660
caataataaa gtttacaaaa aatataaaac aataatccat acttagccca tagcttcgtg     720
tggaagaaga cttgattttt gactagtcaa cgaaaatgag taaatgacgt attcagctat     780
agtaaagggg atcataagcg gaaattacaa agaagctttg agggtaaact agtcaaaaag     840
cataatcaga aataacttag gcccaaagca aaaaggaaag ggctctggat ccagccgcaa     900
atcagaatct ggtaagttcg aacgccacgt catcacctaa atatctgaaa tatctaatta     960
agacttgtct atatataaag gcttctcctt tcacaatccc                         1000

<210> SEQ ID NO 13
<211> LENGTH: 1069
<212> TYPE: DNA
<213> ORGANISM: Arabidopsis thaliana
<220> FEATURE:
<221> NAME/KEY: misc_feature
<223> OTHER INFORMATION: Ceres Promoter construct YP0092 as found in
      Promoter Report #13
<220> FEATURE:
<221> NAME/KEY: misc_feature
<223> OTHER INFORMATION: T2 Mature Plant Expression: GFP expression
      observed in the endothelium layer surrounding the embryo of mature
      ovules

<400> SEQUENCE: 13
aaagattgag ttgagagaga tggtggagac gcagaacaga caaagggagt ttaccatata      60
gtgctctaaa gggcaatgag attgcagtga tgtggctatc cggggaatca tcgcaggtta     120
ttccttccca tgagcaacaa tcaatggatg ggttccaatt cagaggagaa acagaagaag     180
```

```
aaacgtttcc agagaaccac agtagggatt ctcgatcttg cgagttgcag agagcctctg    240
aaactgcaat agaaaggaca ctgatgaaaa gaacacactg aaggagtatg ccaatcatgt    300
gaaaactcag agcttgtatt ggtcttgtgg ttgatgaagt tctcacaaaa cctttggctt    360
tgaatctccc ctcattagtc atggtgagaa caagaacaag acgagaaaca gacaaagaag    420
atgaaaaaac ttgttggcca gtgttgacta aggggaata gccccagaca taacaaaatt    480
agacttgtcg tacatcttta atattttttt atctgtttct ttgtcctgac gctttcatta    540
ttcctgtgat caattttctc ataccattgg tccatcgtta atcctttctt aatttcattt    600
tctacgtaac atgagaggag accaagtcct atgagaacag ttgacgtaac agtggttgtt    660
aagttaagtt aaaaagagga agctagtgag agtgaccgtt aggtagagaa gtgagatctt    720
taaccactct tctttctctc tctctctgct tttttcgtcg tctttcacat ctactgttcg    780
caaactctct tatgcttcca ataatggtga taccaattga gacttgcagg agaatctcct    840
cttctccaca ctctatcaac tggtcagcca tggaatggtc gtttcagttt caatattcct    900
ggattctttt taaggattcc tgtttctctt ctgttcctgg tatattctta acgacgaaat    960
tagtatcgga tcctggtaat acattttgaa gcttttaagt accattgcac tgggatccaa   1020
caatgtcctc cgactcgtcc aagatcaaga ggaagcggaa ccgcatccc              1069
```

<210> SEQ ID NO 14
<211> LENGTH: 1687
<212> TYPE: DNA
<213> ORGANISM: Arabidopsis thaliana
<220> FEATURE:
<221> NAME/KEY: misc_feature
<223> OTHER INFORMATION: Ceres Promoter construct YP0113 as found in
      Promoter Report #14
<220> FEATURE:
<221> NAME/KEY: misc_feature
<223> OTHER INFORMATION: T1 Mature Plant Expression: GFP expression
      observed in the Lateral vasculature (Lv)
      and Medial vasculature (Mv) of the silique
<220> FEATURE:
<221> NAME/KEY: misc_feature
<223> OTHER INFORMATION: T2 Mature Plant Expression: GFP expression
      observed in T2 Mature tissue expressions similar to T1 expression
      data plus, the Medial vasculature (Mv) of the silique

<400> SEQUENCE: 14

```
tatgaagaaa ttataataga ctctcataaa aatagtgtta caacttacat tctcttatat     60
agaaattagg ataaacagaa atgtaaataa tatatttcga ataatgttaa aatttcctaa    120
attctaatat taatatttat aaatggtcat ttaacttttt cgtaccggtt cgatgggaca    180
tgtgttatat tcagttaagg ttaccaccat gcgccaactt ggcctctacc aagtcaacat    240
ggatatggac cttatggtta catgccgcct ccgcctccac cgctaccggg atatggatac    300
agaggtccgc cacctcagca accgacgagg aatgaaacaa ggcaataata tattgatgct    360
attgtggatt tagttactga taattagtgc cttagtgaca gttcaaaaat gttgttcatc    420
aataatctac aatttaaggt ttgtgttgtg gaatgtttca tgatttttatg aagtcttgct    480 tatcaaaaag tatgatgatt aagaatttga cttcatggca tattcatttg agttagcaaa    540
acttttttgt gttgcacctt caaatttata aatttatgat ttttaaccat cgaaattata    600
tatttgaaaa gactatctct acaagccaaa cccactgggc caccaatatg ggtttatctg    660
cgaaatctgt gaaccttaga aaatcaaagc ccatatccac tttgctggaa ctttgctgga    720
atgtaggtta gacaaaacct taagacgcag ctacaagtct cttatgtggc agatgtcaaa    780
attaatgagc acgtataatt tacccaagag gagcaaaata agattagcag cttaaattaa    840
```

-continued

```
ttgtgttgga ttaaatgaaa cttgcactat gaatggcaaa aaagaggtta caatctagca    900
accacctcat aaaccctcat taatgagata ctgactcgtg aaccaatcaa atctcaagtt    960
tcgtagttta aataagtagt aaacacctcc tgatcaaagc atcaccacca ccaaatatca   1020
aacgcaaaaa cctattatca aaagaactag ggaggaaatg actaatcccc atgatcatgg   1080
ttatgctgtt gttgtttctt gtgatgtcga ctagagcaga cgaagagctg attaagacag   1140
agtgtaatca cacagaatac caaaacgtat gcctcttctg tcttgaagcc gatcccaatc   1200
tccttcaata tcggaccgtg ctggacttgt caaccatcat taatacactg tctcgggatc   1260
tcaacttgat gttcttatca agtaagtttc accatgtaca ccattaatca ttattgtaca   1320
aataataata ttttttaatgt gttttcacaa aattaatatt acctcttttt tgtaaactaa   1380
tatgctacga aaattaacat actacgaaaa atgtgaatta atattacttt gcctgtaaat   1440
ttttacctcc ataataatat tagcatacca cgaaaaaatg taacgtattt cttttggtgt   1500
aatgtgaatt ttgctacggt aaacttactt tacaaagaaa gaagagcgtt ttccaagtgg   1560
aaaataatac attttgcggt ttatatatta taggaacgac tattgatttg ttttttttggt   1620
tgtaccattg cactgggatc caacaatgtc ctccgactcg tccaagatca agaggaagcg   1680
gaaccgc                                                            1687
```

<210> SEQ ID NO 15
<211> LENGTH: 999
<212> TYPE: DNA
<213> ORGANISM: Oryza sativa
<220> FEATURE:
<221> NAME/KEY: misc_feature
<223> OTHER INFORMATION: Ceres Promoter construct YP0095 as found in
      Promoter Report #15
<220> FEATURE:
<221> NAME/KEY: misc_feature
<223> OTHER INFORMATION: T2 Mature Plant Expression: GFP expression
      observed in the Guard cell (Gc), Lateral vasculature (Lv)
      and Medial vasculature (Mv) of the silique

<400> SEQUENCE: 15

```
ttcctcgacc atgccgttgc cggaaccggc tagcgcggcc ggccggcggc ggcggggagg     60
ccgcagtggg acgacgggtg aaggatcctc cagctgcgga aggaggtggt cctcgaggcc    120
gaaggggaga ggctacggag atggagggaa gccgaagaga agggaggctg ctgctgctgc    180
tgcatttggg agacgagaac tcgactcgag ccatggcggc agattggtgt tcacggcgg     240
aatgctaact agatccagca tctccatagc aaaggtagaa tggtagattg aggtgagttt    300
tttttcccct cttctgcagt tttgatgtat tattactgcc ctcatctgat ctgggtaaca    360
tatttctgag ctcagtagaa ctgttaaaaa aaggcagaaa tgcacaaact cttctcacaa    420
aacaacatac aaatgcttat attttggagc ggaggcaata catggtatat ttttaaagt     480
gaaaaaaca atcagacaca tggtattgag tgatagcaaa gctgggtgac cacagaaaat    540
acctcctgct ttaaatactt tatacctggg ctgtcaatcc tcggagttcc tcccaatgta    600
atgtctgagg aagaagtatt gcagctaaat tttaagggtt tcttgtacga aacagggaca    660
atcagagatt aagaaactct atgtggaaaa ggccatgcgc attttgttat gtgattcaac    720
aaataagatg aggaggcaaa gtcatggttc tgttctaatt aacaaatcta ctatggggc     780
cgttgctccc tattgtccac gctcctttc ttcatttctc tcctgcagga tatcttgtct    840
tttgattctt catttaggt cttataaata tcacgtggt caggcctcca atgtcaaatt      900
atcattacgt ggaactctct tagatgcttg agaaaagtta gctcttacct gtccatagaa    960
```

```
gctccaagga agcgagaata gtagatactt tggttggcc                              999
```

```
<210> SEQ ID NO 16
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0102 as found in
      Promoter Report #16
<220> FEATURE:
<221> NAME/KEY: misc_feature
<223> OTHER INFORMATION: T2 Mature Plant Expression: GFP expression
      observed in the Female gametophyte (Fgm) of early pre-fertilized
      ovules, the Embryo sac (Es) of pre-fertilized ovules
<220> FEATURE:
<221> NAME/KEY: misc_feature
<223> OTHER INFORMATION: T3 Seedling Expression: GFP expression observed
      in the Epidermis, Lateral root initial and Root hair of the
      hypocotyl-root, the Epidermis, Lateral root initial and
      Pericycle of the lateral root initial
<220> FEATURE:
<221> NAME/KEY: misc_feature
<223> OTHER INFORMATION: T3 Seedling Expression: GFP expression observed
      in the root epidermis, the Pericycle (Pr) of the lateral root
      primordial, the Pericycle (Pr) of the lateral root

<400> SEQUENCE: 16
atttggttga taacgttttc actcgactaa ttatatactt cagaaggata gtaatagaat      60
accaaaataa ttaaatgatt ggttagtgcc ttagtggaga cttttttaacc gattctaata    120 gactaatgat gtagctaagc atttatttgg gatcatcact gtttgaaaac gtgaaatgtg    180
ataaaagtta tgaaacgatt aaaatataaa ataaccgtac aaaacattat gtaccgtttt    240
tttctctgtt cttttggcga tttggtttag ttcgttacac tctaaatgtt attgcagata    300
tatatataat gatgcatttg catctgagga acatataatt ccggttaaca cttccaaatc    360
ttatatccgt ctaggtaggg attttataaa tcatttgtgt catcatgcgt tatgcttgtc    420
ggctttgacc ataacgcaga gatatagaac tagcttttac ttaacttttta gatttattat    480 ttgatctaga gttaagtgga gatatatagt gtttttgtta gattattggt ggatgtgaga    540
gtttgtcttt agtttcaagt tgagaatata aggcaagagg agactctgag gcaatcagag    600
gttttgattg gcaaaatatc caaaaggccc aaaccaagtc gaagcccatc tcgtacaaaa    660
aaagaaagag atctgtaaga aaaaatattc tttgatattc ttacaaaaat aagtgtaaaa    720
cttttattag tcaaaatctt caatctttaa aaactctcat cactcctacg aaagcgcgtg    780
agagttatga gacattcctt aatagcatta ctcacaagtc acaagttcaa aacgtctgac    840
tgaaacagaa acaagccttt gttgaagtct tgaagaagag acattagtac tcgtcgtata    900
gccataaaag gtaatatacg aaatttcttc gctaatctct tcaccttcct ctacgcgttt    960
cactttcact ttataaatcc aaatctccct tcgaaaacat                          1000
```

```
<210> SEQ ID NO 17
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter construct YP0103 as found in
      Promoter Report #17
<220> FEATURE:
<221> NAME/KEY: misc_feature
<223> OTHER INFORMATION: T1 Mature Plant Expression: GFP expression
      observed in the Female gametophyte (Fgm), Inner integument (Ii),
      and the Micropyle (Mp) in the pre-fertilized ovule,
``` the Inner integument (Ii) of the fertilized ovule
<220> FEATURE:
<221> NAME/KEY: misc_feature
<223> OTHER INFORMATION: T2 Mature Plant Expression: GFP expression
      observed in T2 Mature tissue expression (if different expression
      pattern), the outer integument(Oi) of the developing ovules,
      the seed coat (Sc) of the developing seed
<220> FEATURE:
<221> NAME/KEY: misc_feature
<223> OTHER INFORMATION: T3 Seedling Expression: GFP expression observed
      in root hairs

<400> SEQUENCE: 17

```
gttttgaaga acaatctgga tcgaaatcta acataaggtc atcgtattca agttacgcag      60
tcaaggactt gacatcatcc tactctggtc tgaggttacc acttccaaag atgggatttt     120
tcgactcggt atgcttccta agaaattcgt tttattgaac ctagcaaata tcttgtaatg     180
taagattcct gagatgatga agaaaaaaca aactttgtt acagcaggag aacggagaga      240
aagaaaacag agaccaaat gctcttgaag caaacagaag aagaagacac aaatccaaac      300
ttgagacttc ttctacacca gaaaaccgca gcattctggg acaacgcaaa acacgaaagt    360
gaaacgggca atgatatata tgtcttgggt gcgttacaag gcatcgtttg caactgttga    420
gttggataag tcaactgtct tcttttcctt tggttgtagt agctgccttt ttttccttt     480 gttgctttaa gaaatagccc gaaaaaaaga atgttctaca tttcggagca gaaaactaac    540
cgaatgagtt tttggtcgga tcatcggatc gatcagatat attttgagtt acgaactgtt    600
ataaaaaaag ccataatttt gtgttgagtt tgcaaaatac cttataactt gttatttgag   660
attgcacctc catatatatt aattcgtaag agtatttatt aagtaagctt tagtataaat    720
cctttttccc tttaaagtaa gttaatgttc tactaaataa tagtaaagtt gaagaaccgc    780
tccgttttta caccatgcac gtgttatcta acaaagaaaa tatggtacac ctaatggcta    840
atgcaaagga caacacaatg aaactaactt gactctgtgt tatagaaacc catagacatc   900
tgcatacatc ctagtatttg tataaattgg actcaaattc ctgaggacaa tcatagcaaa    960
caatcacatc atcgcaatat acataaacaa aagaggaaga aaaa                   1004
```

<210> SEQ ID NO 18
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter construct YP0107 as found in
      Promoter Report #18
<220> FEATURE:
<221> NAME/KEY: misc_feature
<223> OTHER INFORMATION: T1 Mature Plant Expression: GFP expression
      observed in the mature embryo, the Endosperm (En), the Endothelium
      (Ed)
<220> FEATURE:
<221> NAME/KEY: misc_feature
<223> OTHER INFORMATION: T2 Mature Plant Expression: GFP expression
      observed in T2 Mature tissue expressions similar to T1 expression
      data, late torpedo stage of embryo

<400> SEQUENCE: 18

```
taacaatcct tgggaacatt gcatccatag atatccggtt aagatcgatc tttgaactca      60
taaaaactag tagattggtt ggttggttc catgtaccag aaggcttacc ctattagttg     120
aaagttgaaa ctttgttccc tactcaattc ctagttgtgt aaatgtatgt atatgtaatg    180
tgtataaaac gtagtactta aatgactagg agtggttctt gagaccgatg agagatggga    240
gcagaactaa agatgatgac ataattaaga acgaatttga aaggctctta ggtttgaatc    300
```

```
ctattcgaga atgttttgt caaagatagt ggcgattttg aaccaaagaa aacatttaaa      360
aaatcagtat ccggttacgt tcatgcaaat agaaagtggt ctaggatctg attgtaattt      420
tagacttaaa gagtctctta agattcaatc ctggctgtgt acaaaactac aaataatcta      480
ttttagacta tttgggcctt aactaaactt ccactccatt atttactgag gttagagaat      540
agacttgcga ataaacacat tccccgagaa atactcatga tcccataatt agtcggaggg      600
tatgccaatc agatctaaga acacacattc cctcaaattt taatgcacat gtaatcatag      660
tttagcacaa ttcaaaaata atgtagtatt aagacagaa atttgtagac ttttttttgg       720
cgttaaaaga agactaagtt tatacgtaca tttattta  agtggaaaac cgaaattttc      780
catcgaaata tatgaattta gtatatat  ttctgcaatg tactattttg ctattttggc      840
aactttcagt ggactactac tttattacaa tgtgtatgga tgcatgagtt tgagtataca      900
catgtctaaa tgcatgcttt gtaaaacgta acggaccaca aaagaggatc catacaaata      960
catctcatag cttcctccat tattttccga cacaaacaga gca                      1003
```

<210> SEQ ID NO 19
<211> LENGTH: 1071
<212> TYPE: DNA
<213> ORGANISM: Arabidopsis thaliana
<220> FEATURE:
<221> NAME/KEY: misc_feature
<223> OTHER INFORMATION: Ceres Promoter construct YP0110 as found in
      Promoter Report #19
<220> FEATURE:
<221> NAME/KEY: misc_feature
<223> OTHER INFORMATION: T2 Mature Plant Expression: GFP expression
      observed in the Embryo sac (Es) of the pre-fertilized ovule,
      the Degenerated synergid cell (dSn) of the fertilized ovule

<400> SEQUENCE: 19

```
gggatgcggt tccgcttcct cttgatcttg gacgagtcgg aggacattgt tggatcccag       60
tgcaatggta atataaaaca agaaaacaag agatttata  ggacaatcac taaatgacat      120
ttaattgatt aaacattat  tcattaataa ttgtatgtta ctaacttcaa catttaataa      180
ttttgtttaa gatacgttta catcagagac tattaatatt tttacaggtt gtaactttaa      240
actttgtctt gaatcgaaca tgactataga ttttgggcaa acttaaagat aacaacattt      300
ccgttttttt tcaaattatt acaaatcaaa ctgatatatt agacacaaca cgattacacg      360
taatgaaaaa agaaaagat  aaaaagataa aagaagggat cgattctgtt tggtctggtt      420
tagtgagatt caaagttaag ctcttccttt caagacatgc cttcttaaac cgggaatgtg      480
aacgtttgta atgtagtccg tccagttaat gcttccaaca tcaaatccaa attctctctt      540
ctcgtcctct gacatattct ccattaatct ctggggtatt gctgttatca aatctgtaaa      600
agaaaccaaa aaaaaagat  gaaaactttg cgggtaccgg ttttgtctgc tctaagaatt      660
agaatgttaa tgagttctgt cttaccttcc accatagaaa gtgtatggct cataaatagt      720
agcaaggtgt ttggcttgtt caacagattt cttgcatata aactttagct tctgcatcat      780
cttactatcc actgaactca taccactcat caacccactc cgttcttgag catctctcca      840
caaatgatcc gagaaatcat caacggaatt gaaaagtttc atcaaacgca ccataatagg      900 atcacccttta gagtccatgc atggagatgt tttgtagtgg ttataaagaa gctccgctaa      960
gtcttcgaaa accagcgggt ttatcgccga agaagcgatc tgatacacgt ttatttcagg     1020
ttccggatct gacattgcca ttccatgctt tgctatagca gctaacgttc c              1071
```

```
<210> SEQ ID NO 20
<211> LENGTH: 1453
<212> TYPE: DNA
<213> ORGANISM: Arabidopsis thaliana
<220> FEATURE:
<221> NAME/KEY: misc_feature
<223> OTHER INFORMATION: Ceres Promoter construct YP0112 as found in
      Promoter Report #20
<220> FEATURE:
<221> NAME/KEY: misc_feature
<223> OTHER INFORMATION: T2 Mature Plant Expression: GFP expression
      observed in the Medial vasculature (Mv), Lateral vasculature (Lv)
      and Guard cell of the stigma, the Medial Guard cell (Gc) of the
      carpel

<400> SEQUENCE: 20
ttatgtgccc tgatgtccta tgcagatggt gcaactactg cttttggtga gaagcttcgc      60
gaacaagttg aggaaaggct agaattttat gacaaaggtg ttgccccacg caagaacgtg     120
gatgtaatga aggaggtgat agagaatcta aagcaaggta tttcttgtag ctgttttttt     180
ttggttgtaa tcagagtcct ctttatgatg gcaaactcag tgttttttta tctgttcctc     240
ctttagaaga ggaagggaag gagccagttg atgcctcggt gaagaaaagc aagaagaaga     300
aggcaaaggg tgaagaagaa gaagaggtgg tggcaatgga ggaggacaag tcagagaaaa     360
agaagaagaa agaagagagg aagatggaga ctgcagagga gaacgagaaa tcagagaaga     420
agaagacaaa gaagagtaaa gctggaggag aagaggagac tgatgatggt cacagcacca     480
agaagaagaa gaagaagtct aagagcgctg aatagaaagg gatgcaacat taacaaaccc     540
tgtattgtat ttttttttg agctaaatta atgtcgtctg ttttcgtag tgaacatcgg       600 agaatttttg ttttggtctg gaaacgattc aaggtttggc aatatcttaa gtttgtttag     660
gttttcacta ttttgacgtt tgcaaccgtg aaggaggctc ctccatttta taaaatacaa     720
ttaccaattc cagtgctttg caaatgtttc aataatagct aaactaacta ccaaattgga     780
aaactagctt aacaagtttg tgaaaatgaa tttggagcca tatgatttat tattttaccc     840
aaatggagta atagaagaag agcagctcgc gtttgaatgg tcagttaaca ttaacaaaag     900
gtaaaattga atagatgtta aaacttgtgt aagtaaacaa tagagctacc tccttttgag     960
aaggatagat aaactcgtga ccaaccacat tcccagtccc atattcttag tacaaataag    1020
aaattcacac ccctcaaaag aaatataaca taatcaatca taggaaatat acttcgcata    1080
atgacgataa tgatcaagtt tctcctgtta gctctgctcg tgatctctcc gatttgcgcc    1140
gagaaggacc tgatgaaaga ggaatgccat aatgcacaag ttccgaccat ttgcatgcaa    1200
tgtcttgaat ccgacccaac ctccgttcat gcagaccgtg ttggcatcgc cgagatcatc    1260
atacactgtc tcgactctcg tctcgatatc atcaccaagc aagttttccc ttctaataac    1320
catacatata tattaactta gatatatgac aatattctct aactaatata tcaatctttt    1380
tattgttcta ccattgcact gggatccaac aatgtcctcc gactcgtcca agatcaagag    1440
gaagcggaac cgc                                                       1453

<210> SEQ ID NO 21
<211> LENGTH: 1085
<212> TYPE: DNA
<213> ORGANISM: Arabidopsis thaliana
<220> FEATURE:
<221> NAME/KEY: misc_feature
<223> OTHER INFORMATION: Ceres Promoter construct YP0116 as found in
      Promoter Report #21
<220> FEATURE:
<221> NAME/KEY: misc_feature
<223> OTHER INFORMATION: T2 Mature Plant Expression: GFP expression
``` observed in the transmitting tract of the stigma, the Epidermis
(Ep)
<220> FEATURE:
<221> NAME/KEY: misc_feature
<222> LOCATION: (1065)..(1065)
<223> OTHER INFORMATION: n is a, c, t, g, unknown, or other
<220> FEATURE:
<221> NAME/KEY: misc_feature
<222> LOCATION: (1082)..(1082)
<223> OTHER INFORMATION: n is a, c, t, g, unknown, or other

<400> SEQUENCE: 21

```
aaacgcctct tcggtccacg ctgtcgtttt attgaaggaa ttatattta ttttaattgg      60
gcctgcaggc taaactataa gtccgtctga tatgggtcgg gttgggctta tgagttatgg    120
gtctggtagg ggtcaattag cttaatttcg atatgtgccc tactctcgac ctaacgtttt    180
gaacacgtaa gagagagttt ctaatattga gttgtctaat taactcgata ggcttataca    240
aagtgtttcc gcattttacc ttcttaataa ctcatcattc actaactaag aaaagtttta    300
ctcagaccat atcttccgct tcttgattat tgtcaatttg ttgtcactca atttatctct    360
tgcaaaattt agttgaaatc atttggtttc atctttggct cttgaatagt tgcatgtgtg    420
tatttagtaa gttcttttca attaagaagg aagaataaaa caaattgtgg ccagaaacaa    480
ttatgttgag ttttatctca tacgttggct cactcatccc catctctctg cttttgaatc    540
attctactcc tcccattttt tgatcgtcct tttttctgct tctgaacatg gatcattgtg    600
catgttcgga tgttcctcga tcgtgctgaa actcaaagtc tgaatcgatt accatagact    660
ctcaacccat ctttgatata taaaaagag ccttaaccca tctcttctac tctccctctc    720
tagaaacaaa cacatcacgt gatgatctgt ttcccccat acttacggga tgatcagaat    780
gtggcatgag gaaaaagcca agaaataagt tgataaattt aaggtttaat ttaacaaaaa    840
tgagagatta atcttttcat tttagggtcg cacgcggtgt tttgtgcaac cgcagaaact    900
tcctataaat accgatacaa tgtgcatgct ttctacaact caactcactc aaaccaaaaa    960
aagaaacatc aaaccccaaa acacacataa caatcacaaa ccattgcact gggatccaac   1020
aatgtcctcc gactcgtcca agatcaagag gaagcggaac cgcanccgt ttggaaatca   1080
gnccg                                                               1085
```

<210> SEQ ID NO 22
<211> LENGTH: 1100
<212> TYPE: DNA
<213> ORGANISM: Arabidopsis thaliana
<220> FEATURE:
<221> NAME/KEY: misc_feature
<223> OTHER INFORMATION: Ceres Promoter construct YP0117 as found in
      Promoter Report #22
<220> FEATURE:
<221> NAME/KEY: misc_feature
<223> OTHER INFORMATION: T2 Mature Plant Expression: GFP expression
      observed in the stem pedicel branch, the secondary Inflorescence
      meristem (Im), the Lateral vasculature (Lv) and Medial vasculature
      (Mv) of the silique, the ovary, the Inner integumentand Micropyle
      of the ovule
<220> FEATURE:
<221> NAME/KEY: misc_feature
<223> OTHER INFORMATION: T2 Seedling Expression: GFP expression observed
      in the Cortex (Cr) of the hypocotyl, the Epidermis (Ep) and Cortex
      (Cr) of the lateral root, the Epidermis (Ep) and Cortex (Cr)
      of the root differentiation zone
<220> FEATURE:
<221> NAME/KEY: misc_feature
<223> OTHER INFORMATION: T3 Seedling Expression: GFP expression observed
      in the Lateral root (Lr) of the hypocotyl root transition zone,
      the lateral root primordia, the Epidermis (Ep) and
      Vasculature (Vs) of the root

<400> SEQUENCE: 22

| | | |
|---|---|---|
| gtcagtgagt cgattggatc acagtccttt atgataaaac aaactcataa ttattccacc | 60 |
| gacaacatgc gttttaaatt atttttctt aaattatatt atattatatt gatatcaacc | 120 |
| tagctaaaat aattcggatg gcgaaatcgg acaattttta atagaaaaaa tgggtatgaa | 180 |
| gatagtctat gattccgttc ttagcgacta gagggacctg ctcaaatctc ccgggtgata | 240 |
| cgcgatgtca agctcaatag aaccccacaa ccgacgagac cgagaaatcc ttgatttggg | 300 |
| ctagaagatt tgaaataaa tttaatatat tctaagtaac ttgcttaaat ttttttcaa | 360 |
| actctaaaga cataactaac ataaagtaaa aaaaaaaag ttaatacatg ggaagaaaaa | 420 |
| aattaaacta atgattagct ctctaacgtg tttaatctcg tatcaagttt ttttttaaaa | 480 |
| attatattgc tattaaaaca ttgtactatt gtttctattt tgtttagcta ttattcttgt | 540 |
| gaaatgaaaa gttgtgttta ttcaattact aaatggcaat atttatcttg gaaaactata | 600 |
| cctctaattg gattaggccc tagacatcct ctttagctta ttgacgttaa aattattccc | 660 |
| aaaactatta agtttagta gtttgaaaga tgcatcaaga cctactcaga taggtaaaag | 720 |
| tagaaaacta cagttagtgt gattatattt taaaatatat aaaacaatct tattaaacta | 780 |
| aatattcaag atatatactc aaatggaaga taaaaacatt tagtctgtta ccactaccag | 840 |
| cctagctagt cactaatagt cactttggaa ctgagtagat atttgcatct tgagttacca | 900 |
| tggactcaaa agtccaaaaa gagaccccga gtgaaaatgc taccaactta ataacaaaga | 960 |
| agcatttaca gcggtcaaaa agtatctata atgtttaca caacagtagt cataagcacc | 1020 |
| attgcactgg gatccaacaa tgtcctccga ctcgtccaag atcaagagga agcggaaccg | 1080 |
| catcccgtta aacgaaggcg | 1100 |

<210> SEQ ID NO 23
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter construct YP0118 as found in Promoter Report #23
<220> FEATURE:
<221> NAME/KEY: misc_feature
<223> OTHER INFORMATION: T1 Mature Plant Expression: GFP expression observed in the Lateral vasculature (Lv) and Medial vasculature (Mv) of the carpels of the silique

<400> SEQUENCE: 23

| | | |
|---|---|---|
| aattgagaaa ggtgcctcaa tttcagtaga acctgacgca aaatttcgcg atcatgcatg | 60 |
| actcaaattg gtttattcac ttaaataaaa aagttgtttc cctatctagt tgaagttctc | 120 |
| aattcaaacg caacttctta ctttttcttt ttatttatac tggaatgaat ttttcgtcaa | 180 |
| tgctagacct caatatttgg tgattaagtc caaaaaatta tagcaatatt cattagttaa | 240 |
| atcataataa tatttgttat ttctgctaaa tatattagtt ttaaattggt aaatatatca | 300 |
| gtcatcatac tttatatatg tgcacaagaa aagaggaaa aaaactaac ttttaataaa | 360 |
| ttgaacgcta tcctctatat ctcgtcctgg tccaaatgta aacttcaata tccttttgat | 420 |
| tttattgctg attgctttaa aaaatttcac aaacactttt atcattcttt tattccacca | 480 |
| aaatctacag acataatact ttgtaatttt atgtaaaaat cttcaaaatt tgggaaaaga | 540 |
| aaaatcattt aaaatcaatt tgcattaact ggatttattt ccaaaggtgt ggtgttgtgt | 600 |
| ttatatatgt ggagttgttg gctagtaata taataaggaa aagagtgaaa catatgtagt | 660 |

-continued

```
ataacgtatt tctagttttt tttctctgta ttaatgaatc actaattaag tagtatgcat      720
taattgaatt atcagaagct ggtcacaaaa gtctaccaaa aaaacaaaa aaattggtcg       780 gaagaaaatg aaaataatga gaataaaaaa gggaaaaaaa ataagaagct agcaaacaaa      840
gcaattaaca tttcaaggca gttaattcat catgcaaggt gcttatgtgt gacaacgtca      900
tgcgttactt tttgcgtcta cactcatctc tctaacgcaa tccactaatt ctggtaatgg      960
attctgctat ttagaccaac cagtttcttc gtctctcaat c                         1001
```

<210> SEQ ID NO 24
<211> LENGTH: 1076
<212> TYPE: DNA
<213> ORGANISM: Arabidopsis thaliana
<220> FEATURE:
<221> NAME/KEY: misc_feature
<223> OTHER INFORMATION: Ceres Promoter construct YP0126 as found in
      Promoter Report #24
<220> FEATURE:
<221> NAME/KEY: misc_feature
<223> OTHER INFORMATION: T1 Mature Plant Expression: GFP expression
      observed in the Petal (Pe), Sepal (Se) and Silique (Si) of the
      flower, the Epidermis (Ep) and Vasculature (Vs) of the sepal, the
      Epidermis of the petal, the Mesophyll, Epidermis and Vasculature
      of the leaf
<220> FEATURE:
<221> NAME/KEY: misc_feature
<223> OTHER INFORMATION: T2 Seedling Expression: GFP expression observed
      in the Epidermis of the hypocotyl, the Epidermis (Ep), Mesophyll
      (Me), Cytoskeletal, Epidermal bodies

<400> SEQUENCE: 24

```
cattgtatct gagatgtgac tgtgaagaac aaagattcat gacatggtat tgttaagccg       60
cccatgtgga tgatcataac caaactctgt cctcagattt actcaacagt gtgtgtgaaa      120
caaaggctgg tttaagtatg aaaccggcac cacatatctc ttcttcttct gatcattctc      180
tcctacatag accgccatga atcctcttgg tgtcgacgat gattcccttc gaataatttg      240
cttagcaccc aagaaactcc tcaaaaaagc catattttcc cttatgtttt cctgaagctt      300
aaatgtttct tagtcttgga gaaagctttg agatttttaaa attggatctt ctttagtttg     360
tgaatctaaa ggggtttagt tacttggtat ataaacgaac gtatgaaaga aatgattaag      420 gattttttgag gtttttcttt ttaattacag agcacatggc tttgggttgt agatactaaa     480
ccaagaacaa atcaataaat ggtgtctgag aagttagtgt ctaatgatgt cctacatgat      540
aacttcattg gggcttattt gtctcaaaga catcacatgc ccaaatctct ctatagatta      600
tgtagggaca tgaagttgtg tacctaatga accacaagtc tctatcactg attaagtcat      660
accttcttct caatgatatt caaaagacag gaccacatga tttgattata tactgacaaa      720
gtcacaaaag ccttcaaaaa aattctgtgg caagaaagga aaatttgact agttatagtg      780
tctatctaac aaacaagtgg tcatattgat ttctatcttc acatcagaaa tcatgaagat      840
tgatcactat agggccctta cttatcatgc cgtggtccgg caaagccatg tgcttgcttg      900
ttggtgtaaa aatttatgag ctgaaacttt tgaaaccaat aaagggttat ctacaagtaa      960
tgttcttatc tatatatact catcactgac tcctttctgc tctgccattg cactgggatc     1020
caacaatgtc ctccgactcg tccaagatca agaggaagcg gaaccgcatc ccgctc        1076
```

<210> SEQ ID NO 25
<211> LENGTH: 1017
<212> TYPE: DNA
<213> ORGANISM: Arabidopsis thaliana
<220> FEATURE:

<221> NAME/KEY: misc_feature
<223> OTHER INFORMATION: Ceres Promoter construct YP0127 as found in
      Promoter Report #25
<220> FEATURE:
<221> NAME/KEY: misc_feature
<223> OTHER INFORMATION: T1 Mature Plant Expression: GFP expression
      observed in the inflorescence meristem, the Vasculature (Vs) of
      the sepal, the stamen, the Micropyle (Mp), Funiculus (Fn),
      Inner integuement and Chalaza (Ch) of the ovule
<220> FEATURE:
<221> NAME/KEY: misc_feature
<223> OTHER INFORMATION: T2 Seedling Expression: GFP expression observed
      in the Phloem (Ph) of the hypocotyl root(Rt) and Lateral root,
      the Phloem (Ph) of the root, the Phloem (Ph) of the
      lateral root, the Phloem and Pericycle of the lateral root initial
<220> FEATURE:
<221> NAME/KEY: misc_feature
<223> OTHER INFORMATION: T1 Mature plus: GFP expression observed in the
      Vasculature (Vs) of the silique
<220> FEATURE:
<221> NAME/KEY: misc_feature
<223> OTHER INFORMATION: T3 Seedling Expression: GFP expression observed
      in T2 Mature tissue expression (if different expression pattern),
      the Epidermis (Ep) of the cotyledon, the Hydathode (Hy)
      of the rosette leaf

<400> SEQUENCE: 25

```
tcagtgagtc gattggaacg tttaaagttg agacataacg cagtgatttc aaatttgtat      60
tagggtggtc ttattgtgtg tctagctact agctagagaa tactagaaga agaatacgta     120
gcaagatacg cataacattt ggtcctctct ttttttact ttcttttaac acattgtcct      180
cttatgattt gcttattgat ttcagtatct ttttgtatca ataattccct ccaaatgatt     240
aaaccctaaa aaaatgtgat tcattcacca cccgaagatt agcatcatca agtaacacac     300
aataactacc aataacctag ttttcatttt tctatactaa aatcctaaac atcccataaa     360
aatacaaaca actctgaacc aataatttcc tctaatccac gtgcacccca tcgtctcctg     420
acgtaagatt tgtctataac ttatcaaatc ccaaattcag ctttgttttc attatatagt     480
acgtactctt ataaaaaaga gaagagtaca catctttaat actttaactt aaaagaagaa     540
agtaatacta atataagagg agtctgagtc agcgacaagt gttcgcggag aaacggaaac     600
gctctctttc tctctcttcc cccaacgcca ataccttgg aatccctccc taactctgtc      660
ctgtcctttc gtcctcactt tctctctttt tacattttct acacaccaat aaaattgaaa     720
ccagcaactt ataaatcaac tcaagtttga attaatgatc gaaaaactag tttatttgtg     780
tcaatatgac ccattcttta ttcacataag tattttaact tttcaaaatg ttatctcaat     840
ctcctttgag tttctgtctt ccccataata aatttcaaat aattaataca catggttttt     900
taattagaaa taatggaaaa gaaaggacaa aggaataaaa aagaaacaca agttggcaca     960
ctctctttat tattcactcc cctctataaa tctcatacta tcttctctca tcttctt      1017
```

<210> SEQ ID NO 26
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter construct YP0128 as found in
      Promoter Report #26
<220> FEATURE:
<221> NAME/KEY: misc_feature
<223> OTHER INFORMATION: T1 Mature Plant Expression: GFP expression
      observed in the vasculature (Lv) and Medial vasculature (Mv) of
      the silique
<220> FEATURE:
<221> NAME/KEY: misc_feature
<223> OTHER INFORMATION: T2 Seedling Expression: GFP expression observed in the Epidermis of the root transition zone of the hypocotyl,the
Epidermis of the root specialization zone, the stipules,the
Epidermis,Atrichoblast and Trichoblast of the root differentiation
zone
<220> FEATURE:
<221> NAME/KEY: misc_feature
<223> OTHER INFORMATION: T3 Seedling Expression: GFP expression observed
in T2 Mature tissue expression (if different expression pattern),
the Epidermis (Ep) of the cotyledon, the Epidermis (Ep) and
Hydathode (Hy)

<400> SEQUENCE: 26
gataaactga taatggaaaa gaacaaagaa accagttttt aactatttgc atatgtaatt      60
tatttgttgc aaattatatt tagttaaaat gtttcctcta tttatatata tatatatcag     120
tcaagcacta tgtataagaa atgtcaattt ataaattttt acatgtcctt aacagaaag      180 aaaatgaatt tttacatgtc attcatagag agtcactcgt ttatttctta tatagagaat    240
aacacactca catgcatatg catgcaatat gatacatttt atgacaaaga taatcaacgg    300
aaacggtcaa gacataattt gataaacaac ttgcacgatg cacagatctg atcaaatata   360
taactcttta acatatccaa aatattcaaa aagaaaaact cgatccaaac tagcaacatc    420
acgctcacgc ggtaggctaa aaatttatta atctccaaaa gtctttctta tgaacactgc    480
aaacacaaca acttgaaaag tcatataggt ttagatgatg acgcgtattg gctatcgctt    540
accggagtgg ctcataaata caataaacaa tacgtaaaag tcaaagtcaa atatatttag    600
tcaactataa ccattaatcg ggcaaaacct ttagctgtca aaacaacgtg aaaacgatat   660
ttgtatatat catcaagaat cagtagataa gagaatgatt taatcccctg actattacaa   720
ttttggtgta ataaacagtc tctattggtt tttattcttt gttttaattt ctcatgacct    780
atagagagaa ttaggtagtt tcgaaaattg gctaatcaac ttttgaaaac tactgtctac    840
tttgcttaaa ttctctacac ttagtttcgg ataagataat tgtcggacta atagttaatc    900
ccttgacaat ctttgatatt ataaaaggtt tagttaatct cttctctata taaatattca    960
tacaccagct ttcaaaaata tataatccaa acaccaaaaa caaa                    1004

<210> SEQ ID NO 27
<211> LENGTH: 1081
<212> TYPE: DNA
<213> ORGANISM: Arabidopsis thaliana
<220> FEATURE:
<221> NAME/KEY: misc_feature
<223> OTHER INFORMATION: Ceres Promoter construct YP0020 as found in
Promoter Report #27
<220> FEATURE:
<221> NAME/KEY: misc_feature
<223> OTHER INFORMATION: T1 and T2 Mature, T2 and T3 Seedling
Expression: GFP expression observed in the Root Hair of the
hypocotyl, the Hydathode of the cotyledon adaxial surface, the
Epidermis, Mesophyll and Vascular of the cotyledon
<220> FEATURE:
<221> NAME/KEY: misc_feature
<223> OTHER INFORMATION: T1 and T2 Mature, T2 and T3 Seedling
Expression: GFP expression observed in the Hydathode and Guard
cells of the rosette leaf
<220> FEATURE:
<221> NAME/KEY: misc_feature
<223> OTHER INFORMATION: T3 Seedling Expression: GFP expression
observed in the Guard cell (Gc) of the flower, silique and
pedicle, in the Guard cell (Gc) and Vasculature (Vs) of the leaf

<400> SEQUENCE: 27
cagagcagtg catatttttt tttttttttt tttggtgtta gtgcatatct atatatatag      60
tactattata atatatttca atatatatat tttaagaaaa tatctgattc ttaagtttgg    120

```
acttatttgt caacaatagc cagtaaaaaa caaaagcgaa gtttcactaa cttaaaaaat      180
aaccacattt gtatatttcg aatacatact ataaattaat aaatttatca aaacaactat      240
agaaactgtt atttccaatc aatttcttta tcaagattat atctgaaata tatttattaa      300
aattaatagt tatttacaag aactatttt atgaaagtgt aagaactctc tgaaaacttg       360
ataagtcaat attttttcta acatcgtaaa cataaactag attcaaattc gaatctagtt      420
attcaaaaac ttataaaaac ataaaaatga aatactgtta cttcaacaaa aaacattat       480 tattattttg tttaaatatc taatttattc atcaacagca aaatatttaa aagagtggga      540
aacaaataaa aattaaactc tgttttggta tgataaaatt atttactaaa ctaaactcaa      600
tatattttta gtatcacggt tataactata acaataatcg aactttgtta ttttcttggt      660
actggtttta gtagtataga tagatatttt agtcataact cataagatac atgtacaaat      720
atttgctata tatgatcagt gataactgaa tttcgtgctg aaaattgcca tagtttgctt      780
attttactct tgaaacaata acgatatggt cgttacttaa aacaacattt taaaaacgaa      840
gaaaattaaa cagagtttgt taaaataaat taaataccat aaatttctct ttgactcttc      900
ctatatagta aaatctctca tccccttctc tctctctctc atagcatgtt ggtctttagg      960
ttcctatata aacaacgcca cacacaccca tttagtccca ccattgcact gggatccaac     1020
aatgtcctcc gactcgtcca agatcaagag gaagcggaac cgcatcccgt aaacgaagg     1080 c                                                                    1081

<210> SEQ ID NO 28
<211> LENGTH: 1091
<212> TYPE: DNA
<213> ORGANISM: Arabidopsis thaliana
<220> FEATURE:
<221> NAME/KEY: misc_feature
<223> OTHER INFORMATION: Ceres Promoter construct YP0022 as found in
      Promoter Report #28
<220> FEATURE:
<221> NAME/KEY: misc_feature
<223> OTHER INFORMATION: T1 Mature Plant Expression: GFP expression
      observed in the Vasculature (Vs) of the pre-fertilized and
      fertilized silique
<220> FEATURE:
<221> NAME/KEY: misc_feature
<223> OTHER INFORMATION: T3 Seedling Expression: GFP expression observed
      in the Epidermis (Ep), Phloem (Ph) and Root hair (Rh) of the
      hypocotyl root zone, the Epidermis (Ep) and Vasculature (Vs)
      of the petiole leaf
<220> FEATURE:
<221> NAME/KEY: misc_feature
<223> OTHER INFORMATION: T3 Seedling Expression: GFP expression observed
      in the Epidermis (Ep), Phloem (Ph) and Vascular bundle (Vb) of
      the Cotyledon (Co), the Phloem (Ph) of the Lateral root (Lr)
      and lateral root initial
<220> FEATURE:
<221> NAME/KEY: misc_feature
<223> OTHER INFORMATION: T3 Seedling Expression: GFP expression observed
      in the the Phloem (Ph) and Vascular bundle (Vb) of the Root (Rt)
<220> FEATURE:
<221> NAME/KEY: misc_feature
<223> OTHER INFORMATION: T2 Mature Plant Expression: GFP expression
      observed in the Vasculature (Vs) of the inflorescence meristem and
      silique, the Guard cell (Gc) of the pedicle, the Septum (Sp) of
      the silique

<400> SEQUENCE: 28
tagttccatt acaatttcca aatgatttgt tacaaagcta caagattatt cgaaatagga       60
tttcatccat aagagagaat ggtgtggtcg acgctacaat gttgatttat tggttgtggt      120
ttgcatcttg gggatgtcaa atcctaagtt tcaagttctt gtaaaaacgt tttcaggttt      180
```

-continued

```
ctttaatata ttttaatatt aatgtaaaaa gaaaagatat agcttttgta caaaaaaatt      240
tgtttaatca ctatgtagga ggatgcgatc aaattcatgg aatgatgtat tattagcttt      300
tctatcctca ctctaaaaac aatactatag tgagttaaat aatttgatca tttcaatgta      360
gattaaaatt ttattaaaag aagaaaaatt taaaagccta aacaaaata aaaaaggagg       420 ctcgaggtat gatgggtgta gcagaagagc tggcaacagc tatcgactga gtgattacga      480
actcagtact cagtgttctc agctcacaca ctcttttttt gttctctttc ttttggacag      540
ctttcatttt ctcttttctt ttttctattt tgtttcaaaa ttccatccat attaaaataa      600
gcctgatcat gagaataaag gaaatactaa tgatgagttt ctcaataatg caataagatg      660
caattattat gagctattta ctattgaaaa tgagcaaata aatgtcaaaa cacaatctgg      720
ttaagttaga gcaactccat tgtataggat tcatgtagtt tctaagaaaa caaaatgtat      780
taatatttta cttttacatc caaaaaacca aaaaaccaac ttatatgagt aatagaaacg      840
atcctcatat taggaatttt agagattttc tctcatctgt ttcttaactt ttcaatattt      900 ttatttttt aaattgtatg agtttctact aagaaactac tgctggagtt ggtcttagct       960
tcccaatgct tctccaccta tatatatgca tatctccttc ttaaaactcc attgcactgg     1020
gatccaacaa tgtcctccga ctcgtccaag atcaaggaga agcggaaccg catcccttat     1080
actaaaggcg g                                                         1091

<210> SEQ ID NO 29
<211> LENGTH: 1082
<212> TYPE: DNA
<213> ORGANISM: Arabidopsis thaliana
<220> FEATURE:
<221> NAME/KEY: misc_feature
<223> OTHER INFORMATION: Ceres Promoter construct YP0024 as found in
      Promoter Report #29
<220> FEATURE:
<221> NAME/KEY: misc_feature
<223> OTHER INFORMATION: T3 Seedling Expression: GFP expression observed
      in the Root hair of the hypoctyl root zone and the root, the Guard
      cells  of the leaf
<220> FEATURE:
<221> NAME/KEY: misc_feature
<223> OTHER INFORMATION: T2 Mature Plant Expression: GFP expression
      observed in the flower and silique
<220> FEATURE:
<221> NAME/KEY: misc_feature
<222> LOCATION: (1069)..(1069)
<223> OTHER INFORMATION: n is a, c, t, g, unknown, or other

<400> SEQUENCE: 29
tgttaaggga aggtttgcac ctaagaattt tgaaggaatt ttgcggcgat atatcagtaa       60
gtaactttct tctagtctc aaaatttaag ttgccataaa agtatatcag tttggagttg      120
ttaacctctt gttttattat ttctcagctg actacgtcat ttgccttggt tgcaagagcc      180
cagacaccat tctctccaag gagaaccgtc tcttctttct gagatgtgaa aaggtataag      240
ttaatctaat tagtcctgat cttgatatgc attcctttgt ttctgtttta cagttttact      300
ttctgcgcaa caaagtaata aagtattttg tgtgtttgaa tttgctaatg tgattaacga      360
gtgggctaca tggttttttgc agtgtggatc tcaacgatct gtggctccga tcaaaacagg     420
gtttgttgct cgtgttagtc gcaggaagac ttgagaaatt agaaggtgaa gtgaccttgg      480
tatggagttt ggagctattc tactgcttct gtatgagttt atgagttgaa gaaatacttg      540
tcttgttttt tttattttgt tttggaatat gattatgact tgactttaa aatgggatag       600 gatcaaaacc tttactctg tcaggttcat gtggtcacct tgaaggttga tttagtaaat       660
```

-continued

```
ccatggactt ctttttttgtg ttaagattat tcttagttca aaattaatag actaatgata      720
ttaacgtcca caggcattgc gttcaacatc tcaaattaaa gcgtggaagg ctcagaaagt      780
ccaatataca ctatgtttat ctacagttac aatcatacta caaaaaacaa ataatgtata      840
cggtttggtc taatatagcc gcatacgatt tagtatttac caacaaaaaa ttggtctcaa      900
accaaaccga acaattggta attaacaatt gttcttttgg tcttgaaccg aaccaaaccg      960
aactgaacta tattaaccga ccgacttcgt cctttcctcc ccattgcact gggatccaac     1020
aatgtcctcc gactcgtcca agatcaagag gaagcggaac cgcatcccnt taaacgaagg     1080
cg                                                                   1082

<210> SEQ ID NO 30
<211> LENGTH: 1031
<212> TYPE: DNA
<213> ORGANISM: Arabidopsis thaliana
<220> FEATURE:
<221> NAME/KEY: misc_feature
<223> OTHER INFORMATION: Ceres Promoter construct YP0028 as found in
      Promoter Report #30
<220> FEATURE:
<221> NAME/KEY: misc_feature
<223> OTHER INFORMATION: T3 Seedling Expression: GFP expression observed
      in the Root hair of the hypocotyl root zone, the Vasculature and
      Vascular bundle of the leaf, the Pericycle of the root and lateral
      root
<220> FEATURE:
<221> NAME/KEY: misc_feature
<223> OTHER INFORMATION: T2 Mature Plant Expression: GFP expression
      observed in T2 Mature tissue expression, the Ovule of the ovary
      and silique, the Funiculus of the ovule primordia, the
      pre-fertilized and fertilized ovule

<400> SEQUENCE: 30
gtcagtgaag tcgattggta gtacttgaaa cacttggttg gtttcatgta tttggcctat       60
atataaacaa acatcgtaat tatatacgga ttttttttcgg aattttacgc catatctgta      120
agtatatata acatgcatgt cgttttcaaa ttcatatgat gaacgatcca cgtaagtgct      180
actactccta caatattgca tgagagagat atgtatttat aaattttatt ttgaagaaga      240
aataagaggg aaggttactt gggtggatcg atgtgaaaac aaaagaagaa aaagcgaaac      300
ccactaagcc attacatgat atcgaccttc ttatcttttt cctctttatt ttatttttct      360
catcttcttt ttgtcaggac tttttttctac ttaatgaaac ctccaaacta tctaactaat      420
acactcccat gtagaataaa gaaaattata taagatattg ttgatatttt gtaactagaa      480
aatatatttg ctctgtaatt tttcgtaagt taaatcaaca ttttaaagta gaaacaaata      540
ttactgcaaa aagtaggatc attattttttg tccaaaatct cagttagcta tagggttgta      600
gtaaaaacaa aacacattct tgatttgccc caaaaaataa agagagagaa gaatattgtt      660
caaaagtggt ctcttctctc tctaattatg ttttcactaa acccaattag attcaaacag      720
tctacaaagt ccaaaagata aacatgggac aacaattcga tgcaaaaaat cctctttttca      780 tgctcttttt ttattctcta gtcttttaaa ttactaataa aaactcacaa atccaccaaa      840
cccattctct acaactcacc ttcatctaga tttaccccact cccaccgaga aacacaagaa      900
aaaaaatata catatataaa tatacaagac aacacatgat gctgatgcaa tatacacaac      960
aaagtattaa atcttagata ttgtgggtct ccctttcttc tattcatttt cttattcatt     1020
aaaaaaaaaa a                                                          1031

<210> SEQ ID NO 31
<211> LENGTH: 1075
```

```
<212> TYPE: DNA
<213> ORGANISM: Arabidopsis thaliana
<220> FEATURE:
<221> NAME/KEY: misc_feature
<223> OTHER INFORMATION: Ceres Promoter construct YP0030 as found in
      Promoter Report #31
<220> FEATURE:
<221> NAME/KEY: misc_feature
<223> OTHER INFORMATION: T3 Seedling Expression: GFP expression observed
      in the Epidermis and Root hair (Rh) of the hypocotyl root and root
<220> FEATURE:
<221> NAME/KEY: misc_feature
<223> OTHER INFORMATION: T2 Mature Plant Expression: GFP expression
      observed in the Guard cells of the flower

<400> SEQUENCE: 31
aggtcagtga agtcgattgg tacttgcctc atgtgtttgg atacgagatt actgaacgtt      60
gtggtgtatt ttatagtcat gggtttgtta attgttatca tgcttgccta cttaactagc     120
gtaattatgt tttttttgtac tacctcggaa gtagctattt tgtcgcttat tgacaacgag    180
atactttaag atgttccaca tccacgtcgt aatcggttga tcgaatggtg cctaatagat     240
caaagttatc ctcaacaaat atcgatgtgt agtatatacg tgaatatata gtagtctctt     300
gcatgcatat catatacaac ttaaatactc tttttgtttc aaaataaata atgttttagg     360
aaaaagatta ttgtgtcaaa ttaagtgttg gtctattcat ccaaacaaga aagaaaaaaa     420
atacgaattt gttttatata tcattgacga acaatgttta gctaataata aataattatt     480
tatttataaa aattaaaagt tagatagttt cttaatttag gtgcatataa gttcttttaac    540 aaaaaaaaca tttaggtgca taagtcttaa atatcaaata ttttggaaca gtaatttttat    600 gtataacttt tttcgtacct atcttcacac cgcataaatt gccaaagtca acctttgat     660 atttcattcc tcacaaaacc atattaattt atacacctca atattgttta atagtattat     720
catgttggct ttcgctgaat ttatcaaagt gcaacatgtt ttatcttaca aaaaaataaa    780
aagaaattca cgttgtgtga tcttgagagt tgacttttaa atatatcaca acttatataa     840
atacgcagca acattccaat ctctcaagaa aatctacagt tcctccaaat aataatacccc    900 tccctctaag gtttaaaact ataacctcatt aacacattaa gaagctagtc attacttcat    960
ttctatattt taaataatgt ttattgataa caattgcagg caactaattt tcagcaatca   1020
ccattgcact gggatccaac aatgtcctcc gactcgtcca agatcaagag gaagc         1075

<210> SEQ ID NO 32
<211> LENGTH: 1106
<212> TYPE: DNA
<213> ORGANISM: Arabidopsis thaliana
<220> FEATURE:
<221> NAME/KEY: misc_feature
<223> OTHER INFORMATION: Ceres Promoter construct YP0054 as found in
      Promoter Report #32
<220> FEATURE:
<221> NAME/KEY: misc_feature
<223> OTHER INFORMATION: T3 Seedling Expression: GFP expression observed
      in the Epidermis of the hypocotyl root zone and cotyledon, the
      Epidermis and Vascular bundle of the root differentiation zone
<220> FEATURE:
<221> NAME/KEY: misc_feature
<223> OTHER INFORMATION: T3 Seedling Expression: GFP expression observed
      in the seedling root and root tip
<220> FEATURE:
<221> NAME/KEY: misc_feature
<222> LOCATION: (1094)..(1094)
<223> OTHER INFORMATION: n is a, c, t, g, unknown, or other

<400> SEQUENCE: 32
ctgatctcta gtccagtcga ttggagctta ttttgttcta ttctatcgta tttgattctt     60
```

```
ctttcgtttt ttttttgttt gacttaagaa accgattgtt tatagtagta aacatttgtt    120
tttaatgttg ctcgattcca gtgcacatgt ccaggctaga cacttgtcgt tataaaggtt    180
gctttggttc aatattgatc cactagagat gttacaacta ttgttgacat ctgagattgt    240
gtgataagaa aatatgaaac tggatttagt gaaagttaca atatataatc atacatcata    300
gataggaaat aaggaaatgt cagatatact tgaagaatac atcaaataga caaggtcctt    360
tttcttattg tcgactatta tagagccgta cagaaccttt tcacgtcttt agtaattagt    420
acattctcca tttcggctct ctcttatttt ttttccatct cttttactt ctccaaataa     480 taacaataaa agcttcgatt ttgtgtgtgt ttgtatttac atcttgacat cgatattctt    540
ttcatcaatt tttaccaaa aatgtaataa aaacaaaaaa aaaccaacgc tgaacacaga     600
catggtttct ccatccgttt atattcatcg tttgtatgtt tacttaacaa cttatttcaa    660
aatagtacat atcatggttg tgtttttaaa aaaagtatac agaacagaaa agcacatggt    720
agacaaaata atgaagccaa aattaataca agaagaagt tcaacttgta tttattaaca     780
cattttcttt ccttgtcaaa gacatgcaaa ttggttttgt tttcttattc ccatttttt     840 tttataataa aaagaagaag agtaaaacaa aaaaactatc atttcttctt atcgcaaaac    900
tcttatctaa gcaagaaacc gacaaaacct atatctacat atattctcat caacatctct    960
tgagacatat tcattttggt taaagcaaaa gattttaaga gagaaagggg gagaagtgag   1020
agagaccatt gcactgggat ccaacaatgt cctccgactc gtccaagatc aagaggaagc   1080
ggaaccgcat cccnttaacg aaggcg                                        1106

<210> SEQ ID NO 33
<211> LENGTH: 1017
<212> TYPE: DNA
<213> ORGANISM: Arabidopsis thaliana
<220> FEATURE:
<221> NAME/KEY: misc_feature
<223> OTHER INFORMATION: Ceres Promoter construct YP0025 as found in
      Promoter Report #33
<220> FEATURE:
<221> NAME/KEY: misc_feature
<223> OTHER INFORMATION: T3 Seedling Expression: GFP expression observed
      in the Guard cell (Gc) in the leaf
<220> FEATURE:
<221> NAME/KEY: misc_feature
<223> OTHER INFORMATION: T2 Mature Plant Expression: GFP expression
      observed in T2 Mature tissue expression (if different expression
      pattern), the Guard cell (Gc) of the leaf and stem

<400> SEQUENCE: 33
gtcagtgaag tcgattgggt ctcaccatga gccaatgaaa agaaatagta atccaggtga     60
ttgtttctct ttgatgtctc actttctaat agctagtctc taaaagaacc tttgttttag    120
tgaattctaa tatagtaggg gttttgcagc gcaattttct tcagcaccga agaaaagtag    180
attgaagatc ggagagtcct ctgctttctt tacatatgtc aaatctactg tccttagaac    240
taacggtcag gatcctcctc ttgtcgatgg aaatggctca cttcatcttc atcggggttt    300
ggcggagaag tttcaagtgg tggctagtga agggatcaac aacaccaaac aagcacgcag    360
agcaacacca aaatctactg tccttagaac taacggtcag gatcctcctc ttgtcaatgg    420
aaatggctca catcatcttc atcggggtgc ggcggaaaag tttcaagtgg tggctagtga    480
agggatcaac aacaccaaac aagcacacag aagtagaggg accgagcaat accattctca    540
aggagagacc ttgcagaatg gcgccagcta tccacattcc cttgagcggt cacgcacgct    600
tcccacatca atggaatctc atggtaggaa ctaccaagag ggcaatatga atattcccca    660
```

-continued

```
agttgctatg aacagaagta aagattcgtc tcaagttgat ggatcgggtt tctctgcacc      720
aaatgcctat ccttactata tgcatggggt catgaaccaa gttatgatgc aatcagcagc      780
catgatgcct caatatggtc atcaaattcc tcattgccaa ccaaatcatc cgaatggaat      840
gacgggatat ccttactacc accacccaat gaacacatct ttgcagcata gtcagatgtc      900
tttacagaat ggtcagatgt ctatggttca tcattcttgg tcaccggcag gaaatccgcc      960
ttctaatgag gtgagggtaa ataaacttga cagaagagag gaagctctgc tgaaatt       1017
```

<210> SEQ ID NO 34
<211> LENGTH: 1026
<212> TYPE: DNA
<213> ORGANISM: Arabidopsis thaliana
<220> FEATURE:
<221> NAME/KEY: misc_feature
<223> OTHER INFORMATION: Ceres Promoter construct YP0050 as found in
      Promoter Report #34
<220> FEATURE:
<221> NAME/KEY: misc_feature
<223> OTHER INFORMATION: T1 Mature Plant Expression: GFP expression
      observed in the Sepal, the Carpel (Ca) and Style (Sy) in the
      silique, the Epidermis (Ep) and Mesophyll (Me) of the leaf
<220> FEATURE:
<221> NAME/KEY: misc_feature
<223> OTHER INFORMATION: T2 Seedling Expression: GFP expression observed
      in the Epidermis, Root hair (Rh), Root (Rt) and Vasculature (Vs)
      of the hypocotyl root zone, the Epidermis (Ep) and Vasculature
      (Vs) of the hypocotyl, the Epidermis (Ep) and Mesophyll (Me) in
      the cotyledon
<220> FEATURE:
<221> NAME/KEY: misc_feature
<223> OTHER INFORMATION: T2 Seedling Expression: GFP expression observed
      in the Guard cell, Epidermis (Ep) and Mesophyll (Me) in the
      primary leaf, the Epidermis, Cortex (Cr) and Phloem (Ph) in the
      lateral root, the lateral root tip the primary Root cap (Rc)
<220> FEATURE:
<221> NAME/KEY: misc_feature
<223> OTHER INFORMATION: T2 Mature Plant Expression: GFP expression
      observed in T2 Mature tissue expressions similar to T1 expression
      plus, the immature flower, the sepal and the silique pedicle,
      the Cortex (Cr), Endodermis (Ed) and Epidermis (Ep) in the stem
<220> FEATURE:
<221> NAME/KEY: misc_feature
<223> OTHER INFORMATION: T3 Seedling Expression: GFP expression observed
      in T3 Seedling tissue expressions similar to T2 seedling
      expression, the root, the Epidermis of the cotyledon, the rosette
      leaf, the root cap

<400> SEQUENCE: 34

```
aatctgatct ctagtccagt cgattggtac ttgagggaaa catcatattt ttaaaccttg       60
tctcagtaag ctaacacaca ccccttgtga ttacttatcc atgtttatcc acaagaatgc      120
agttggattg agatattttc ttctttgttg aaatcaggcc tcaaggtgtt catgtggtct      180
gcaaaaaaat tcccaaaaat aaagatagtg acatctgaaa tcgataatgg attagacgaa      240
gagtttcgtg ttattccttg gtatgggcgg gtttggggac agatattttg gcacagacga      300
ggactaggcc actgtggtcc tgcagcatta ggtgtcccct ccatgtcctg cattacattt      360
tattgatgga ttcatcaccc tatctactac aacggctaca caaactatga agagttttgt      420
ttactaataa atgcccaagt gaggggtcga tcgaacccgg gacacgtttt tcagtttacc      480
atatagaatt atccttggaa cccttgatac tccatagaac atcaccacct ctgttgtcat      540
ctcaggaatc caggttcaaa cctagtctct ctctccctag tgggaggtat atggccactg      600
ggccaatgat gacaaaatgc aaaaaaaata aaatacattt gggttcatta tctaaaatat      660
ctcttgtgtt tgtaagtttt ggttgcacac tcgtgtggtt gaagtgtgtg tgagaggtac      720
```

```
tatacaatac actctgcttt tgttttgtac ctatctcttt ctcttctcca catatccaag      780
actttgggga taaagctgag atcattggtt gccatttggt tgtgtagaag caatcaccca      840
tttgctttat ccgaggttga taaatttcct cgggttctcc ttctgacacg tatgacaaat      900
tctaatagta tattcctcgt agatattacc tatatattct caatagttgc aggtacttaa      960
ggctttgtct tggcatcctc gtcctcttca gcaaaactcg tctctcttgc actccaaaaa     1020
gcaacc                                                                1026
```

```
<210> SEQ ID NO 35
<211> LENGTH: 1087
<212> TYPE: DNA
<213> ORGANISM: Arabidopsis thaliana
<220> FEATURE:
<221> NAME/KEY: misc_feature
<223> OTHER INFORMATION: Ceres Promoter construct YP0040 as found in
      Promoter Report #35
<220> FEATURE:
<221> NAME/KEY: misc_feature
<223> OTHER INFORMATION: T3 Seedling Expression: GFP expression observed
      in the Phloem and Epidermis (Ep) of the hypocotyl, the Phloem (Ph)
      of the hypocotyl root zone, the Phloem (Ph) of the petiole,
      cotyledon and root, the Pericycle (Pr) of the root
<220> FEATURE:
<221> NAME/KEY: misc_feature
<223> OTHER INFORMATION: T2 Mature Plant Expression: GFP expression
      observed in T2 Mature tissue expression (if different expression
      pattern), the Epidermis (Ep) and Vasculature(Vs) of the
      inflorescence meristem
<220> FEATURE:
<221> NAME/KEY: misc_feature
<223> OTHER INFORMATION: T2 Mature Plant Expression: GFP expression
      observed in the Pollen, the Epidermis, Guard cell and Cortex of
      the stem
<220> FEATURE:
<221> NAME/KEY: misc_feature
<222> LOCATION: (1077)..(1077)
<223> OTHER INFORMATION: n is a, c, t, g, unknown, or other

<400> SEQUENCE: 35
cccatcacat gtaacatcat tgggctatcc aaaagtctaa ccataatgt caatctataa        60 accacattaa gtagttcatt ttttttgtag tcgtgtttag cttgttaaac ctcataaaat      120
atgttttcac ttacgttaac aaaacaaata tcttcacgaa aaaaaataaa ataaaatatc      180
tttttgatac cgaaaaaata aaataaaata aaataatttt ccctttcgat cataaaatgc      240
gtagataaga gaaactgtgt ttgaggctcc atttcatgtt cacctaccag tctaccacgt      300
catttctcaa agacgcaaat tttctaatta gggatgtgct cttttacat atagatcaat      360 atcctaaaaa aatttaagat attcatattt tcgtacatat atatcgagtt tcccgaaaaa      420
tccataaaaa gggtataatg atagtccttt ttctcctta ataataattt ctgaacaaaa      480
ttatatcata ataaacttgt gattttatac aaaatttatt tgtatatata attttactaa      540
acaacgtgaa cgataaaaat aatattctca taaatgttg attaaaaatt acttaaaata      600
aataattatt taggattatg tattagtagt actcgaacca tttttttagt tatctgcatg      660
aagaccctaa tttttcacat atatcgaaac taaaactttg gatatacact gtaatttgaa      720
aacgcttgga acggataatg tagttacctc acaagatttt gtacatccct gacattttat      780
attcattaaa gtgtgttttt ttcttcagaa aagaaaacac ttttttcttt tgtgcttta      840 gtttaaatta acaaaaaaat ggacaccatg agattccact aactcatgtg tatataacat      900
tagggaagca gtcaattcat ttcagcatcc acacacactt tgaatgctca atcaaagctt      960
cttcatagtt aaacttcctc acaacgtcaa aactcgagaa gaagaccatt gcactgggat     1020
```

-continued

```
ccaacaatgt cctccgactc gtccaagatc aagaggaagc ggaaccgcat cccttttnaac    1080 gaaggcg                                                               1087
```

<210> SEQ ID NO 36
<211> LENGTH: 1071
<212> TYPE: DNA
<213> ORGANISM: Arabidopsis thaliana
<220> FEATURE:
<221> NAME/KEY: misc_feature
<223> OTHER INFORMATION: Ceres Promoter construct YP0041 as found in
      Promoter Report #36
<220> FEATURE:
<221> NAME/KEY: misc_feature
<223> OTHER INFORMATION: T1 Mature Plant Expression: GFP expression
      observed in the vasculature (Vs) and Guard Cells (Gc) of the tem
      and flower
<220> FEATURE:
<221> NAME/KEY: misc_feature
<223> OTHER INFORMATION: T2 Seedling Expression: GFP expression
      observed in the Guard cell (Gc) of the petiole, cotyledon and leaf
<220> FEATURE:
<221> NAME/KEY: misc_feature
<223> OTHER INFORMATION: T2 Mature Plant Expression: GFP expression
      observed in the developing flower and pedicle
<220> FEATURE:
<221> NAME/KEY: misc_feature
<223> OTHER INFORMATION: T3 Seedling Expression: GFP expression observed
      in T3 Seedling tissue expressions similar to T2 seedling
      expression

<400> SEQUENCE: 36

```
gggatgcggt tccgcttcct cttgatcttg gacgagtcgg aggacattgt tggatcccag      60
tgcaatggtg caacatcgaa tccaaattct cttaacatca taacacagac taaaatttca    120
ggctttcgtg ttaaaagaga gaatatcatt gaacttttc tcttaccttc atgattcctg     180
caagaacagc acctccgagg tataccatgt gtttccttct cggtggatct tcgatccgca    240
atctgagttt ctgattgata agaaaaacga agataaatgt taaaagctga gctaatgact    300
gacagtgatc atggcattat cagaattatc tttttacct tcaagccatc tttgtttcct     360
tttagaactg tgtcgagata ccgatcctgt atttctttct caagactaga acaaacaga     420 gaataaaaga cattgaaaca taaacaatg gaacttcttg ctgggtttat gataaacaaa     480
aaatatacga accggctagg taatcctggg tacatggtgc tacctccgct taaaactatg     540
tgttggtaga gctgtgaaaa aagagcaaag ggtttaagac agatacatga ttagttttgt    600
tggatctgtc ttttgaaata ccaagcaagc gtaagagtca cacgtaccat catgcggtta    660
tcaatatcca tttcttgaat acatcggaaa accatgtctg ccattccatc accttcaaca    720
tcaatgagtt cctgaaaaaa tatttggttg tgatcagcct cgagattctt ggagggttga    780
aactattcca aaagagaaat tagcagagga cgcgatgaag gttaccggaa gtaaaaagcg    840
cttcaggtgc ttggaatctt tcagtgccta ctttgataac cctcccatct ggaagctgat    900
cacagttcaa aaacacaacg ggttagtact ctggaaaaaa ataatttggg tgataatatc    960
agctttagag gctgcaactg gcacaagtat gaaactttat cgactatcgg atgaaaaatc   1020
ccaaacacag cgcccaagaa cagagaaacg atgtcatgaa aagaaaagat g            1071
```

<210> SEQ ID NO 37
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0056 as found in
      Promoter Report #37

<220> FEATURE:
<221> NAME/KEY: misc_feature
<223> OTHER INFORMATION: T2 Mature Plant Expression: GFP expression
      observed in the Guard cell (Gc) of the stem and pedicel, the
      Vascular (Vs) of the leaf
<220> FEATURE:
<221> NAME/KEY: misc_feature
<223> OTHER INFORMATION: T3 Seedling Expression: GFP expression observed
      in the Root hair (Rh) of the hypocotyl, the Epidermis (Ep) and
      Mesophyll (Me) of the cotyledon, the Vasculature (Vs)
      of the cotyledon
<220> FEATURE:
<221> NAME/KEY: misc_feature
<223> OTHER INFORMATION: T2 Mature Plant Expression: GFP expression
      observed in the inflorescence meristem
<220> FEATURE:
<221> NAME/KEY: misc_feature
<223> OTHER INFORMATION: T3 Seedling Expression: GFP expression observed
      in the Cotyledon (Co) and Root hair (Rh)

<400> SEQUENCE: 37
ataggaatct gcttcggtag aagattcgag agaggagagg aagcatcggt ggttttggag      60
ttccttattc ttctcttctt tccaaagttt tgtcattcgc caagattcct taaaaacttg     120
ttcacacatc ataattatgc accaataggt tataaatcat aatccaacaa gttagtcatt     180
ggctttaatt ttaaaaaatc ccataagagt aaaatctttt agaaagttaa tcaacccaca     240
catgggctag aaaccaaaa accccacgaa cattgagatt acaagaaaca ttttttaagtc     300 ctaaatgagc ccaagagcat tgcttaatga agaagaactg atattaatta actaatatta     360
ggacacataa aaaaatacga aaacaccaat cttcatgcca caaatcaaa caaaaacgaa      420 aaaatcaatt ttcatgaaat ggataaagag agagcgtaat tatcaggaat ttgattgagt    480
acggttgtta tgatgatcat tcacaattat ctttgatctt gagatttagc aatagttaat    540
tttcggatgt ttttttgtta cttgctgctc acttcttgta tgcagattaa tttataagag    600
agaccagtta caactctttc ttatttgaat aagattttat aagatgtagt gtggccatgt    660
gggtttattg catgcagctc tctgcgttgg tcccaagtcc acgacaatag agagtttctg    720
cacttcacgg tatcgtcgtc gtcacaagtt ctttaccta tcattggcac aagttagcca    780
ccgtctttgc gcaagttagc atgttgtgct acatacgtgt catgaactga ttggtcaaat    840
ttggatatat tttattcccg tcggttatgt ttggataaaa atataaaacg gaaatttctg    900
tttcagcctt ccttggtccc aaagaaaaat acgcacacct actcccttca ttctctatcc    960
tctccactca taatatat atctaaatgc aatctctcc                             999

<210> SEQ ID NO 38
<211> LENGTH: 1080
<212> TYPE: DNA
<213> ORGANISM: Arabidopsis thaliana
<220> FEATURE:
<221> NAME/KEY: misc_feature
<223> OTHER INFORMATION: Ceres Promoter construct YP0068 as found in
      Promoter Report #38
<220> FEATURE:
<221> NAME/KEY: misc_feature
<223> OTHER INFORMATION: T2 Seedling Expression: GFP expression
      observed in the collet root hairs only of the hypocotyl root zone

<400> SEQUENCE: 38
aaattgggga gtggggagat gtttggttat attcccttct catcgatggt ctagatgtgc      60
gaggtgactc tcatggaggt aaagaacaat ggtgatttg tgaagaaccc aacgtaatgg      120
taattcctaa aaaggttaga agttttttca gcttgttgta ttgctaaaat ggggttgatg     180
tactcaacga catccaagtg tacttgagtg agcttttttg gggttgagta cctcgaccca     240

-continued

```
ttattcaaac taatgtaaat ggtgaatgca gcagtgactt tgttgccttt tgcaagaact        300
aaagaagaca gaaacaggtt gtaaaagaga gccaagtgtg tgtttatggt agaaagagca        360
aagtgaacga aaggtgtacc ttttttgactt gttgtcactg gttttctccc acttcatccg       420
tttcatgctg catcagaaaa caacataaga aatgaatgac gtaacgcgaa gcattaggag        480
ttgcttgtaa attaatacat tgccattact aacgtaattc agtagattct aactacaaat       540
gaagtcaatg tatctatctg tctactttag ccaatgtatg ataagaccaa atagtcttct       600
cttttttcag aaactctcta ggattaaaaa gtttgtgggt gaaagaaata ttatcgtgtg        660
gatgataaga ataattgatc ttgtgttagt aaattaggaa tagatataca agtaggtttc       720
tctctaaata aaaaataaaa gagtttaaat tgcatgcgta taaagaaaaa aagtaagaag       780
aaaatatgtt ccggttaatg gttgggtgca tccgaatcga accggcgcaa accaaaaaat       840
ctaaaggaga tttgaggtga taaaggaaa tcagacattg aaccaaaaaa acaaaagcga       900
gacggtggaa agaaaaaact ggaaaagaca gttttagccc ctcctaaaag caaagaaaaa     960
aaagataata aatagcttcg tcgtcgtgat cgacctctgc cattgcactg ggatccaaca       1020
atgtcctccg actcgtccaa gatcaagagg aagcggaacc gcatcccgtt aaacgaaggc       1080
```

<210> SEQ ID NO 39
<211> LENGTH: 1070
<212> TYPE: DNA
<213> ORGANISM: Arabidopsis thaliana
<220> FEATURE:
<221> NAME/KEY: misc_feature
<223> OTHER INFORMATION: Ceres Promoter construct YP0082 as found in
      Promoter Report #39
<220> FEATURE:
<221> NAME/KEY: misc_feature
<223> OTHER INFORMATION: T3 Seedling Expression: GFP expression observed
      in the Root hair (Rh) of the Root (Rt)

<400> SEQUENCE: 39

```
aagggatgcg gttccgcttc ctcttgatct tggacgagtc ggaggacatt gttggatccc        60
agtgcaatgg tttgtagaga aacaggaagc tttgttgaga aagttttaac agtgagttta      120
gtatttatct gagaactgtg tgcgacgaaa ctggagacag gggaggacta tatacaggag      180
ttaagtgttg aaggtgggat attgtcagtg agtgaatgtt ctggagaagt ggggagattg       240
atatttctct ggatgtttct agagatccgt ggctcccaag ctaagtgaaa caaatataaa       300
ttgtcttgtt tattaacggg ctacggccca tcggtattag gcctgtttta gtagatttat       360
ggtcaacaag tcaaatgacc ctagaacatg gtacatgaat gaaaaggacc aaaatgtgga       420
cagaaatcaa ccaaaggccg aggcggccac caaccaccga acgtgggaag gtctggttcg       480
ggcaaacatt cgaaaagacc aagaagactc ggataaacaa ttaaaaaaat cagatattgg     540
ggaaggcaaa tatatattgg tgttgaggtc aagacttaga gttttgacgt tattttaaaa     600
aaaatatttt tgggtaaaga ccaaagagtt tgacgctatc ttgaggttta tttattcaac       660
gtagactata tactatgggg ccgttctgaa ttggaccttt taagttttga ttttattaaa       720
acgccatgtt gtttagtcga gagataaaca aaagacgtgt ctctagctaa gctgaccttc        780
atatatgctt tgacataata cattaattat aatctctctt tttggtgtgt gtaaaaaata       840
cactctatat tttattatgt agacacacta catgcagaag tgttcttacc tctgcctcta       900
cgtgctgtca actcctacag atcttcaagt accccaaccg ttatctaaca gattaaatat       960
aatatacccc taactatatt atatatcaca attgttcaaa ccagtgtata tagactagac       1020
```

-continued gattccttga accatataat tccagcttta ctataagagt cttaaggaca        1070

<210> SEQ ID NO 40
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0019 as found in
      Promoter Report #40
<220> FEATURE:
<221> NAME/KEY: misc_feature
<223> OTHER INFORMATION: T2 Seedling Expression: GFP expression observed
      in the Epidermis and Root hair (Rh) of the hypocotyl root
      transition zone

<400> SEQUENCE: 40
ttacgcggcg ctacactctt atcaaagttt gaagattttt caagagacac aacagattca        60
agattttctg gtggctaaac ttacaatgac agtacatgga ggatctccgc gaatggaytt       120
ctgcaatgta ctagcgtaga acaaacactt tttgttaaag tcatcaacca acatagcata      180
gagttgttta tctgaacaga acactgaaag tcttggtttt gtttgtgttc cagtaaactg      240
tgtcaaaatg aaagaaaata cttattaaca agttcggcaa aaaaaattca aacttttgtg      300
cattattata tgaaagcact tctagaaagc taccttcttc ctgctcctcc tgttcctagt      360
tttcggactc tccactcgag tgttccctct cgcttcaatc acaaacggct ttactacaga      420
catagctgat aaaagggtcg aaaaatcatg aaccaagtaa gcgaaacaga ggataataaa      480 catgaagaa gaacagagta agacgaatta taccactcac ttgttattcg aattggaaac       540
tggggataag gtttcaaacg agttccgaga atgtcagaga ctctaaactg aacagtagaa      600
agagaagtca aagcagccat gccaagtatc attcgtaaag catcgaaagt cagaacatta     660
ccctcagcgg aatttaatca aacaccttct gtgcaggaat aatctctggg ggttttatca     720
acactcaaaa aaaactggaa ctttgtaaat aaaattataa atgttcgtac ctttatgcaa     780
aatttctcac agcgtaatta tctatttcct ttttgtcctt tatgaaagag gataaggttt     840
ttaaataata aatactaaat tgtttttaaa agaaactaaa aataaatgga aagccttaag     900
cgtcgtcaat ggttctagag tcttctgcaa cttttctttc atgaaactac tgtaatcttc     960
tgctaacata tataatctca aacactatct tctccaatt                             999

<210> SEQ ID NO 41
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0084 as found in
      Promoter Report #41
<220> FEATURE:
<221> NAME/KEY: misc_feature
<223> OTHER INFORMATION: T2 Seedling Expression: GFP expression observed
      in the Guard cells of the cotyledon, petiole and rosette leaf
<220> FEATURE:
<221> NAME/KEY: misc_feature
<223> OTHER INFORMATION: T3 Seedling Expression: GFP expression observed
      in T3 Seedling tissue expressions similar to T2 seedling
      expression, the Guard cells (Gc) of the cotyledon

<400> SEQUENCE: 41
gatataagta gaatcatttt ttgccgccgt ttctcgctaa cacaccgaaa actgaatcaa        60
atctcctagc tcttctacgc aaaatcgagt gcatcgacaa tggcggaacg tggtgtcgaa       120
cgtggtggag atcgcggcga tttcggacgt ggattcggtg gtcgcggcgg tggaagaggt      180

```
ggtccgagag gtcgtggtcg ccgtgcaggt cgtgctccag aggaggagaa atgggtgcca      240
gtgactaagc ttggtcgtct cgtaaaggaa ggtaagatca caaagattga gcagatctac      300
ctccattctc tcccagtcaa ggagtaccag atcatagatt tactcgtcgg tccttcattg      360
aaagacgaag tgatgaaaat catgccggtt caaaaacaaa ccagagccgg tcagagaacg      420
agattcaagg ccttcatcgt cgtcggagat agtaacggtc acgtcggatt aggagtcaaa      480
tgctccaagg aagttgcgac ggcgatcaga ggcgcgatca ttctcgcgaa attgtctgtg      540
gttccgatac gaagaggtta ttggggtaac aagattggaa aaccacatac ggttccgtgt      600
aaggtaaccg ggaaatgtgg atctgttact gtacgtatgg ttccagctcc gagaggttct      660
ggtattgtgg cggctagagt tcctaagaag gttcttcaat tcgctggaat tgatgatgtc      720
tttacttctt ctagaggatc caccaaaact cttggaaact tcgtcaaggt atgtactttc      780
acaatggctg ttttggtttg atgaactctg aattaggcag tgaaaaagta atcattacca      840
gttaagtgaa tttatattga agattaggat ttagctgatt gtattggttt gagcatgtga      900
gtttgtgttt aagattgctt gaattgaaat gctttaggtt gtttgattac gctaaattct      960
gactaatgta attcaaattg ttgttgtttt tttttggtc                              999
```

<210> SEQ ID NO 42
<211> LENGTH: 1015
<212> TYPE: DNA
<213> ORGANISM: Arabidopsis thaliana
<220> FEATURE:
<221> NAME/KEY: misc_feature
<223> OTHER INFORMATION: Ceres Promoter construct YP0087 as found in
      Promoter Report #42
<220> FEATURE:
<221> NAME/KEY: misc_feature
<223> OTHER INFORMATION: T2 Seedling Expression: GFP expression observed
      in the Pholem of the hypocotyl root transition zone and the
      root differentiation zone
<220> FEATURE:
<221> NAME/KEY: misc_feature
<223> OTHER INFORMATION: T2 Mature Plant Expression: GFP expression
      observed in T2 Mature tissue expression (if different expression
      pattern), the Recpetacle (Re), Silique (Si) and Vasculature (Vs)
      of the flower, the vascular bundle of the stem
<220> FEATURE:
<221> NAME/KEY: misc_feature
<223> OTHER INFORMATION: T3 Seedling Expression:T3 Seedling tissue
      expressions are similar to T2 seedling expression

<400> SEQUENCE: 42

```
tgaattgagt aaaatgtgtt ttcaaacagt taggtggtag aaggtaaagg taataacatc       60
atgatcttac taaagaatt gttgcatact aactatcaat attctcaaca acataatata      120
atgttttttt aggtaatttt ccattttaat tttttgtgat taaacaatta aacaactcga      180
atgatgatga taaaaaaaaa aaattaacaa ctcgaataag ttaaagtagc aatacacatg      240
tcgttcaatt caaccaataa agtaagactt atattttaa gaagttgact aatagcttaa      300
taagttggaa aacttgtgta gtttcttaat tcccacgtgc agtaagaaat aaaaatgaaa      360
aaaattatta tatccttccc actctgcgac ttttctttta ttttatcaaa tattaaaaag      420
attcaaaaat agataaactc atatcacagt ttacacattg aaatcataaa cgataattat      480 gtatttgta ataaaagtt agttctgaag ctcatacttt ggatagtcgc tagtcgctaa      540
tatgctcctt gtaataatta aagtcactac gacgcacgtc aaagccgata tttagggctt      600
aattgatgcg tgtttttctt ttcatataat agtaatataa attagtacta ataaagtatg      660
atggatggtt gagacagaaa agaaaaaaga tgactgtatg gtcatcatta caaagaagaa      720
```

-continued

```
tgtattcttc atgttcttaa gaataataaa atgtcacttg taaatcaagt tggtaagcat      780
tttgagaact tgttcgatg caacgtatga tgatttatgt agacaaaaga taaaaccgta      840
tcttcaacta ttgccaagaa aagataaaac ctaatctagt cagtctctca acataaatac      900
aacccaatag ccaaactgtg tccaattcgg agagaaacta aactaaaaca aaacacaaaa      960
gcccaacata agcccaataa aacccatttt ataaacagaa cattactaac actca         1015
```

<210> SEQ ID NO 43
<211> LENGTH: 1091
<212> TYPE: DNA
<213> ORGANISM: Arabidopsis thaliana
<220> FEATURE:
<221> NAME/KEY: misc_feature
<223> OTHER INFORMATION: Ceres Promoter construct YP0180 as found in
      Promoter Report #43
<220> FEATURE:
<221> NAME/KEY: misc_feature
<223> OTHER INFORMATION: T1 Mature Plant Expression: GFP expression
      observed in the Petal in the developing flower, the Locules (Lo),
      Pollen (Po), Silique and Tapetum ameboid (Tp)
<220> FEATURE:
<221> NAME/KEY: misc_feature
<223> OTHER INFORMATION: T2 Seedling Expression: GFP expression observed
      in the Epidermis and Guard cells (Gc) of the hypocotyl, the Guard
      cells of the petiole, the Phloem (Ph) in the root differentiation
      zone
<220> FEATURE:
<221> NAME/KEY: misc_feature
<223> OTHER INFORMATION: T2 Mature Plant Expression: GFP expression
      observed in the Epidermis (Ep) of the pedicle and stem
<220> FEATURE:
<221> NAME/KEY: misc_feature
<223> OTHER INFORMATION: T3 Seedling Expression: GFP expression observed
      in T2 Mature tissue expression (if different expression pattern),
      the Epidermis (Ep) of the cotyledon

<400> SEQUENCE: 43

```
caatctgatc tctagtgcca gtcgattggt tattgttgaa acggatggta tccagattca       60
tagagttata cgttgttgac ctcgtacagg atgaattcat tatcttcttc ttcttttgca      120
gcatggcagg tgatcgatgg gtatgacttg tgatgatagc catgtccacc aaatcagcca      180
agaaaagatc aagacctcgg ctgcttacgt tctgttctat aaacgccttg tagactaaag      240
aaactgaagc ggaaaagaca agaaagaggt atttgcattt ttgccgggtt tggcttattt      300
aaaaacatca ttggcttgat tctaattcac tacaagatca agatgaaagc agctctgcgt      360
tgaggctaat ttacagaaga gagagagaga gttgggaaga agagcaaaag accgagagga      420
catgttgcgg ggaatttatt ttattcttac aaaaattggt atctgattat tttattaacc      480
atattcaatt agagaataga agaatagaga aaagcccttt tgtgggatat ggttctaaat      540
tgttgtttag ttcttgtgtg tcagttttgg ctctcgtcga ccaaagaaga ttaaagaaac      600
ctctacctta ttttaactca attcttttgt ttttgcaatg tcctttgctt tccaaaattg      660
ttagtcttac ttttcactac tttgatagac attgcctttg cgtttccctg attaataagc      720
cagagtactt aaatcaaaat tgactgtttt gtgcatcctg catcacgttt ccaatcagaa      780
ccatagtgtt gtcgttgtgt cattatccga atttaagtgg agacattggt aagttattta      840
taaactaatt acaatctatt tttctaatta tttcaaataa catatttaag ctctgtagct      900
tccactagac ggtgaagatt tgaagtgaga gctctctttg cattgctcac ccaccaatgg      960
atctacctac ccttcttctt cttctcctcc ttttaaaccc taaagttttc cctttccgtt     1020
caacaacgcc acaatccatt gcactgggat ccaacaatgt cctccgactc gtccaagatc     1080
```

```
aagaggaagc g                                                        1091
```

<210> SEQ ID NO 44
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0186 as found in
      Promoter Report #44
<220> FEATURE:
<221> NAME/KEY: misc_feature
<223> OTHER INFORMATION: T3 Seedling Expression: GFP expression observed
      in the Epidermis (Ep) of the hypocotyl

<400> SEQUENCE: 44

```
tggacaatta ctcttgtgtg tatccttgga gttgctgttt catatgtaag tggacaatta    60
ctcttgtgtg tagccttgga gttttttat ttacgttatt ttggtcagcc tttaattatt   120
ttgcaaaaaa tgtatctgtt tttgccacat gcccacataa tacatttcgc aaatttgata   180
cattatgctt tggcccttgt atattcggta aaaaaaaaag ctcaggctac tctcaaaacc   240
ggctctgagt attcgtaggc cacaatcgaa gaaaaaagt gccgatttac atattttttca   300
tacaaaaaat taaaactgtt atgtattatt caaaagctat ttacatatgt tttactaaca   360
cgttttcaat attttcttaa tccttttcaa aatttaacta agtataatac ttttttttgtg   420
tgttatttcg ttgttttggt taaagaaaaa cgaaaaaaag agagagttat tcatccttgc   480
agataaggct agggttggtt gaataaagat gtgcatatct tataccacta gaccaaagaa   540
acagtcacaa gtaaaaggcc gaatccttt tataaaatat aaacagacga aagctaatgc   600
ttcatgggct tggcccaagt gcaggctctc gctagtcgct acgctacaac tatcccatat   660
ttaattagtg aagagtattt tattattttg gtcaacgggc tatctttgtt gacaaaacta   720
tcccattggt aaagaaatag caaaataggc gtttcattct ctatatttaa acttgatttt   780
atgaagagtt gaatagctga accaggaaga tatttaagaa gcccgtactt cacgctttaa   840
ctgtcaatcg atagatcata ataaatgact atctatggat aggaactata actgaattca   900
gaaagaatct actactacta taaatactaa aagagtatta atacaacgga aaaaacaaaa   960
caaaaaaaag ggggaacaag ggagtttcat gttaaaaag                           999
```

<210> SEQ ID NO 45
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0121 as found in
      Promoter Report #45
<220> FEATURE:
<221> NAME/KEY: misc_feature
<223> OTHER INFORMATION: T2 Mature Plant Expression: GFP expression
      observed in the Inner integuments (Ii), Micropyle (Mp) and Outer
      integuments of the pre-, the Micropyle (Mp) and Outer integuments
      (Oi) of the post fertilized ovule

<400> SEQUENCE: 45

```
ttggattttt ttttgttga gtcagcagac catctaatct ctcttttcc accacagcct      60
gctttctatg aagcatttgg gcttacggtt gtggaatcaa tgacttgtgc actcccaacg   120
tttgctacct gtcatggtgg acccgcagag attatcgaaa acggagtttc tgggttccac   180
attgacccat atcatccaga ccaggttgca gctaccttgg tcagcttctt tgagacctgt   240
aacaccaatc caaatcattg ggttaaaatc tctgaaggag ggctcaagcg aatctatgaa   300
```

```
aggttggccc attctccttg acaggcttaa caatacaact tgtatcgctt caacaagatg      360
atggcttaat aaggatttt gcatgtatag gtacacatgg aagaagtact cagagagact      420
gcttaccctg gctggagtct atgcattctg gaaacatgtg tctaagctcg aaaggagaga      480
aacacgacgt tacctagaga tgttttactc attgaaattt cgtgatttgg ttagtgtaac      540
ccactgttat tcttttgatg tctacatcta ctttacttac attattcttt tcttcggttt      600
gcaggccaat tcaatcccgc tggcaacaga tgagaactga tcatgacagg gtaggatttt      660
atttcctgca ctttctttag atcttttgtt tgtgttatct tgaataaaaa ttgttgggtt      720
ttgtttcctt cagtggtttg attttggact tatttgtgtt aatgttgttt tggctgttct      780
cttaatatca ataacaaata aatttactgg ttggtatcta agatctaaca atagttacta      840
tttttagagg taaagacacc aaccttgtta tattggtcag agagctaaaa ccttgacttg      900
ttgggaaaac aaaactctaa tgacagaaaa tctgacatga tgccttataa ttcacagcct      960
catgttctac ataaatccta acaatagcac tttgtttct                             999
```

<210> SEQ ID NO 46
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter construct YP0096 as found in
    Promoter Report #46
<220> FEATURE:
<221> NAME/KEY: misc_feature
<223> OTHER INFORMATION: T1 Mature Plant Expression: GFP expression
    observed in the pre-fertilized ovule, the Egg cell (Ec) and
    Synergid cell (Sn) of the Female gametophyte, the Zygote an Hour
    after fertilization

<400> SEQUENCE: 46

```
gaggtcagtg agtcgattgg tgcaaaattg aaaaattgaa gggtgaaaca aatttaaaga      60
taatatctat taaatcctct aattttaaaa atttagcaaa aattgtattt tcttatggat     120
ctgttagttc acacgtatct taattagtac caaatcatat ctaatgatta gtgataaaac     180
tagttagata tctatatgtg tctttaccat ttaacttgaa tccttcttct ttttttacg      240 taaacaactt gaatccttcg ttaatacata aatttaaagc attttttctt taattctatt     300
gatcggtata tatttactat aagttttagc tcatatgcaa tttcaaatga tatgctttta     360
aattttgtct aggtgtgata gttgtatctt taacataaat cttatagcaa aattatactt     420
gatattctaa atttatctat ttgctcttgt gaacctcata ttagtctaga gaaactttga     480
aatcctttca attagttgta tgtccaatac attttttacta acatttatta gtctttttaa    540
ttaagattat tgttagaaaa aaaaagattt tttaaaaata aataatatgt tttagataca     600
atgtgagtta ggcttcttat attttaaaaa ataaatttat ttcatactta aaaatagttt     660
ggaatttcaa tttatttggc tgaataccat aaaatatgtc aatttgaacc ttatacccat     720
tgactatttg gtgttagaaa ccctttaaca aaaaaaaact atttggtgtt agatatcaaa     780
ataaaaaaag tttaaccatt ggtttcttat attgaattgg atattgttac atgtattaaa     840 gttttttgg tttaatttg aaacgttgat agaaactatt aagtttaagt ttggtagtat      900
atttatttgt ggaaaattta attgccatta aatataacgt caacttttt tggttttttt     960 tgagaagtta cgttgtgatt ttgatttcct atataaagt tagattacgt catttttaa      1020
```

<210> SEQ ID NO 47

```
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter construct YP0098 as found in
      Promoter Report #47
<220> FEATURE:
<221> NAME/KEY: misc_feature
<223> OTHER INFORMATION: T2 Mature Plant Expression: GFP expression
      observed in the Guard cell (Gc) and Stomata (So) of the stem
<220> FEATURE:
<221> NAME/KEY: misc_feature
<223> OTHER INFORMATION: T2 Seedling Expression: GFP expression observed
      in the root hairs of the root, the Guard cell (Gc) of the leaf
      and leaf petiole
<220> FEATURE:
<221> NAME/KEY: misc_feature
<223> OTHER INFORMATION: T2 Mature Plant Expression: GFP expression
      observed in the inflorescence meristem, pedicel and the
      pre-fertilized silique
<220> FEATURE:
<221> NAME/KEY: misc_feature
<223> OTHER INFORMATION: T3 Seedling Expression: GFP expression observed
      in the Epidermis (Ep)

<400> SEQUENCE: 47
tatttttata aattatctta gtaaaagtat gtattttcta atagatctgt tagttcatac      60
atatcttaat tagtgttaaa ttagatctaa tgattagtga taaagttttt agatatcgat     120
ataggtgtct ttaccattta acttgaatcc tttgttaatg taaaattta aaatattttg      180 ctttgattct acttattggt atataatttt aacatatcaa tccaatgcca ctcttaaatt     240
atcatgtact tttcgatata tgttatgact cacttgttat gaaacaatgg attttcacca    300
attttggtta tttattaact agaagtttta gctcttgtgc aattttaaat gatatgcttt    360
taaaattggt ctagttataa tagttgtatc tataacataa aacttataac aaaactatac    420
ttgatattca aaaattattg atttgctctt gtgaacttca tattagccta gagaactttg    480 aaaaccttc aataaattgt atgtcgaata aagttttaca acatttatt agccatttcg      540 attaagacta ttgtgagcaa aagtttttt tattataaaa taataatat gtttaagata    600 aattgtgagt taggcttctt atattttaaa aattatataa gtttatactg aaaaagagtt    660
aaaattttca aattttaaat ttatttggct taagaacata aatatgtcaa tttgaaccct    720 atcccacta aatattccat gttagataac gaaataaaag aaaattaact attggtttct     780
tatattgaat tggatattgt tacttgtatt tatgttttt gtttcatttt taaacgttga    840
taaaatcatt aaactaaagt tttgtagtat atttatttgt cgaaaattta ttcccattaa    900 ataaacgtt aaatttattt gtctttatta aaaagttac tttgtgattt tgatttccta     960
tataaaattt agataacttc aattttcaaa taaaaaat                             998

<210> SEQ ID NO 48
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0108 as found in
      Promoter Report #48
<220> FEATURE:
<221> NAME/KEY: misc_feature
<223> OTHER INFORMATION: T1 Mature Plant Expression: GFP expression
      observed in the Vascular (Vs) and Pedicel (Pd) of the
      inflorescence meristem, the Vascular (Vs) of the sepal, leaf and
      stem, the Sepal (Se) and Pedicel (Pd) of the flower bud, the
      Septum (Sp) of the silique
<220> FEATURE:
```

<221> NAME/KEY: misc_feature
<223> OTHER INFORMATION: T2 Seedling Expression: GFP expression observed
     in the hypocotyl root transition zone, the Phloem (Ph) of the Root
     (Rt)

<400> SEQUENCE: 48

```
ttagctgaac caggaaattg atctcttata ccagtttccg ggtttagatt ggtttgatgg    60
cgatttgatt aaacccccga aatttttatgt cgtagttgtg catagtatta ttattctttg   120
cggacaatag acgtatcggg accaagttct gtagcaaaat tgtataagct taagtttgat   180
gaaatttaaa ggtaatcact aaaacccaaa tgggacaata aaccggtgaa gatttagagt   240
ttttaatttt gactcatgaa tctggagaaa gagccctcgt taaaaggagt gaatcaatcc   300
atagggaaa  aagttttgtc ttttttaaaaa ctaaagaacc aaaccttaat agaagcagct   360
caatgtgtga caactttcca ctggcactaa gataaagtga ctagcgatga gtgcaattat   420
tgaaatagta gatggtaaat attacataca agagtaaaaa tatctttatg tcaatgctta   480
attcagtgtt tctggttaac aagagaatct tctctaactt tcgtaattgg gtcttataaa   540
attttatgca attatgattt taccctttta ctacttttca ttagctttca cgaatctatt   600
ttgacaagag aaatcattag aggtaaacat gcttttttggt caagggcctt aacagttcca   660
ccaatcaagc tcaaaagttg tacttaaccg acatcttctg tgaaaacata taattacatg   720
tacaaatcaa aactaccta  tgaaataaat agaaatattg cagttcattt ctaatttaac   780
ctcttcaact tttaaaacta tttacatttc tttatgtcat ttctagtcat tttgatgcaa   840
attgtaccat ttatggatta tcttcacaaa ttttttaagtt ggtgaaaact ttttggtggg   900
tagttaaaac ttgaaataga aatttacttt accaaaataa actaatgaaa agtaatcact   960
ccactcccta taataagatt tccaacgttc ccactaagc                          999
```

<210> SEQ ID NO 49
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter construct YP0134 as found in
     Promoter Report #49
<220> FEATURE:
<221> NAME/KEY: misc_feature
<223> OTHER INFORMATION: T1 Mature Plant Expression: GFP expression
     observed in the Septum (Sp) and Epidermis (Ep) of the silique
     Carpel (Ca), Style (Sy)
<220> FEATURE:
<221> NAME/KEY: misc_feature
<223> OTHER INFORMATION: T2 Seedling Expression: GFP expression observed
     in the Epidermis and Root Hair of the hypocotyl, the Epidermis of
     the cotyledon, the Atrichoblast and Trichoblast of the root
     differentiation zone
<220> FEATURE:
<221> NAME/KEY: misc_feature
<223> OTHER INFORMATION: T2 Mature Plant Expression: GFP expression
     observed in the Epidermis (Ep) and Vasculature (Vs) of the
     silique, the Epidermis (Ep) and Cortex (Cr) of the stem
<220> FEATURE:
<221> NAME/KEY: misc_feature
<223> OTHER INFORMATION: T3 Seedling Expression: GFP expression observed
     in T3 Seedling tissue expressions similar to T2 seedling
     expression

<400> SEQUENCE: 49

```
cctactttag gcttaaacaa gaagaaaata tgactgctaa gtcatatttt tcaactctca    60
tgagcaaccg taaagttgca ccgcaatatc caacaaatga cattcgtgtt atctacaatc   120
taatgttgaa aatttggctc atctaataaa ggagacaaaa gttatatctc tttcacacac   180
```

```
acgttaatgg aagtgtaaag gcggtgagag tgtgggagag acttggggaa caagaagaag    240
gacgcggtca aaaagtgacg gtgggctacg gcttttcttg gtagcagttg gaaattccat    300
taatgactta aaaagtgtaa atcttatctt cttttttattt tgtgatttga tatgcacatt   360
catttcatga aaatatttgt atagtttgat gatcatacga caaacttata gggttcacaa    420
agtagatgca atagttgcat acctctgttt aaatgttctt gttaatatta taattgatga    480
cggaactcgt gaatgttatt caaaatgtcc atgtaattca agatcatgca ctataataag    540
taatctatca ttttcagcac aacaattttg acaaaaagta aaaataaaat agagtaaact    600
gatatcatat ttccgaatta tatatataaa cgttttctgt ttctcaatgg tctctttcac    660
tcttgtgttt tctaatattt catttaaacc tatttctaaa ctaagcacat ctttgttgat    720
tgattgcatt tcaaccaaaa tcgataaccg aatcattgtt tttttatgtt ttatttcagc    780
ttaccacaca cgtttagaat tttaaaaata aaacaaaaaa aagttaactc gttacaaatg    840
aaaatgatat ttttaattgg actcgatgga aaggaccaat ttattcaaca ctattgttta    900
gtccgaacac ttgccgcgta agttttccaa ctcccccccat tgacctttcg cactttcaca    960
aactccgtat atatataatg gatacactct ctctttgatc t                      1001

<210> SEQ ID NO 50
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0138 as found in
      Promoter Report #50
<220> FEATURE:
<221> NAME/KEY: misc_feature
<223> OTHER INFORMATION: T2 Mature Plant Expression: GFP expression
      observed in the inflorescence meristem, the Epidermis of the petal
      and stem, the Epidermis, Mesophyll and Cortex of the silique, the
      Epidermis and Cortex of the stem
<220> FEATURE:
<221> NAME/KEY: misc_feature
<223> OTHER INFORMATION: T2 Mature Plant Expression: GFP expression
      observed in the Epidermis and Mesophyll of the leaf
<220> FEATURE:
<221> NAME/KEY: misc_feature
<223> OTHER INFORMATION: T2 Seedling Expression: GFP expression observed
      in the osette leaf, the Epidermis and Mesophyll of the cotyledon
      nd rosette leaf, the Vasculature of the rosette leaf, the Cortex
      f the lateral root, the root elongation zone and the root tip
<220> FEATURE:
<221> NAME/KEY: misc_feature
<223> OTHER INFORMATION: T2 Mature Plant Expression: GFP expression
      observed in the pidermis (Ep) and Cortex (Cr) of the stem, the
      Micropyle (Mp) of the mature ovule
<220> FEATURE:
<221> NAME/KEY: misc_feature
<223> OTHER INFORMATION: T3 Seedling Expression: GFP expression observed
      in T3 Seedling tissue expressions similar to T2 seedling
      expression
<220> FEATURE:
<221> NAME/KEY: misc_feature
<223> OTHER INFORMATION: T2 Mature Plant Expression: T2 Mature tissue
      expression (if different expression pattern), the flanking cells
      of the Lateral root in the root transition zone, the Epidermis
      and Mesophyll (Me) of the leaf

<400> SEQUENCE: 50
tgtgtgtcct aaaatagtttc ttttttaaaat ttgtaaatac caagacgcgt atttaagagt    60
attttgaaaa gatatttgat tataaaaaga aagaaaaaga gaaggctgag gattaactgc    120
aacgtctacc gttggaaaag aaaaacgatc agaaaacaca gaaattaata aaaagagaga    180
```

```
aaaaaaaata gagtatgaga gatgcacatg ggtgcctgca aaaaaaaggt agaagaaatt      240
tgtctgaaag tgtcacaggc acactctctc gaaccacatt taacaacact ccaaacactc      300
ttcttctact ttgtaccctt cagtacatta ctctttccaa agtccgtgat ttacgctctt      360
cgatgacacc tctcaacaga gagagactac atgtgtacat tttcttctac cattaaattt      420
tgaagatttt cgatgattca atttagtata tatatggaag ataaaatttt cattgtcttt      480
ctacatgata gtaacggttt tagaagggtg gttatcactt atagtatttg agttaagaaa      540
tataaaaata tacgtgactg ttttttccttg taaactatttt ttaggcccttt atttttattc     600 aagtagtcac atacgtgttt gaagtgtatt taactaagaa aaagaaagta ggaaatgaaa      660
aggatatagt atttatggtg taatcttggt aaggaccagg agatcagaag gggccacaat      720
gtcacaaaga ggaccaacaa tgaaattaaa tcctcagctg gcctttaaca ttttggctcc      780
caccatctcc ttccacacat atgcacatgt cttcatgtct ctctctctct atacgttacc      840
tacacaaata tgtacagaca aatagcccat tacaaaatct ttatttataa atatatactc      900
ctcaactccc tcaatatcca cccatctcct tctccataac tctctctctc tctccctaaa      960
cacaaccaaa gactttatc tctcaggaac cccaaaaac                             999
```

<210> SEQ ID NO 51
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0177 as found in Promoter Report #51
<220> FEATURE:
<221> NAME/KEY: misc_feature
<223> OTHER INFORMATION: T1 Mature Plant Expression: GFP expression observed in the Guard cells (Gc) of the flower pedicel, the silique and the stem
<220> FEATURE:
<221> NAME/KEY: misc_feature
<223> OTHER INFORMATION: T3 Seedling Expression: GFP expression observed in the Guard cell (Gc) of the rosette leaf, the Root hair (Rh) of the hypocotyl root transition zone

<400> SEQUENCE: 51

```
tgtgtgtcct aaatagtttc ttttttaaaat ttgtaaatac caagacgcgt atttaagagt      60
attttgaaaa gatatttgat tataaaaaga aagaaaaaga gaaggctgag gattaactgc     120
aacgtctacc gttggaaaag aaaaacgatc agaaaacaca gaaattaata aaaagagaga     180
aaaaaaaata gagtatgaga gatgcacatg ggtgcctgca aaaaaaaggt agaagaaatt     240
tgtctgaaag tgtcacaggc acactctctc gaaccacatt taacaacact ccaaacactc     300
ttcttctact ttgtaccctt cagtacatta ctctttccaa agtccgtgat ttacgctctt     360
cgatgacacc tctcaacaga gagagactac atgtgtacat tttcttctac cattaaattt     420
tgaagatttt cgatgattca atttagtata tatatggaag ataaaatttt cattgtcttt     480
ctacatgata gtaacggttt tagaagggtg gttatcactt atagtatttg agttaagaaa     540
tataaaaata tacgtgactg tttttccttg taaactatt ttaggcccttt atttttattc     600 aagtagtcac atacgtgttt gaagtgtatt taactaagaa aaagaaagta ggaaatgaaa     660
aggatatagt atttatggtg taatcttggt aaggaccagg agatcagaag gggccacaat     720
gtcacaaaga ggaccaacaa tgaaattaaa tcctcagctg gcctttaaca ttttggctcc     780
caccatctcc ttccacacat atgcacatgt cttcatgtct ctctctctct atacgttacc     840
tacacaaata tgtacagaca aatagcccat tacaaaatct ttatttataa atatatactc     900
```

```
ctcaactccc tcaatatcca cccatctcct tctccataac tctctctctc tctccctaaa    960
cacaaccaaa gactttatc tctcaggaac cccaaaaac                            999
```

<210> SEQ ID NO 52
<211> LENGTH: 1006
<212> TYPE: DNA
<213> ORGANISM: Arabidopsis thaliana
<220> FEATURE:
<221> NAME/KEY: misc_feature
<223> OTHER INFORMATION: Ceres Promoter construct YP0192 as found in
      Promoter Report #52
<220> FEATURE:
<221> NAME/KEY: misc_feature
<223> OTHER INFORMATION: T2 Mature Plant Expression: GFP expression
      observed in the Vasculature (Vs) of the inflorescence meristem
      and the Sepal
<220> FEATURE:
<221> NAME/KEY: misc_feature
<223> OTHER INFORMATION: T2 Seedling Expression: GFP expression observed
      in the Guard cell (Gc) and Vasculature (Vs) of the leaf

<400> SEQUENCE: 52

```
tcctcctact gtctgctacg tcaacaagtg gattgcaatc agacggtgat tgtgtctctt     60
ttcattctct ctcttttact aatttctctg ataattaaac tgagaatgta tattaagaaa    120
aaaaaacaaa aacaagagag gaattttcat acacactaac ttaagactct ttgtaagttt    180
tcccaaatat ggatttcta gtataaatat gagttcatta gtttcaccaa gcctacaagc    240
atctctccat ctcaaatcat attcacctaa aaatcaggtc ccctctcttt atatctctaa    300
cattcttata tcagatcata ttttttggat ttcttgttaa gtaacaccaa tcttttaaaa    360
gtgttttcag gttaatataa aagaataatg atgttttcgg tgacggttgc gatccttgtt    420
tgtcttattg gctacatta ccgatcattt aagcctccac caccgcgaat ctgcggccat    480
cctaacggtc ctccggttac ttctccgaga atcaagctca gtgatggaag atatcttgct    540
tatagagaat ctggggttga tagagacaat gctaactaca agatcattgt cgttcatggc    600
ctcaacagct ccaaagacac tgaattttcc atccctaagg ttcactctta ttctcaatat    660
taactctcgt acatgtcaca tgcccatttt caccatttta gatatacagt tttgatactt    720
tactttgcat ttattttgct atatgtaatt gaggatattg ttttaatttc tttgggtttt    780 ttttttttcgg ctaaatgaga attcactgtc tttggttctt gaaaaaaaag tatttgttaa    840
tggtaaacgc taaacgctat ttgagtttat gttttttcaa gaactgaaaa cgttttattg    900
aaaatataca cttttttgc tatttatagg aaagcatatc acatcacatc tagacgcaaa    960
cgcaaaattg agtttaaag caaccacaat cttaaatgca atgaaa                  1006
```

<210> SEQ ID NO 53
<211> LENGTH: 1071
<212> TYPE: DNA
<213> ORGANISM: Arabidopsis thaliana
<220> FEATURE:
<221> NAME/KEY: misc_feature
<223> OTHER INFORMATION: Ceres Promoter construct YP0204 as found in
      Promoter Report #53
<220> FEATURE:
<221> NAME/KEY: misc_feature
<223> OTHER INFORMATION: T1 Mature Plant Expression: GFP expression
      observed in the inflorescence meristem
<220> FEATURE:
<221> NAME/KEY: misc_feature
<223> OTHER INFORMATION: T3 Seedling Expression: GFP expression observed
      in the seedling root, the Epidermis and Root hair of the
      hypocotyl root transition zone, the Epidermis and Root hair
      of the root differentiation zone

<400> SEQUENCE: 53

| aactaattag gtcgttaatt gtccaagggt ttttcatagt tgatatagtt ctgttcaaat | 60 |
| atagccatcc ttaatcgatt catgggatcg taaattacta cttcgagtgt tgtaaaaaaa | 120 |
| aatgaaactt ctacattaca aactcgaatt taatgcatct ggagtgatac tataaaagta | 180 |
| gggatgctct caggtcgcat ttgagagaca cagaaatgat tttaatggaa ttaatatatt | 240 |
| ttcagttttt cacaaaaaaa aattgtgttt ataacaactg cagattcaat gctgatttta | 300 |
| tgagtctcac ctatagaatt tatatttcta tattcataga ggcagtatag gtgttgaccc | 360 |
| aacatcgaaa gaacacttcg taaaaaattc tttggaacaa ggctgaaaat ttactcccaa | 420 |
| atttagctat ccgatgaaga taaatcattt accgtttatt aaagaattat cgagatttta | 480 |
| gtcaaaacca aaagagatta tgagcctaag attttgaatt tgtattggta aaggaaattg | 540 |
| aacgaaaatt tcagaaaaaa atattaataa attgaacgat agagttcact tactacatag | 600 |
| tcaactagtg cctagctata atagtttcaa aagacaaaaa aaacaaaatc ggttaactac | 660 |
| ttccgtgaca taattctcat cttgatttt gaatccagtc taatttgaaa agtatattca | 720 |
| aaatctttaa atccattaat gataactttt ataatacgtt gacacacgca attgtatata | 780 |
| caatattctt gaattttaaa tgtaaattct agaatatatt gcgatcacca cactaatcaa | 840 |
| aatctttggg acaacttgaa cccacatttg acttttcttg gtcaaatatt ttggcatcat | 900 |
| gcatgatctt ctctataaaa accaaaaggc ctcaacgaca ttcataaact cagtcattat | 960 |
| atttattttt gttgtatttc aacgttcaat ctctgaaaac cattgcactg ggatccaaca | 1020 |
| atgtcctccg actcgtccaa gatcaagagg aagcggaacc gcatcccgct c | 1071 |

<210> SEQ ID NO 54
<211> LENGTH: 1191
<212> TYPE: DNA
<213> ORGANISM: Oryza sativa
<220> FEATURE:
<221> NAME/KEY: misc_feature
<223> OTHER INFORMATION: Ceres Promoter construct pCRS-HT2-pGluB-1
      as found in Promoter Report #58
<220> FEATURE:
<221> NAME/KEY: misc_feature
<223> OTHER INFORMATION: T2 Seedling Expression: GFP expression observed
      in the Epidermis and Vasculature of the cotyledon, the Epidermis
      and Mesophyll of the primary leaf, the Lateral root, lateral root
      initial and lateral root primordia
<220> FEATURE:
<221> NAME/KEY: misc_feature
<223> OTHER INFORMATION: T2 Mature Plant Expression: GFP expression
      observed in the silique primordia, the Cortex and Stigma of the
      developing and fertilized silique, the Vasculature of the sepal,
      mature embryo and the leaf

<400> SEQUENCE: 54

| gatctcgatt tttgaggaat tttagaagtt gaacagagtc aatcgaacag acagttgaag | 60 |
| agatatggat tttctaagat cgggggaccg agtggaccgg acgaggatgt ggcctaggac | 120 |
| gagtgcacaa ggctagtgga ctcggtcccc gcgcggtatc ccgagtggtc cactgtctgc | 180 |
| aaacacgatt cacatagagc gggcagacgc gggagccgtc ctaggtgcac cggaagcaaa | 240 |
| tccgtcgcct gggtggattt gagtgacacg gcccacgtgt agcctcacag ctctccgtgg | 300 |
| tcagatgtgt aaaattatca taatatgtgt ttttcaaata gttaaataat atatataggc | 360 |
| aagttatatg ggtcaataag cagtaaaaag gcttatgaca tggtaaaatt acttacacca | 420 |
| atatgcctta ctgtctgata tattttacat gacaacaaag ttacaagtac gtcatttaaa | 480 |

-continued

```
aatacaagtt acttatcaat tgtagtgtat caagtaaatg acaacaaacc tacaaatttg      540
ctattttgaa ggaacactta aaaaaatcaa taggcaagtt atatagtcaa taaactgcaa      600
gaaggcttat gacatggaaa aattacatac accaatatgc tttattgtcc ggtatatttt      660
acaagacaac aaagttataa gtatgtcatt taaaaataca agttacttat caattgtcaa      720
gtaaatgaaa acaaacctac aaatttgtta ttttgaagga acacctaaat tatcaaatat      780
agcttgctac gcaaaatgac aacatgctta caagttatta tcatcttaaa gttagactca      840
tcttctcaag cataagagct ttatggtgca aaaacaaata taatgacaag gcaaagatac      900
atacatatta agagtatgga cagacatttc tttaacaaac tccatttgta ttactccaaa      960
agcaccagaa gtttgtcatg gctgagtcat gaaatgtata gttcaatctt gcaaagttgc     1020
ctttcctttt gtactgtgtt taacactac aagccatata ttgtctgtac gtgcaacaaa     1080
ctatatcacc atgtatccca agatgctttt ttattgctat ataaactagc ttggtctgtc     1140
tttgaactca catcaattag cttaagtttc cataagcaag tacaaatagc t             1191
```

<210> SEQ ID NO 55
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0008 as found in
      Promoter Report #60
<220> FEATURE:
<221> NAME/KEY: misc_feature
<223> OTHER INFORMATION: T1 Mature Plant Expression: GFP expression
      observed in the Endothelium (Ed) of the mature seed
<220> FEATURE:
<221> NAME/KEY: misc_feature
<223> OTHER INFORMATION: T2 Seedling Expression: GFP expression observed
      in the Cortex (Cr) of the seedling

<400> SEQUENCE: 55

```
ctcgagagat gaagtcttag taatgtttga acaaacaata atcacgtttt ccatcaaatt       60
cgagcattta aagtttatat tactacatgc cccaagatga taccgtccat ctcatccgaa      120
aatatttctg aaattgcgct aagacaacaa tgtttgctca aattcgatca tttaaagttt      180
acaaatctct catcaatctt acaaacttct cacactaaac agaggtacat attttcttat      240
aaagacaaaa ggttcgaaca gctggcttct caactcgagt tgtttgtcag ggcctctctt      300
cactaactac aagttggtac ttcaaatatt ggtggctagc ttcacgtgat attgtctaca      360
aattaaaccc atgaaaaagc tgcattaatt gttccaagtg aaccctgagg agtgtcaata      420
gtctttgctt tagtgtgatc attaaaccaa atctctaaat tcctaatttg tactaacatt      480
tggaacgtat ttcctactct tctccctgct ccaactccca aaaataagat tagttagatt      540
tctataacta atatacatgt atactcccaa aaacagtaaa accatattaa taaagctaat      600
tttgcataga tttatttcgg taaaccggcg gttcaagttg gggaaaaaaa agacaaacgg      660
tctaaagtca tccaaagaca aaaaaccaaa gacaagttga gagagacgag accaatcaca      720
acattgcttc gtagattgcg tgacatcatc cttgacggct actttcattt gtgtcttatt      780
tggataaaac gcacgtgttt aattcacgaa ccttcatagc aataagaaat ttccattact      840
ttcatatttt caacttttt tattacccat tacatgctta aaatattaat tcacaagtct      900
ttgtcaaaat tcaatatttt ccaggttcat gaacccttt tatctcaatc tactctataa      960
tatctcccta taaattacaa caaaacctct ttatttttca                           1000
```

```
<210> SEQ ID NO 56
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0009 as found in
      Promoter Report #61
<220> FEATURE:
<221> NAME/KEY: misc_feature
<223> OTHER INFORMATION: T2 Seedling Expression: GFP expression observed
      in the Epidermis and Cortex of the hypocotyl root zone, the
      Epidermis, Cortex Pericycle and Vasculature of the root
<220> FEATURE:
<221> NAME/KEY: misc_feature
<223> OTHER INFORMATION: T2 Mature Plant Expression: GFP expression
      observed in the Guard cell, Epidermis and Vasculature of the leaf,
      the Vascular bundle of the stem

<400> SEQUENCE: 56
aattcgtttt ttatactccc tctgttccaa gatacttgat attttgggtt tttgcacaag      60
aattaagaaa agtaactttt atattttttaa ttattctttt agttagttta ataatattaa    120
ttttacttct ctcatttcat tattggttac aaacaaaaat aataatgata gtttttcaaa    180
acatcaattt tggtggaaca aataaaaaaa ctcaaaatat caaataactt gaaacagagg    240
gagtagttaa ttaaaaaaag atatttcaca ctttgacttg gcgaagcctc ataacaatga    300
agttatgtat gaactatata tgaagttaga acaatggaa aacagcttgt aaatattcat     360
tgttgtatat atgttttttt gggtcaattt ggtgcatgaa caaaaataaa aacgtagatg    420
aaaaccggat attttggtgt taacatttgc atttgaactt cgtgaaagac ggataaaagc    480
tcatttttgt tttttattat atggctgcta ttagtacaca gagttgaact ttagaatact    540
aaaaatctcg acatcttttta ttttattttt gtcaagcatc gacatctttt ctgttcaaga   600
aaacgaccgc aatagtcgaa taatataact cttggactag ttaatatata tttgcgatag    660
attttcgatc tcacttatat cttataacca agagacaaaa acaatattgc agtcaagtac    720
aaaacgaaaa caatcacaat gtcgactata gatgagtcgg tcattcgatc caacggctct    780
gagtccacga aacacgcaac caagtggtgc tctcttttac accaaatcat attatataaa    840
acttaaaaga aagagaggat ggttcgttgg ctccttcttg ttccttaatt aattcaaatt    900
atattcatca cctccattga ataagtccat ttcacgacaa agtcaccaat gcttctttta    960
catgtatata tacttctttc cactccctct tctctactca                         1000

<210> SEQ ID NO 57
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0010 as found in
      Promoter Report #62
<220> FEATURE:
<221> NAME/KEY: misc_feature
<223> OTHER INFORMATION: T2 Seedling Expression: GFP expression observed
      in the Phloem (Ph) of the root
<220> FEATURE:
<221> NAME/KEY: misc_feature
<223> OTHER INFORMATION: T2 Mature Plant Expression: GFP expression
      observed in the Guard cell (Gc) of the Pedicel (Pd) and Sepal (Se)
      of the flower, the Guard cell (Gc) and Vasculature (Vs) of the
      silique and pre-fertilized silique
<220> FEATURE:
<221> NAME/KEY: misc_feature
<223> OTHER INFORMATION: T2 Mature Plant Expression: GFP expression
      observed in the Carpel, Stigma and Style of the mature silique,
      the Septum of the silique, the Hydathode of the leaf, the
```

```
                        Mesophyll of the adaxial leaf, the Vasculature and Hydathode of
                        the abaxial leaf

<400> SEQUENCE: 57
aattcgtctt gcattggtaa tccaatattc catgtgatgc ttttctttct aactgaaggt      60
attcgtgaaa acgaattcaa gattgtggga gataattagg gtttcgtcaa aagcatgaat     120
taggaaaatt tgggattgat tttttgaatt tgggaaaagt cctaatttta attcgatcaa     180
agcttaaatg atgtcgtttt gggctgacta acgaagtcgt taacaggtgc caacgagtgt     240
taaaaatctg ttatcgcttg ataactcttt ggttttttag tctaatcaac acattctcat     300
gtttcaaaca gttaatcaac atattgttca tgttaaaaaa ttaacacatg tgaaattgat     360
atataaaaat atcatatatt ttcaaaagtt ggatcattaa ataaaaattt tccctatttt     420
tgaaataatt ctaaaacagt attaaagata tttcctgaaa ttgtttgcat gtgatcggtt     480
ttggaccgaa actaaaaaac ttagaaacta tattaacttt gagttgtcga gatgaagatg     540
tgaaatagaa ataggatc aatggttaga attttggcaa atgtatgaag gtgtgtttga      600
ttgaatattc caagtccttt gccttttgga ataggcataa ctactacaac aaagttttga    660
taggttttcc gaattcttta aactccttaa attttaata catctcaatc aaactccact     720
tatactaaaa ataatccata ttgcattttt aaaaatccta aaagaagaat cacatgataa    780
cttgataagc acttttaaat gatagatgtc cacgtagagg aataagacaa aaagacaaaa    840
taaagaaaaa ggacgaaatc taagagaga aataagtaa caagtccaag aaaaggtagt      900
atgatctttc tcggtccgat cctcgaaact ccctcgaagg ctcgaaccct ctctttgttt    960
ttttaccact atataagaaa gtccgattcc tcgtcactct                         1000

<210> SEQ ID NO 58
<211> LENGTH: 1054
<212> TYPE: DNA
<213> ORGANISM: Arabidopsis thaliana
<220> FEATURE:
<221> NAME/KEY: misc_feature
<223> OTHER INFORMATION: Ceres Promoter construct YP0039 as found in
      Promoter Report #64
<220> FEATURE:
<221> NAME/KEY: misc_feature
<223> OTHER INFORMATION: T1 Mature Plant Expression: GFP expression
      observed in the Antipodal cells, Central cell, Central cell
      vacuoleand Egg cell of the pre-fertilized ovule, the globular
      stage, heart stage and torpedo stage embryo in the ovule, the
      Cotyledon of the ovule
<220> FEATURE:
<221> NAME/KEY: misc_feature
<223> OTHER INFORMATION: T1 Mature Plant Expression: GFP expression
      observed in the mature pollen, the  fertilized ovule and embryo
<220> FEATURE:
<221> NAME/KEY: misc_feature
<223> OTHER INFORMATION: T2 Seedling Expression: GFP expression observed
      in the lateral root primordial, the lateral root, the Cortex (Cr)
      of the root and the root tip

<400> SEQUENCE: 58
ccgttcgagt atttgaaaat ttcgggtaca cccgcctaaa taggcggacc ttatctagta      60
tatatataca tttgaactat attgtttact ttttagttga tttaggctat gtcatgacat     120
tgacataaat ctacctgtta tttatcacgt gtaattcgtg taaagtgtaa actagaaagt    180
tcaaatacgt atttgttttt gttctgttat ataggattgt catagttgta aatctacaat    240
ttattacaac atgaataagt acacaagcaa tgtaattgga tttaattgct aaactcttta    300
catggtcaat ctaaatttga taagaaatac gtcacatatt actaagactg atagttttttt    360
```

-continued

```
tgttgtcacc aattattttt gttaaattga cgaaaacaat tccaaaaact caaatgtaca        420
aaatcataca gtctcacaaa catctcatag agaaagatat aaatctccca tatgggaacg        480
ataacacgag gtcgaaatac tattcgtaaa actaaaacgc cttagttata aatcgttagt        540
tgtaaccgcg gtcgagaata catacagatc cacgaaacta ctactacaca tgctgctgaa        600
ttggaatttg gaaaagacca tcttctttag gaagagctca cccaatgagt gacaaaggtg        660
tcggtggctt gttttctacc catatgtata catcaaatgg tagtttcatt aacgtttggt        720
tttgagaaaa gtaagacttt ggctagtagc taggttcgta tataataaac tcttttgaga        780
aagttcatca ctggtggaaa atgttaaacc ggttttttct cattttttcc gccatgttaa        840
ccaccggttt aaaaagaccg taacacattg aaagattaat aagggtatat ttgtaattac        900
ggtttgctgg caattttaa ttattatttt aattagagaa aatagagaag ccctatcaat         960
gtacatggta tatatataaa aggcaaaacc ctagaaaacg atactattcg actcagccgt       1020
cctttcgcaa gaaaccattt ggagttggag cttt                                   1054
```

<210> SEQ ID NO 59
<211> LENGTH: 1007
<212> TYPE: DNA
<213> ORGANISM: Arabidopsis thaliana
<220> FEATURE:
<221> NAME/KEY: misc_feature
<223> OTHER INFORMATION: Ceres Promoter construct YP0070 as found in
      Promoter Report #66
<220> FEATURE:
<221> NAME/KEY: misc_feature
<223> OTHER INFORMATION: T1 Mature Plant Expression: GFP expression
      observed in the Funiculus (Fn), the Chalaza (Ch) of the mature
      ovule
<220> FEATURE:
<221> NAME/KEY: misc_feature
<223> OTHER INFORMATION: T2 Seedling Expression: GFP expression observed
      in the Epidermis (Ep) of the petiole, the Hypocotyl (Hy),
      the Rooot hair (Rh) of the hypocotyl

<400> SEQUENCE: 59

```
ttggcgttaa tcgttaagaa aaaaacgtgc ctacctagcc aaatgacatc ttcctctttt         60
gtgtttagca caagtgaatg atccaaatat catctaccta atatgaccca taaaatagta       120
tgtgattgtc tttggatgtt atcccataac ataacttaaa tttgggatgc atgcatatat       180
tatatacttc atataaaatg agtggacctc ataagttgcg gtttcgattt ttatcaaaaa       240
caacagttgt ccacttttg atttgacac acacccacat tcaagcatct cctttcttct        300
atattattac tcaaagaata acaccccta aggataacac cattacacaa atcaattctc        360
agttaatcat ttgtttcaat atatgttagt acttaagaaa tattcgaata gttttacgta       420
ttcaaatttt ataattcag tgaatgttta attaccaagt catttggct tggaatctat         480 tcaattattc aaaaaaataa ataaataata ctgcatttta acgtatcagc cagtcaatat       540
attacacgtg tcataaagca ttacccacac gtttctcctg cctctttccc tttcattttt      600
ttttttcatt tttttttgttt cttctcttgt tgttgttatc ttcttctagc tagctctgtg     660
aaacacttca aatgaacaaa tatatcaaat aataatagtg taattaagtc ggaggaaaac     720
aacaagaacc cagaaagagg aacgaagaaa ctaattcaaa ggtatgatct tttattcttt      780
gagagaatta tgtttctttt gtagcaaatc ctctggtctt acgttagtc actgaatttg     840 ttccacttct ggaaaaatct agacaccaaa agcaatctat gaactttaat ttccaatcac     900 taccgtctttt tgaggttgta aaatcggtaa atggcagatt tttcactctc attcctttgt    960
ggtgatagga tcaagttcac cgcttcattt tagtcattaa acaaaga                  1007
```

```
<210> SEQ ID NO 60
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0086 as found in
      Promoter Report #68
<220> FEATURE:
<221> NAME/KEY: misc_feature
<223> OTHER INFORMATION: T2 Mature Plant Expression: GFP expression
      observed in the Shoot apical meristem, Silique, Stamen, Sepal, the
      Placenta Silique, stamen, Sepal, Abscision zone and Nectary, the
      Carpel, Ovule and Stigma of the immature silique
<220> FEATURE:
<221> NAME/KEY: misc_feature
<223> OTHER INFORMATION: T2 Mature Plant Expression: GFP expression
      observed in the Carpel, Ovule and Placenta, of the ovary, the
      Filament of the Anther in the stamen, the Cortex of the silique,
      the Outer integument and Funiculus ovule
<220> FEATURE:
<221> NAME/KEY: misc_feature
<223> OTHER INFORMATION: T2 Mature Plant Expression: GFP expression
      observed in the Embryo, Suspensor and Micropyle of the ovule, the
      Pollen, the Hyphosis and Suspensor of the embryo, the Cotyledon
      and Root of the mature embryo
<220> FEATURE:
<221> NAME/KEY: misc_feature
<223> OTHER INFORMATION: T2 Mature Plant Expression: GFP expression
      observed in the Epidermis, Pith and Vascular bundle of the stem,
      the Epidermis, Mesophyll and Vascular bundle of the leaf
<220> FEATURE:
<221> NAME/KEY: misc_feature
<223> OTHER INFORMATION: T3 Seedling Expression: GFP expression observed
      in the Hypocotyl and Rosette leaf in the seedling, the Epidermis,
      Mesophyll and Vasculature of the rosette leaf, the Epidermis,
      Vasculature and Root hair in the hypocotyl root
<220> FEATURE:
<221> NAME/KEY: misc_feature
<223> OTHER INFORMATION: T3 Seedling Expression: GFP expression observed
      in the Vasculature bundle (Vb), Cortex (Cr) and Epidermis (Ep)
      of the root

<400> SEQUENCE: 60
cttatccttt aacaatgaac aggtttttag aggtagcttg atgattcctg cacatgtgat      60
cttggcttca ggcttaattt tccaggtaaa gcattatgag atactcttat atctcttaca     120
tacttttgag ataatgcaca agaacttcat aactatatgc tttagtttct gcatttgaca     180
ctgccaaatt cattaatctc taatatcttt gttgttgatc tttggtagac atgggtacta     240
gaaaaagcaa actacaccaa ggtaaaatac ttttgtacaa acataaactc gttatcacgg     300
aacatcaatg gagtgtatat ctaacggagt gtagaaacat ttgattattg caggaagcta     360
tctcaggata ttatcggttt atatggaatc tcttctacgc agagtatctg ttattcccct     420
tcctctagct ttcaatttca tggtgaggat atgcagtttt ctttgtatat cattcttctt     480
cttctttgta gcttggagtc aaaatcggtt ccttcatgta catacatcaa ggatatgtcc     540
ttctgaattt ttatatcttg caataaaaat gcttgtacca attgaaacac cagcttttttg    600 agttctatga tcactgactt ggttctaacc aaaaaaaaaa aaatgtttaa tttacatatc     660
taaaagtagg tttagggaaa cctaaacagt aaaatatttg tatattattc gaatttcact     720
catcataaaa acttaaattg caccataaaa ttttgtttta ctattaatga tgtaatttgt     780
gtaacttaag ataaaaataa tattccgtaa gttaaccggc taaaaccacg tataaaccag     840
ggaacctgtt aaaccggttc tttactggat aaagaaatga aagcccatgt agacagctcc     900
attagagccc aaaccctaaa tttctcatct atataaaagg agtgacatta gggttttgt      960
```
tcgtcctctt aaagcttctc gttttctctg ccgtctctc          999

<210> SEQ ID NO 61
<211> LENGTH: 1106
<212> TYPE: DNA
<213> ORGANISM: Arabidopsis thaliana
<220> FEATURE:
<221> NAME/KEY: misc_feature
<223> OTHER INFORMATION: Ceres Promoter construct YP0088 as found in
      Promoter Report #69
<220> FEATURE:
<221> NAME/KEY: misc_feature
<223> OTHER INFORMATION: T1 Mature Plant Expression: GFP expression
      observed in the Hypophysis and Suspensor of the heart stage
      embryo, the torpedo stage embryo, the Root apical meristem of the
      mature embryo
<220> FEATURE:
<221> NAME/KEY: misc_feature
<223> OTHER INFORMATION: T2 Seedling Expression: GFP expression observed
      in the rosette leaf, the Lateral root, the Epidermis of the root,
      the Lateral root tip and the root tip

<400> SEQUENCE: 61
tcgattggga ttactacttc atctagtaag gttctgaaaa cgtttgttgt tgataaggaa      60
gattcgtctc aggttattac tgttgatctt caaggtttgt gattgtgacg cttatacatg     120
tgctgaaact gtggtgttta tttattgaaa acaaaaaaaa agtctctctt gtagtttcat     180
tgtactaaat agaaaacaag aaacgttttt ttctttaatc ttctacattg ataatattgg     240
atcaaaggat tgtttctgca agacacaaca caaacatact tatactagtt tacttctact     300
aagtactaac tacatacccca tacacacact tgcacctaga ctttacttct agacatcatt     360
accctaaggt agaaccaagc ttacaagcaa gttttaccga caactcttac attacaactc     420
tagtctgtag tctttaacgt agacttacta actagtcatt agtggtttaa ttttttaaat     480
tttcatccat atgttttgt tgtagatata aactaaagtc ggtcacattt aataattgtc     540
attatgtccg cgtaaaagtc aattcagcta ttggacattt atgaaatgta agattttctc     600
tctcatttcc ccgtgcgtga agacatgcat tggttttct gtaataatca acaaatccaa     660
acccctttc gatctttatt tggacattgt tagagacaaa atttctctat agtctttttc     720
ctaatttgat accatgtttt tgtttctgca caaatttact cactggttta actaactatc     780
cacttattta tgattttacc attaggcgtc agctagccct agtcaaattt gtaaacaagc     840
caagctatct acataaatcg agatgtcatt aacgttaatc gtcgttaatt cgaatttgaa     900
aacatagata gctttagcag tacaatgggc aatggtaaga agaatagcaa aaggcccaat     960
atttggtttg cagaaattaa agccttaaaa aaaagcccac agatatttgt caaagaaccc    1020
taataacctt ttcggtgctc aagcgccgtt tctagggttt ttctctgagg aagaaagcgt    1080
ttcatttctc tgaatttcat cgaaaa                                         1106

<210> SEQ ID NO 62
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter construct YP0101 as found in
      Promoter Report #70
<220> FEATURE:
<221> NAME/KEY: misc_feature
<223> OTHER INFORMATION: T1 Mature Plant Expression: GFP expression
      observed in the Chalaza, Female gametophyte, Funiculus and
      Micropyle, the Embryo, the Mesophyll of the leaf
<220> FEATURE:
<221> NAME/KEY: misc_feature
<223> OTHER INFORMATION: T2 Seedling Expression: GFP expression observed
in the Hypocotyl root, the Hypocotyl root zone, the Root hair, the
Cortex and Epidermis of the root, the Epidermis and Root hair of
the lateral root, the Epidermis of the root tip

<400> SEQUENCE: 62

```
ttctcgttct ctagaatatt gctggaccgg attaggtcaa tattattggg ccagattaga      60
tattgaattg tcgacgttgc ttacgttacg ttatatcttg tttaagaatt aaacctatcg     120
acttagtctt aattaagaaa acattgcctt aaattctctg gtctgcgacc gttttttttga    180
ccgttaaccc ctaattaaag aaacaaaata attatagaaa gagcactgaa atgtgattat    240
tttaacagta ctcttatgag aaaattcgta cttttttagtt ttttttttgt acaaatctct   300
aagaaaaaca ctactactaa ttaagaaacg tttcaaacaa ttttatttttc gttggctcat   360
aatctttctt tctcggtccg ggactaaccg ttggcaaaaa aaaaaaaaaa gttgacaata   420
attattaaag cgtaaatcat acctctcaaa taaaaacttg aatttggaaa caaagacaac   480
taaaaaactc gaatttaaga gaattcctaa aatcaagtga agtatcatca cttggtaaaa   540
tttcataacc gttggcttct atttctatgt gtgccttggt ttgcaggaga taatatttca   600
tttccaacca atgatattcg tacacatagt caaacaaatg tttgtctttg ttattatatt   660
gagaaagaaa caagaaagag agagagagat agataagacg aaggaagtga agcttccaag   720
cgcccaccgt taaaaatctc gtgtgcaagt ttcaaataca agtggccggt ggtctccata   780
atttgatcgt catccaatta aaaggaaga aaaagcgtgt tttatacaag aaaactcatt    840
aaaatagcaa gtctagaaat atctcaacac taatctacca cgtctattac acacacacac   900
acacacactt gatcttaatt tattttcaag attcaagaaa atacccattc cattaccaca   960
acttgaccac acgcctatat ataaaacata aaagccctttt cccc                  1004
```

<210> SEQ ID NO 63
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0115 as found in
Promoter Report #71
<220> FEATURE:
<221> NAME/KEY: misc_feature
<223> OTHER INFORMATION: T1 Mature Plant Expression: GFP expression
observed in the Funiculus, Inner integument, Megaspore mother cell
and Outer, the Funiculus and Outer integument of the
pre-fertilized ovule, the Seed coat of the developing seed
<220> FEATURE:
<221> NAME/KEY: misc_feature
<223> OTHER INFORMATION: T2 Seedling Expression: GFP expression observed
in the Epidermis of the hypocotyl, root and root tip, the Root
hair of the hypocotyl-root transition zone, the Vascular
of the cotyledon

<400> SEQUENCE: 63

```
atgatgaaca ttctacatat ataattatta tgtttaagca cttagacagc ataaattctt      60
tctaattata taaatctaac cttgttacat tgtacatcta taaattactt gaagaaataa    120
cgagttctat ttcttttttaa aaattaaaaa tactatacca tatctcagtg attaagttga   180
accaaaaggt acggaggaga aacaagcatt tgattcttcc ttatttttatt ttattcatct   240
ctcactaatg atggtggaga aaaaagaaa atacctaaca aacaaatata tattgtcata   300
caaaatatt tctatatttt tagttaatta gtttatattc ctcacttttc agggcttata   360
taagaaagtg agcaaacaca aatcaaaatg cagcagcaaa tactatcatc acccatctcc   420
```

```
ttagttctat tttataattc ctcttctttt tgttcatagc tttgtaatta tagtcttatt    480
tctctttaag gctcaataag aggaggtact attactacac ttctctctac ttttacttgt    540
attttagcat taaaatccta aaatccgttt taaattcaaa ataaaactta gagatgttta    600
atctcgattc ggttttccgg ctttaggaga ataattatat gaaattagta tggatatctt    660
tactagtttc cattcaaatg attctgattt caatctaata ctctcactct ttaattaaac    720
tatatgtagt gtaatttcac actgttaaat ttctaccatg tcatgtatat tagagttgca    780
tagaaaattg taaacatcc atttgaattc gaatgaaaca aaatgtttta aaataaaatt    840
ttggttttta aagaaaaat ctaaaactga attatatcgt ttaaccaagt tgtaaaagtc    900
ataaaacgta gtatcttgta aatcgctctt ccacggtcca aatagacttc tagtaataaa    960
caagtaaaac taattttggt ttcttactaa ttttcacaga                         1000
```

<210> SEQ ID NO 64
<211> LENGTH: 1009
<212> TYPE: DNA
<213> ORGANISM: Arabidopsis thaliana
<220> FEATURE:
<221> NAME/KEY: misc_feature
<223> OTHER INFORMATION: Ceres Promoter construct YP0133 as found in
      Promoter Report #72
<220> FEATURE:
<221> NAME/KEY: misc_feature
<223> OTHER INFORMATION: T1 Mature Plant Expression: GFP expression
      observed in the Guard cell (Gc)
<220> FEATURE:
<221> NAME/KEY: misc_feature
<223> OTHER INFORMATION: T2 Seedling Expression: GFP expression observed
      in the Epidermis of the Rosette leaf and Petiole in the seedling,
      the Epidermis and Root hair of the root

<400> SEQUENCE: 64

```
gtcgattggt attagtccaa taactttcac agttttacta taatataata ttgaaagtat     60
ggttaattga caatagggta tttccactga taatcagtca ccagtaataa taatttgttg    120
ggactagaat caatcacttg agttttaaat tgatatatgc ctagatggtt gttaggacca    180
atattcctaa acaataccaa attttaatat agaaatgtaa aataattcgc cgacacatta    240
tttcgttatt gacattgaat atttcaatga tatcaactct gtttatttac atctatttag    300
tataatttct tgagcaacaa aaaagtagt tttaagtta ttttccctag attttttctat    360 tgtaaaagcc tatatatcac aacaaaaatt aaccattttc tcttttggca agtttaaaat    420
ttttataatg aatataccat tttaaaaaaa aaattatcca aactaaatta accatttcct    480
cttttggcaa caaaaattaa ccatttaaaa aaaaaaaaa aaaaaagtt taaaattttt    540 ataacaacag aaagtaatat tatccaaact atgaataatt aaaaaatctg tccacatacg    600
atcatatatt tctctccacc gacagccgaa acactgtca atggcccacg ttcctctaaa    660
agctgtcgtc ttcggtaata ttttccggta taaactaac ttccgatcac aattacacaa    720
aagccccttt ctcgtttata atcataggct atgattcata gcaaacttac agagttggtt    780
attaagaagt caaaaataca gattccttaa aatattttt ttctgttcat atatttttta    840
tcgagaaaca attacttaaa cataagaagc aagacaagaa ttaatgttct tattaacatg    900
atgctaatat aatcggaaaa caaaatcaaa tcatgataga agggtaaaat ggtcaaatca    960
tcgttcccgg ctcaaatttt actaaaacag ccactagcca gccagatcc                1009
```

<210> SEQ ID NO 65
<211> LENGTH: 1001
<212> TYPE: DNA

```
<213> ORGANISM: Arabidopsis thaliana
<220> FEATURE:
<221> NAME/KEY: misc_feature
<223> OTHER INFORMATION: Ceres Promoter construct YP0137 as found in
      Promoter Report #73
<220> FEATURE:
<221> NAME/KEY: misc_feature
<223> OTHER INFORMATION: T1 Mature Plant Expression: GFP expression
      observed in the Egg apparatus of the ovule and fertilized ovule,
      the Antipodal cells, Central cell, Synergid cell, Egg sac, Egg,
      the Antipodal cells, Central cell, Synergid cell and Egg apparatus
<220> FEATURE:
<221> NAME/KEY: misc_feature
<223> OTHER INFORMATION: T2 Seedling Expression: GFP expression observed
      in the Root hair of the root, the Epidermis of the root and
      Lateral root, the upper and lower portions of the root,
      the Endodermis of the root

<400> SEQUENCE: 65
gtggcacatg ctgaaacccc gagcatctct ccggaagaca cgcgtcgttc gctccaaaga      60
aaacagtcac agctgccgga gaatctccgc cgtcttcttc tgccaccgga aaaactctct    120
ccaccacttt cagtgcccac ctcgtgttat atccactgta tcctcgtagc accatatcag    180
cctaataaaa ttttatgtat caaattttaa gacatagccg aaactacact atactagaca    240
ataataatat gatttgtttc ctgaaaaatt atggtttcat gagaaacatt aatcatctat    300 aaacaaatt agctatggca tcgaagagtt atcaatcaaa actgatgaat ctttacttaa     360
tatatacaac atatctttac cttgcggcgg agaagatcgg cgagagaagc accccagcca    420
ccgtcactaa aggattcttc agtgatgaaa tcaccaaaga gaaaacctt ccgtctcatc     480 atcttccaca caatcttctt gagaaaatct gagagataag aaaggtgtag tggttttgct    540
gaagtgatcg tgtttgattt agtaaagaaa tgctttatt attgttgggg gaaacataaa     600
taaataaagt aaaagtggat gcactaaatg ctttcaccca ctaatcaccg acctttcatg    660
gtttattgtg aaatacactc atagatagac atacaatacc ttatgtacgt aaataacatt    720
ttatttgtcg acacttatgt aagtaacgca tagattattt tctatgtgat tgccactctc    780
agactctcag tttcaaccaa taataacaat aactacaaca acattaatca taaacatatg    840
ctctggttta caattaaagc ttagattaag aaactgtaac aacgttacag aaaaaaaatg    900
ttatttacgt tttgtaagat tagtctctag aatcatcacc gttttttata tattaatgat    960
tctttcttat atataaaacc tttctcgaaa tacccatgaa a                       1001

<210> SEQ ID NO 66
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter construct YP0144 as found in
      Promoter Report #74
<220> FEATURE:
<221> NAME/KEY: misc_feature
<223> OTHER INFORMATION: T1 Mature Plant Expression: GFP expression
      observed in the flower, the Carpel, Stigma and Style of the
      Silique, the Cortex and Epidermis of the carpel, the Guard cell
      of the carpel, the Epidermis and Mesophyll of the leaf
<220> FEATURE:
<221> NAME/KEY: misc_feature
<223> OTHER INFORMATION: T1 Mature Plant Expression: GFP expression
      observed in the Vasculature of the leaf, the Cortex and Epidermis
      of the stem
<220> FEATURE:
<221> NAME/KEY: misc_feature
<223> OTHER INFORMATION: T2 Seedling Expression: GFP expression observed
      in the Cotyledon, Hypocotyl and Rosette leaf of the seedling,
      the Epidermis of the seedling Cotyledon, Hypocotyl and
```

Rosette leaf

<400> SEQUENCE: 66

```
aaacgttgca agattattga ttgtgagaaa gagtgctcaa ggtagtactg atttctgtaa      60
agctcacggt ggtgggaaac gatgttcttg gggagatggg aaatgtgaga aaatttgcta    120
gaggaaagaa gcggtttatg cgctgcgcat aacactatta tgtctcggga gaacaaagat    180
ggaagcaaga gcggtttgat tggaccggga ctctttagtg gccttgtttt tggctctact    240
tctgatcatt ctcagtctgg agctagcgct gtctctgatt gtactgattc tgttgaacga    300
atacagtttg agaataggca gaagaacaag aagatgatga taccgatgca ggttctagta    360
ccttcatcaa tgaaatctcc aagtaattca catgaaggag aaacaaacat ctatgacttc    420
atggttccgg aggagagagt tcacggcggt gggctagtaa tgtctttact tggtggctcc    480
attgatcgaa actgaaagcc atttatggta aaagtgtcac attctcagca aaaacctgtg    540
taaagctgta aatgtgtgg gaatctccga atctgtttgt agccggttac gttatgctgg    600
atcaaaaact caagatttgt tggatattgt tatgctggat cggtggtgaa accacttccc    660
ggttgctaaa taaataaacg tttttgtttt ataatctttt tcactaaacg gcagtatggg    720
cctttagtgg gcttccttta agcgaccaat acaatcgtcg caccggaatc tactaccatt    780
tataggttta ttcatgtaaa acctcggaaa atttgagagc cacaacggtc aagagacaaa    840
aacaacttga agataaaggg ataaggaagg cttcctacat gatggacaac atttctttcc    900
acacaaattc tcataataaa aatcttataa tacaaatact tacgtcataa tcattcaatc    960
tagtccccat gttttaaggt cctgtttctt gtctgataca aat                     1003
```

<210> SEQ ID NO 67
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter construct YP0143 as found in
      Promoter Report #75
<220> FEATURE:
<221> NAME/KEY: misc_feature
<223> OTHER INFORMATION: T1 Mature Plant Expression: GFP expression
      observed in the flower Guard cells and Guard cells of the Sepal,
      the stem Guard cells, the Cotyledon and Radicle of the ovule,
      the Radicle of the torpedo stage embryo
<220> FEATURE:
<221> NAME/KEY: misc_feature
<223> OTHER INFORMATION: T1 Mature Plant Expression: GFP expression
      observed in the the Cotyledon and Radicle of the embryo, the
      Root cap of the mature embryo, the Cotyledon

<400> SEQUENCE: 67

```
atacaacaga tggcagatat cgagttaaat acgtgaatca gccgttacga tattttaaaa      60
ctagaaaatt atttaaaaat attgcaaaat accatttaat ttcattgttc ataaaaaaaa    120
gaaattcaaa aacttaaaaa ctgattcaaa aatttggatt aattctcatt aacagtcttc    180
aacactacaa caacatgttt ctaatttatt ttatatttta ataattaaac aatatatacg    240
tctgcacatt gttgctccga cataatctag tataaaaata gttgcagcat atgtgaaaag    300
caagcagcat ttatcactca atacttttaa ttttatctgt tgtatgtatt aaggttttgt    360
agctttaaga aaacgcttat aatataaaat aacttctaaa agatatttca tgcgtataca    420
ataaatattt gtgaaaaaac atttcgaaaa cgtgtacaat atataaacta ttgtgttatc    480
ttttgacatt caaacaaatg ttgacaatgt aattttatcc atgatatgat tggccaatta    540
```

-continued

```
gctgcgaggt aaaaatccgt atacgagtaa aagtaagata aaatttcgca agaagatttt    600
tagcaggaaa tctaagacaa gtgtcatgaa cgtgtcaatc aacaaacgaa aaggagaatt    660
atagaatcca gattcgacgt accacattaa taaatatcaa acatttttat gttattttat    720
ttttgctctg gcagttacac tcttttttcat tgctccaata aaaaaatcac tcgcatgcat    780
gcatatatat acaccatagt aaactccgcc tcttcttcat tttaaaagta tcagtttaca    840
ctgacacaat ccttaactat tttcctttgt tcttcttcat ctttattaca cattttttc     900 aaggtaacaa ataatctttt taagtcactt ttatactctt taaatcttag attgatatat    960
gaatgcatgt taatatttca agatttatag gtctaccaaa c                        1001
```

<210> SEQ ID NO 68
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter construct YP0156 as found in Promoter Report #76
<220> FEATURE:
<221> NAME/KEY: misc_feature
<223> OTHER INFORMATION: T2 Seedling Expression: GFP expression observed in the root, the Epidermis and Root hair of the root, the lateral root primordial and lateral root tip, the root tip

<400> SEQUENCE: 68

```
ttggtttgca ttgtgaagat ttgtattaac tatagaacat tgaattgatg gtgttaagtt    60
cttacacaag cgtgcttctc ggtttgaact gtttcttttg tatgttgaat cagagcttag    120
tttataggaa ccagagtatc tacttagtca ttctctgatg ctaagtgcta aggttctacc    180
tagttgccct ctaggccctt atgttattga taacttatga agctatttga acacttgatt    240
cttaggagac ctaagttggt acagccagat agagtgtatg ttcttgttct ctatgtgaca    300
ggatcaagct gccacacata gttcaagggt atgctctgtg tgggtttgct cagattgagg    360
acaaatctat acaaggaagt agagtctttg acattttgat gttgtatgat aagaagaaga    420
aaggagagta ataaagaaag agaaaaggga acagaaaca cgtgggagaa catcccaaag     480
aggaagcaca cgcggatctt catgcaaagc tccccgattc tcccatgtgg tccctttctc    540
cctttgtccc cctcctcttt cttcttttct cattttactc ctttttttac cattatacaa    600
cgaatctttt ttatcataat ttttggttt tggtttattt tccaataaca ctttcttggt    660
tacttcccat tctcactttt tcatataaga aactcacttt gggaaactta tgtttgagaa    720
tgacaagtct ttttagagaa agtgatgtaa caaatctaaa gtgattatat aataaccttg    780
cacaatgttt ttgattttttt gtaagattcg aatattaggt ttattattcg tagggaataa    840
acttactttc aaaagcgttc ataagttaat actttcatat atgatcataa gtacggacac    900
tattgttttt tgtttgtttg tgtttattct aaaagaaagt agcttttaat tgaaatgtcc    960
tcggaggcac agtttaaagt tcgagtgtaa cagtttctaa ggca                     1004
```

<210> SEQ ID NO 69
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0158 as found in Promoter Report #77
<220> FEATURE:
<221> NAME/KEY: misc_feature
<223> OTHER INFORMATION: T1 Mature Plant Expression: GFP expression observed in the Epidermis and Vasculature of the flower/pedicle,
the Vasculature of the flower petal, the Epidermis and Cortex of
the stem
<220> FEATURE:
<221> NAME/KEY: misc_feature
<223> OTHER INFORMATION: T2 Seedling Expression: GFP expression observed
in the Shoot apical meristem of the inflorescence meristem,
the Epidermis and Vasculature of the rosette leaf and root,
the Hydothode, Epidermis and Vasculature of the cotyledon
<220> FEATURE:
<221> NAME/KEY: misc_feature
<223> OTHER INFORMATION: T2 Seedling Expression: GFP expression observed
in the seedling, the Epidermis and Vasculature of the hypocotyl,
the Epidermis and Root hair of the hypocotyl/root

<400> SEQUENCE: 69

```
ttattagatt aatagattgc attgcattgc ttgtgctttc aatttacaaa ttgtctccca      60
actccatcga cacatctctt tttgtgtata taagattcag acttgttata ttttttttat     120
aaatatgtta ttagcatctt aagttaaatt gatttttat atctgcatta aggattacac      180
gactatattt gcgattgtgt gttggttaaa atataattta ggattgtctt taactacatt    240
taggattata tgactatatt tggttaaata taaaatctag ctgtgattat tagtattcaa    300
aaataagtag cctaaccaat taaaacaacg gctattgggg caaattagaa cattttagtg    360
tgtccaaaat ataatggtca ttaggtcata ttcctcctag cttcatcgca gcataattga    420
atgattgcct tatttagaag agcttttcca ctttcccaaa atctaggtgg gatcttttg     480 ttttgacctt catttttctt gtttaccatt tttagctaaa ttatttacga ttacaaaaga    540
tatcaaaagt tggatcataa tacaatttat agacttactg tagaaaattc gtatgtacaa    600
gtacaacaaa ttcttcataa taaattttga aaattctatt acaaatgttg taagaaatag    660
aatttgaaat atatataaac taaggagaaa aaaaagaga acatgcattg ctctagtcag     720
agtggaccaa catcaacgag ataagataac ataaaaacca actcaccata actaaaaaca   780
tcccaagaga tccaacgatt catatcaaac acaaaaacat cgaacgatca gatttaaacc   840
atctctggta tctccaaaac acaaacactt ttttttttct tttgtctgaa tggaacaaaa    900
gcatgcgaca tctctgtgtc tttatcttct ctctcctctt cttgaaaaac tgaacctta    960 attctttctt cacatctcct ttagctttct gaagctgcta                         1000
```

<210> SEQ ID NO 70
<211> LENGTH: 997
<212> TYPE: DNA
<213> ORGANISM: Arabidopsis thaliana
<220> FEATURE:
<221> NAME/KEY: misc_feature
<223> OTHER INFORMATION: Ceres Promoter construct YP0164 as found in
Promoter Report #79
<220> FEATURE:
<221> NAME/KEY: misc_feature
<223> OTHER INFORMATION: T1 Mature Plant Expression: GFP expression
observed in the Epidermis and Vasculature of the inflorescence,
the Sepals and Shoot apical meristem, the Vasculature of the
stamen filament, the Nectary and Ovule of the flower
<220> FEATURE:
<221> NAME/KEY: misc_feature
<223> OTHER INFORMATION: T1 Mature Plant Expression: GFP expression
observed in the Epidermis and Cortex of the silique, the Placenta,
Ovule and Funiculus of the ovary, the Outer integument of the
ovule, the Embryo of the ovule at the globular stage
<220> FEATURE:
<221> NAME/KEY: misc_feature
<223> OTHER INFORMATION: T1 Mature Plant Expression: GFP expression
observed in the Embryo and the Root apical meristem of the embryo
at the heart stage, the Embryo at the torpedo stage, the Root
apical meristem of the mature embryo
<220> FEATURE:

<221> NAME/KEY: misc_feature
<223> OTHER INFORMATION: T1 Mature Plant Expression: GFP expression
     observed in the root tip, the Pith, Cortex and Vascular bundle of
     the stem
<220> FEATURE:
<221> NAME/KEY: misc_feature
<223> OTHER INFORMATION: T2 Seedling Expression: GFP expression observed
     in the Epidermis, of the hypocotyl, the Lateral root and
     Vasculature of the root, the lateral root tip, the Pericycle and
     Vasculature of the lateral root initial
<220> FEATURE:
<221> NAME/KEY: misc_feature
<223> OTHER INFORMATION: T2 Seedling Expression: GFP expression observed
     in the lateral root primordial, the Root apical meristem
     of the root tip

<400> SEQUENCE: 70

```
gtcgattggc attactagag ttttagattt cacagaattc ttttctttgt ttggtctgtt    60
cgtcctctac tgtgttttc ttttgttttg gctattttgc cgtctgttaa aaaattgggg   120
ttttccgata atgtattgta tatgcctgaa ttatggaaat atcactaaaa acactttttt   180
gcacttttgt atatattgca attaagattt aattttttcta ttttgaagac ttttttgttaa   240
aagagagatt tgctaactca aaattaccgg agttaataag ttcgttctca tcagattagc   300
aaaacattca tctttaaaga aatctgttta tctcacgtaa aattctacta attggcagca   360
gcacactact ttaatgggcc tattactatt tcaatatgca ctgaaaactt cattggactg   420
tccaataaca ttataacatt attaaaacta aactacattt gtatttgggt tacaattta   480
taaagagtaa gactcaagat actaattggg ctgcagacaa ctttaaaagc cttactacaa   540
aaatcaaaac cattcttaat taactaacaa ccaggtaaaa atctcagtac aatatttaca   600
ctaaaaatag gtgccaccca ctatgcaaaa gtttagggcc acgaacaaaa aaacctgtaa   660
attgttatgt cttcacaata tgtgttttaa tacacatgaa ttttagctgc ggttaatgta   720
aattttgtag ttaaattaag gctaaacaat ctcaaatata aattggtcag gtccacagac   780
aacagcctgg caagtggcaa gcactaaaaa ttcgaccgtt attttttgcc cctttttta   840
atatttcgaa attgtatctt ttagttttat tttaaagctt tttagcccgc tcctcctccg   900
ctccaccttt aattttttca ccaattggat ttggatctgt caaaaatatt ggcctcttc    960
tctctttctc tcttgctctc tttctttgtt gggttga                           997
```

<210> SEQ ID NO 71
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0119 as found in
     Promoter Report #80
<220> FEATURE:
<221> NAME/KEY: misc_feature
<223> OTHER INFORMATION: T1 Mature Plant Expression: GFP expression
     observed in the silique the Inner integument of the ovule, the
     Endosperm and Inner integument of the ovule ath the torpedo stage,
     the Outer integument of the ovule at the zygote stage, the Inner
     and Outer integument of the ovule
<220> FEATURE:
<221> NAME/KEY: misc_feature
<223> OTHER INFORMATION: T1 Mature Plant Expression: GFP expression
     observed in the Seed coat of the seed

<400> SEQUENCE: 71

```
taccaaaaat aaggagtttc caaagatgg ttctgatgag aaacagagcc catccctctc    60
cttttcccct tccatgaaa gaatcggat ggtcctcctt caatgtcctc cacctactct   120
```

-continued

| | |
|---|---|
| tctcttctttt ctttttttct ttcttattat taaccattta attaatttcc ccttcaattt | 180 |
| cagtttctag ttctgtaaaa agaaaataca catctcactt atagatatcc atatctattt | 240 |
| atatgcatgt atagagaata aaaagtgtg agtttctagg tatgttgagt atgtgctgtt | 300 |
| tggacaattg ttagatgatc tgtccatttt tttctttttt cttctgtgta taaatatatt | 360 |
| tgagcacaaa gaaaaactaa taaccttctg ttttcagcaa gtagggtctt ataaccttca | 420 |
| aagaaatatt ccttcaattg aaacccata aaccaaaata gatattacaa aaggaaagag | 480 |
| agatattttc aagaacaaca taattagaaa agcagaagca gcagttaagt ggtactgaga | 540 |
| taaatgatat agtttctctt caagaacagt ttctcattac ccaccttctc cttttgctg | 600 |
| atctatcgta atcttgagaa ctcaggtaag gttgtgaata ttatgcacca ttcattaacc | 660 |
| ctaaaaataa gagatttaaa ataaatgttt cttctttctc tgattcttgt gtaaccaatt | 720 |
| catgggtttg atatgtttct tggttattgc ttatcaacaa agagatttga tcattataaa | 780 |
| gtagattaat aactcttaaa cacacaaagt ttctttattt tttagttaca tccctaattc | 840 |
| tagaccagaa catggatttg atctatttct tggttatgta ttcttgatca ggaaaaggga | 900 |
| tttgatcatc aagattagcc ttctctctct ctctctagat atctttcttg aatttagaaa | 960 |
| tctttatttta attatttggt gatgtcatat ataggatcaa | 1000 |

<210> SEQ ID NO 72
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0171 as found in
      Promoter Report #82
<220> FEATURE:
<221> NAME/KEY: misc_feature
<223> OTHER INFORMATION: T1 Mature Plant Expression: GFP expression
      observed in the Stigma and Style of the distal silique, the
      Carpel of the proximal silique
<220> FEATURE:
<221> NAME/KEY: misc_feature
<223> OTHER INFORMATION: T2 Seedling Expression: GFP expression observed
      in the Vasculature, Pericycle, Endothelium and Epidermis
      of the root

<400> SEQUENCE: 72

| | |
|---|---|
| aatgaaaaca atgggagaag tacatgcttg tcctcacaca ctaatgccga tgaggaaagc | 60 |
| ctttaagggg acttttatct ccgcaggagg tttcacgagg gaagatggga atgaggctgt | 120 |
| gtcaaaggga agaactgatt tggtggctta tggtcgatgg tttctagcca acccggacct | 180 |
| gccaaagagg ttccaagtgg atgcaccgct gaataagtac gatagaccaa cgttttacac | 240 |
| ttctgatcca gtcgtcggtt acaccgatta cccttcctc gaatcaacag cttaaaattg | 300 |
| ttatcaataa tgtaatgtag tgtgtttccc ttatataaga tgtaataagt ttctggcttt | 360 |
| tcatttatac ttttaagtt taagtcataa aaccttcaca aaaatttcca cggacacatt | 420 |
| atcacaaaag cgctttctag agaccaacat aacttaactt gattgttgat ttctgtttga | 480 |
| tgtgatcatg ccgcaatcca gtgtgttctc atgatgctat cttccctcct ttcacatgct | 540 |
| gcacagaaca aaacagagca ttttcctccc aactatacct aattttttt ggtcggtggt | 600 |
| caaagttata catcggaaga atctgttgaa atcatattga ggcccctcat ttgttatgtt | 660 |
| atgtaatctc caatggatca aaagtagaat cccaactgta gaagatgata ctatcatgct | 720 |
| aggtagaaga cagcatggaa tatgggtaa gttcaaagtg gttacactct aatgtcgtct | 780 |
| caacgaatac gtctttatga agaaataaaa aaatctaagt ggttggatgc gtcatcaatg | 840 |

| | |
|---|---|
| acgaccacgt cgttaaagac agaaagaaac acttgcgttc ctgattctct gatcaatcaa | 900 |
| tgtgtataaa tatgttcgga tatgtccatt atcttacgca atcttgaaaa gtgtttttga | 960 |
| gagaaatata ggttttacaa aatccaccgt tgtgaattca | 1000 |

<210> SEQ ID NO 73
<211> LENGTH: 1005
<212> TYPE: DNA
<213> ORGANISM: Arabidopsis thaliana
<220> FEATURE:
<221> NAME/KEY: misc_feature
<223> OTHER INFORMATION: Ceres Promoter construct YP0188 as found in
      Promoter Report #84
<220> FEATURE:
<221> NAME/KEY: misc_feature
<223> OTHER INFORMATION: T1 Mature Plant Expression: GFP expression
      observed in the Guard cell, of the Pedicel and Sepal, the Placenta
      and Funiculus, the Suspensor of the early globular embryo
<220> FEATURE:
<221> NAME/KEY: misc_feature
<223> OTHER INFORMATION: T1 Mature Plant Expression: GFP expression
      observed in the Suspensor, Embryo, Hypocotyl, Outer integument,
      the Suspensor and Embryo of the early heart stage embryo, the
      mid-heart, late heart and torpedo stage embryo
<220> FEATURE:
<221> NAME/KEY: misc_feature
<223> OTHER INFORMATION: T1 Mature Plant Expression: GFP expression
      observed in the leaf Epidermis, Mesophyll and Vasculature, the
      Cortex, Epidermis and Guard cell of the stem
<220> FEATURE:
<221> NAME/KEY: misc_feature
<223> OTHER INFORMATION: T2 Seedling Expression: GFP expression observed
      in the Vasculature, Epidermis and Root hair of the hypocotyl-root
      transition, the Vasculature, Hydathode, Epidermis,Mesophyll of the
      rosette leaf
<220> FEATURE:
<221> NAME/KEY: misc_feature
<223> OTHER INFORMATION: T2 Seedling Expression: GFP expression observed
      in the Vasculature and Epidermis of the root, the Pericycle of the
      Lateral root, the lateral root primordial

<400> SEQUENCE: 73

| | |
|---|---|
| gattggtatg aaatttcgga gaccaacaaa aaaaacttta ttgagcttgg agtgaagcta | 60 |
| tatatatggg gcaagatcat aatatgttta tatcggcctt ttcgttaact gaaaataata | 120 |
| gttttgagaa atatatcaaa tggtaaacag acatcatctt tgaaaaatac catcaatgaa | 180 |
| gttaatattg ttattggcat atggtttacc catcttaatt ttaatgcaac caaacaaaca | 240 |
| agaaacaaaa actgtataag atacaaggtg ttttacgatt ttccgtctta aaaccgaaat | 300 |
| attttgttc ctacgactt aaacggactt tgcttaagtt gtgtgcatgt aagctcgtcg | 360 |
| tccctcgatt gtcatcaaca ttcaccaata tcagcctcta tcacacgagt gaaggtggtg | 420 |
| attcggctta atgaaaacag agaaatattt caatatgatt cctattaaat tttaaatctt | 480 |
| ttttctcaat ctctagattt tcattaaaag catcatgatt tttttccact atgttcatat | 540 |
| atctctatca cagttttagg tacattgtag aaattggata agatacgtca tacgtctaac | 600 |
| atgaatttgg tctagcaagg aaggtttgag ataataagtg aaaagaaaac acaagataat | 660 |
| aaattataat ttataaatgc tttatagtat tgaaaaataa gatgattttt ttttttttta | 720 |
| ataccggatt ggctgatcca cttatgatga ctcaaatgtt attaagtttc aagacaattt | 780 |
| atgatgacac aaatcacaat gagtcaatag tagccacgaa gccagaaaaa aaaaatgtac | 840 |
| tacaaaaaga taatgatagt acaaaatgat acgtcgtact gccacatgta cgacacaact | 900 |
| cgattaccaa aaagcagagc catccaacca taaaactcaa aacacacaga ttccactggc | 960 |
| gtgtgctctc ctcacttcac tcgtccttga aacttgaggt actga | 1005 |

<210> SEQ ID NO 74
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0258 as found in Promoter Report #85
<220> FEATURE:
<221> NAME/KEY: misc_feature
<223> OTHER INFORMATION: T1 Mature Plant Expression: GFP expression observed in the Epidermis, Guard cell and Vasculature of the Sepal
<220> FEATURE:
<221> NAME/KEY: misc_feature
<223> OTHER INFORMATION: T2 Seedling Expression: GFP expression observed in the Epidermis, Hypocotyl and Root hair of the hypocotyl root transition, the Epidermis of the root

<400> SEQUENCE: 74

```
taaataactt acttaaattt atattaaaac cgtttacatc tgatataatt taaaaggttt      60
tagacgaatt agtattagtg aaccattatc aagatgtatt tattcaaaaa tctataataa     120
taaaaacaaa actgggaaag caatgggaag aagatctgat tggctttgga agacttcgcg     180
tgttaataag attttctca aaaagaaag atcggacggc aatgcgtggc aagtcgctta      240
tgacgtcgga agcttagctt gccacgtgta cggtcatcac catttaggtg accgatataa     300
tgtatttccc gtgacttgac aatctaatct cccaatttat cgtgctccag tgtctcaaga     360
gagaacttac tctattggtt acccaaaact cacataaaac gtggatttta tattttttt      420
tatcaaataa tttgatgtgc aatataaaca tatatgtatt attatcttgc atgtttaaaa     480
aatgctaact taaatttttc ttcaatgatt gagattttc atacacatcc atcgagttca     540
cacttatgat taaacaaagt gtattgttac actaataacg gttctaagtt gtttcaatac     600
gtttatgata acggttctat actaatacta gtattcatac gtttatgaaa ctcgttaatt     660
atatatttaa ctttgtttag ctgtatcata acaagcgttt taagaaataa tttaataaaa     720
aatgagaaaa cgataagcga cgccttatcg cctatgtgta attatcgtgt caaaatatcg     780
tgataaggaa gctgtttcag aggagccttc tcgtttgttg cgtcgttgct ctgagccaac     840
aacgctaata taaaggaag ctcaagtctc tctgttttaa tctcggacca atatacaaaa      900
ccgtgtgttc ttctctgtat cttattaaat caaaaccaat tttgttcttc ttctttgatt     960
cttttttcct tcattttta acgtatcttg agagatcgac                           1000
```

<210> SEQ ID NO 75
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0265 as found in Promoter Report #86
<220> FEATURE:
<221> NAME/KEY: misc_feature
<223> OTHER INFORMATION: T1 Mature Plant Expression: GFP expression observed in the inflorescence meristem, the Epidermis and Vasculature in the Sepal of the inflorescence, the Epidermis and Vasculature in the Petal, the Vasculature in the Filament of the stamen
<220> FEATURE:
<221> NAME/KEY: misc_feature
<223> OTHER INFORMATION: T1 Mature Plant Expression: GFP expression observed in the the Guard cell and Vasculature in the silique, the Guard cell in the Style of the silique, the Cortex, of the Carpel in the silique
<220> FEATURE:

```
<221> NAME/KEY: misc_feature
<223> OTHER INFORMATION: T1 Mature Plant Expression: GFP expression
      observed in the Guard cell, Septum and Vasculature of the proximal
      silique, the Placenta, the Funiculus, the Placenta of the ovary
<220> FEATURE:
<221> NAME/KEY: misc_feature
<223> OTHER INFORMATION: T1 Mature Plant Expression: GFP expression
      observed in the the outer integument, Funiculus, Placenta and
      Vasculature of the pre-fertilized Ovule, the Embryo of the
      fertilized ovule the Hypocotyl of the heart stage embryo
<220> FEATURE:
<221> NAME/KEY: misc_feature
<223> OTHER INFORMATION: T1 Mature Plant Expression: GFP expression
      observed in the the Outer integument of the fertilized ovule, the
      adaxial and abaxial leaf, the Epidermis and Vasculature of the
      stem
<220> FEATURE:
<221> NAME/KEY: misc_feature
<223> OTHER INFORMATION: T2 Seedling Expression: GFP expression observed
      in the Root hair of the hypocotyl root transition zone, the
      Epidermis of the cotyledon, the Epidermis and Trichome of the
      rosette leaf, the Epidermis and Root hair of the root, the root
      tip

<400> SEQUENCE: 75
gtcgattggt ttttttttta cggtttcctg caaattaatc catttaaaac aaatcctcca        60
ttgttttgta taatgttgga gattagtagg attagtcgga taatatggca taaacataat       120
atgatgctaa attctaaaga aacgatatga ataaataatg cagcagtata aaaactgtac       180
cattgcgtgg gtggaggatt ttaggtcatt gttagggcac tttcatgggg accatttccg       240
ccttaacgaa gacttattac acacaaccgt caatgtgggc tggaaacttg cagtgcaatc       300
cggtctggtc ctataatttta tggccggtta gggtttacaa gtttttaatc tatcaattaa      360
atgagatgga cacaaaatgt aatcaccagt ggaaaagaaa acattacgag acttatacaa       420
tgtctacaag aagactcgag tggggcaaca tgttgtacat aatccgacgt cgttttggga       480
gtcagtaaat aaagttcgag aaatgacgtc gttttgaagt catccgagag aaaatgactt       540
aaagtgaccg acgttgtttt gaagtcagcg gaagagtaaa gaagtaagaa acgaagtcgt       600
tttgaagtca tctcttcaga tatgtttgtt ctaattaaaa tttcccaagt gggaattagt       660
ttgtaattga aggtatgcac gatttttagt tacaatttta attcttcttc ttcagatcca       720
agaactctca gtctctgcgt tcacactctt tctttgaatc cttcatcatc ctaattcatc       780
tccaagaact gaatcagaag ttgtatttcg ctaattcaac ttttccaggt aattttccat       840
tcctcgatta ttcgaatttg ggtattaaat cataatgcat cgggaaattt ggattcttta       900
ggataatttt tccggcaaat ccgattattg agctagtttc tgaatgttta gattctcagt       960
gtctgtcaat taggtttttga ttttggaagt agagaagtta                           1000

<210> SEQ ID NO 76
<211> LENGTH: 986
<212> TYPE: DNA
<213> ORGANISM: Arabidopsis thaliana
<220> FEATURE:
<221> NAME/KEY: misc_feature
<223> OTHER INFORMATION: Ceres Promoter construct YP0071 as found in
      Promoter Report #99
<220> FEATURE:
<221> NAME/KEY: misc_feature
<223> OTHER INFORMATION: T1 Mature Plant Expression: GFP expression
      observed in the flower bud and inflorescence meristem, the Cortex
      of the Receptacle and the Vasculature of the Sepal, the
      Vasculature of the leaf and mid-vein rib
<220> FEATURE:
<221> NAME/KEY: misc_feature
<223> OTHER INFORMATION: T2 Seedling Expression: GFP expression observed
      in the Vasculature and Cortex of the hypocotyl, the Vasculature
``` and Guard cells of the leaf, the Epidermis and Mesophyll
of the rosette leaf, the Vasculature of the petiole
<220> FEATURE:
<221> NAME/KEY: misc_feature
<223> OTHER INFORMATION: T2 Seedling Expression: GFP expression observed
in the Vasculature of the root transition zone

<400> SEQUENCE: 76

```
ataggcccta cttctaatta aagcccattt acttctctcc ttgtcttctt attcctcttt      60
tctccccatc acgtgacgac gatgctataa acgccgtcgg attatataac tggtgccgtt     120
gacaagacgg cgacagaaga aagaaagaag aaaccacagg ctctagggaa cgtaacgtta     180
tgtcctgtct atagcattta taacggtcag atcaacgccg tttagataaa gatctgtcaa     240
tgttaaagaa gagatgcatc tctacaccgt taaatttaaa acgccgtgaa cctcttatct     300
attgattttt gtttgatgaa gccaaaacaa atcgtgtcag aagacttatc agagaagaag     360
aaaacgacga cgttcccgtt tctccatgtc taataagtgt agtagtggcg gctactaaaa     420
actctaaagt ttgactccag taaaactgcc tttctagtgt aattccagtg attttagagt     480
ttgaatagtg tgtgaccaaa tttgaaagta caatctcagc aatattattg atcactcgtt     540
ataaaagaat cgaatgtaaa aatagccaat gagagactga gacgtatgtg tttgaccata     600
agtcgtatag tttgtatcta tctacctgca agatcagcag atggttctct gatcaattgt     660
accttaatta tcttttattt tcgtaaaatt tctctattca caaatgataa atctacttaa     720
gacagtaacc ataacaagat ttacaagata atttgaaaaa tgaacacata aaagtatttt     780
ggcgcattat ttttaataat aacaatattt atgtaaagtc acataaaagt atatattcgc     840
tcacaaagtc ttacggtatt tagaacagta gtaccacatc gattctcttc atcttcttct     900
tcataatatg ccattgttca tgtctctgtg tcctatcgca taacactcac gctatcttat     960
tattttctct cgctctttct cactga                                          986
```

<210> SEQ ID NO 77
<211> LENGTH: 1100
<212> TYPE: DNA
<213> ORGANISM: Arabidopsis thaliana
<220> FEATURE:
<221> NAME/KEY: misc_feature
<223> OTHER INFORMATION: Ceres Promoter construct YP0214 as found in
Promoter Report #100
<220> FEATURE:
<221> NAME/KEY: misc_feature
<223> OTHER INFORMATION: T1 Mature Plant Expression: GFP expression
observed in the Anther, Petal and Sepal of the inflorescence
meristem, the Anther, Silique, Ovule, Placenta, Petal and Sepal
of the, the leaf, sepals of floral primordial
<220> FEATURE:
<221> NAME/KEY: misc_feature
<223> OTHER INFORMATION: T2 Seedling Expression: GFP expression observed
in the Root hair and Vasculature of the hypocotyl-root transition
zone the Epidermis of the hypocotyl, the Epidermis and Vasculature
of the root, the Epidermis and Vasculature of the cotyledon
petiole
<220> FEATURE:
<221> NAME/KEY: misc_feature
<223> OTHER INFORMATION: T2 Seedling Expression: GFP expression observed
in the Epidermis, Mesophyll and Vasculature of the rosette leaf,
the Epidermis, Vasculature of the Cortex, Endothelium,
Pericycle, the primary root cap

<400> SEQUENCE: 77

```
ccagtcgatt ggcgcctcgc atgcctatca tatttaaccg tcaataatgg atttggcggt      60
tttggtaggc cgggtcaacc ggattaaaag aaaacggttt ggagtccttc cttgcaattg     120
aattttcaca cattcgggtt ttgtgatttc tctgtcataa tgggcccggc acatatggtt     180
```

```
cataacccat gtgggcctat ggtataattt ttccaattaa aactattgtt aggtcgataa        240
aacaaaaaac aataaaaacg agtggaatac acataccaaa aagaatgtga tgaacattag        300
taattttatt ttgatggtta atgaaaaaca aaataaatgc atcttggcat cttccgttgg        360
aaagcgcaaa tagggcagat tttcagacag atatcactat gatgggggt gagagaaaga        420 aaacgaggcg tacctaatgt aacactactt aattagtcgt tagttatagg acttttttt         480 tgtttgggcc tagttatagg atcataaggt aaaaatgaag aatgaatatt agattagtag        540
gagctaatga tggagttaag tatgcacgtg taagaactgg gaagtgaaac ctcctgtatg        600
gtgaagaaac tatacaacaa agcccttgt tggtgtatac gtattaattt ttattctttt          660
atcacaagcg atacgtatct taagacataa taaatatata tcttactcat aataaatatc        720
ttaagatata tatacagtat acacctgtat atatataata aataggcata tagtagaaat        780
taatatgagt tgttgttgtt gcaaatatat aaatcaatca aaagatttaa acccaccat         840 tcaatcttgg taagtaacga aaaaaaggg aagcaagaag aaccacagaa aaggggcta         900 acaactagac acgtagatct tcatctgccc gtccatctaa cctaccacac tctcatcttc         960
tttttcccgt gtcagtttgt tatataagct ctcactctcc ggtatatttc cccattgcac       1020
tggacactct catcttcttt ttcccgtgtc agtttgttat ataagctctc actctccggt       1080
atatttcccc attgcactgg                                                   1100

<210> SEQ ID NO 78
<211> LENGTH: 990
<212> TYPE: DNA
<213> ORGANISM: Arabidopsis thaliana
<220> FEATURE:
<221> NAME/KEY: misc_feature
<223> OTHER INFORMATION: Ceres Promoter construct YP0216 as found in
      Promoter Report #101
<220> FEATURE:
<221> NAME/KEY: misc_feature
<223> OTHER INFORMATION: T1 Mature Plant Expression: GFP expression
      observed in the Epidermis of the inflorescence meristem, the
      Embryo and Placenta of the ovule, the Vascular bundle (Vb) of
      the stem
<220> FEATURE:
<221> NAME/KEY: misc_feature
<223> OTHER INFORMATION: T2 Seedling Expression: GFP expression
      observed in the Epidermis, Mesophyll, Hydathode, the Epidermis,
      Mesophyll and Vasculature of the rosette leaf
<220> FEATURE:
<221> NAME/KEY: misc_feature
<222> LOCATION: (453)..(453)
<223> OTHER INFORMATION: n is a, c, t, g, unknown, or other

<400> SEQUENCE: 78
ttttgtttct aatagtttga tgtttatatc aacattatta tttactttca tttgttaccg          60
atagaaagag gagaaaattg ttgacaaaaa caaagataaa agtaaaatta atattattaa        120
attaataaaa ataacaaact gtaaaagcta ttttttaaa aattttgtgt aaaacatcta         180
aaaattattc ttttagaaac agaagaatat cattgaagat aatagtgtga aattatatat        240
atatatagaa atatataaag taggattttt ttctgtatac aaatatacgt ttccaatttt        300
atcaaaaact gtaaagattt ttttctttgt cagtacctgc taaacttgtt aattttttta        360
ttaaaaaaaa atcaaattac aattcttcta taatcatttt aaattccatt tctttatacc       420 acaaagatt atattgcctt tatcgtctttt ggnatgtatg cgtgaatata tttattatt         480 ttcttttctt tcattttctt tttaaagaac tttataaatg aaataaggaa caaacaatat       540
acatatgtac taacgtatat aaataatatc atcaatatct atccaaaact tggatttcat        600
```

-continued

```
ggttgacgtg gcccaaccaa aatctcaagt tctctgcgga tgacgaacca tctcaccatc    660 tcttttttc tctctctttt tttttttaat atcatcagca cggttacata aaattcgtga    720
tccatgaagt tggctttctt gtcgttttac ttcatcaccc catttttta aagtctccat    780 ctttatactt cttcaactct ccaccaccac cattgtcacc accacattta aacacacact    840
ttcacttgta gtgggattag aaagtgcgtt ttattcattt gttttactgt ttttgataac    900
ctcaaaattt gcctaaattt tattctctat aaatccttat atgttttact tacattccta    960
aagttttcaa ctttcctgag cttcaaaaag                                     990
```

<210> SEQ ID NO 79
<211> LENGTH: 984
<212> TYPE: DNA
<213> ORGANISM: Arabidopsis thaliana
<220> FEATURE:
<221> NAME/KEY: misc_feature
<223> OTHER INFORMATION: Ceres Promoter construct YP0271 as found in
      Promoter Report #102
<220> FEATURE:
<221> NAME/KEY: misc_feature
<223> OTHER INFORMATION: T1 Mature Plant Expression: GFP expression
      observed in the Megaspore mother cell, Outer integument and
      Funiculus of the ovule, the Suspensor cells of the globular
      embryo stage in the ovule, the Suspensor apparatus

<400> SEQUENCE: 79

```
atctctgatt ttttttatca ggaacaagta aataaatagc tttgagtttt tgttttttt     60 ctacattctt cgcccaaaag atgtaagaaa ataaggatt tgaaaccttg ttctgttgtt    120
actcctttaa attcttagaa actataaatc attatatctt tgatctgttt cacaaactaa    180
tcatattcgt tgcaaagtga gaattcgtcc cactttactc tttacaccga tactagtatt    240
atagatgtac agcatagtat tccatatcta gttatttagt caaaactcta tatattaaga    300
ggtaggttaa ttaattaagg agtaattgaa gattatagaa agaataaaaa ataccattta    360
atggacagaa ccaaagataa ctaactatca tactataatg ttgaatttct tccacgatcc    420
aatgcatgga taacaacatc aatcaaatca tacattcatg ctatataaca tagttttcag    480
ttacaaactc tcttttttat ttatttcagt tgttcctttt catgaccata ttaacatcaa    540
ataatgcatt tttttcaacg tctcttgact tacacccact aatattgaca aattgaacat    600
ctatacgact atacgcacat aagttaaaaa tgcatgcaag tgctaaggga atttataaca    660
tctaaggtta ataagactaa gaaagtataa aataagaata cgtattatga atttatgata    720
tactttacta atcttttga aaaatacttt aatttaatct actataggg gtaaaaagta     780 aaaaagaaat aaagatacgt ttatccgcat atagtacctg gaaataacag aaaataaaaa    840
cacaggtaag tactttgcct gagctagtat atgaacacta aagagataca cacacacaaa    900
aagagagcag aaacaaaaca cacacactta aagctttcgt ctttacctct tcccttctct    960
ctctctatct aaaagagtt ccga                                            984
```

<210> SEQ ID NO 80
<211> LENGTH: 979
<212> TYPE: DNA
<213> ORGANISM: Arabidopsis thaliana
<220> FEATURE:
<221> NAME/KEY: misc_feature
<223> OTHER INFORMATION: Ceres Promoter construct YP0279 as found in
      Promoter Report #103
<220> FEATURE:
<221> NAME/KEY: misc_feature
<223> OTHER INFORMATION: T1 Mature Plant Expression: GFP expression observed in the Embryo, Embryo sack and Micropyle of the
fertilized ovule, the Embryo proper and Suspensor of the zygote
<220> FEATURE:
<221> NAME/KEY: misc_feature
<223> OTHER INFORMATION: T1 Mature Plant Expression: GFP expression
observed in the Micropyle pole of the ovule, the fertilized ovule,
the Radicle and Root apical meristem of the torpedo stage embryo
<220> FEATURE:
<221> NAME/KEY: misc_feature
<223> OTHER INFORMATION: T2 Seedling Expression: GFP expression observed
in the Epidermis, Guard cells and Mesophyll of the rosette leaf,
the root and root transition zone, the Pericycle of the
lateral root initials, the lateral root primordia

<400> SEQUENCE: 80

```
cgctttatta taggtttaac aattgatttt tcattattt gttttcaatc tccaaatcat      60
ttctcaataa ctctcaaaca ttgtttaaag cttttttct taattaacat tataacaaaa    120
aaataaatag agaaatttac tttgattcaa acaccagtca ttgtagatta gccaagagtt    180
ttcagtaaca aaatttacct tataaacctt ttgaatggct atttctgaaa tggaatagaa    240
atctttagtc gtggaagtat ctctatccat aagaaaactc gttttacaaa gtaattttaa    300
atcaatacaa aaaagtgaaa aaatccactg gtggacccca ttcattccag aattgccgat    360
tacgagctat cttgtccctt cttcaccatt cgctcactct ctctctctct ctctcgtctt    420
cttcttccca ccactctctc tgtttctcca caacttctct tctcaaagtt aaaattaccc    480
ctaaaccaaa aaaaaaaaaa cgctcttcac tatttattta ctaaactctc ctttgtttgt    540
tactaagctc tcactaaaac cctaatcttt ctcctcttat atatctcgtg actcttcttt    600
ctcctccaat ctctctctcc ctcttcacaa accaattagc ttctttctgt aaaacctcac    660
tcgttggcca attcttttgg ttttcataca cataaatctc agattccaaa tgggttttct    720
tagctctttc tttcaaatga tgaacatttg ttagcagaat cttcctcatt ccctaaagtt    780
ttgatctttt tttcccccttt caattttgta ttttctcacc aaataaaaaa aggtttcttc    840
agtgggtttt aagggtttat tattatctta aaattaaaca caattcttta atcaaaaggc    900
aaaaatctta atttcatcac tctcttctca ctcacaaaag ttcttacaat cttcaaagtt    960
ttggtcttgt ttcttttcc                                                 979
```

<210> SEQ ID NO 81
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter construct YP0285 as found in
Promoter Report #105
<220> FEATURE:
<221> NAME/KEY: misc_feature
<223> OTHER INFORMATION: T1 Mature Plant Expression: GFP expression
observed in the Vasculature of the leaf, the Embryo sack of the
pre-fertilized and fertilizad ovule
<220> FEATURE:
<221> NAME/KEY: misc_feature
<223> OTHER INFORMATION: T2 Seedling Expression: GFP expression observed
in the Vasculature of the hypocotyl, the Vasculature and Epidermis
of the root transition zone, the Hydathode and Vasculature of the
cotyledon, the Pericycle, Vasculature and Epidermis of the root

<400> SEQUENCE: 81

```
gggattatat atgatagacg attgtatttg cgggacattg agatgtttcc gaaaatagtc      60
atcaaatatc aaaccagaat ttgatgtgaa acactaatt aaaacatata attgacaact    120
agactatatc atttgttaag ttgagcgttg aaagaaaatg aaagagtgta gactgtagta    180
```

```
cgtatgagtt tcccaaaaga tggtgcttga atattattgg gaagagactt tggttggttc    240
ggttgaatga agattttac ctgccatgtt gatagagaaa ggcaaataaa tgtagggtc      300 gatgtctaac gtaaagactg gatcaaccaa gagtcctcct cctcgtcttc accaaaaaaa    360
aagagtcctc ctcgtggaaa cttatttctt ctccagccaa gatctcatct catctcttca    420
ctctatgaaa tataaggaa tcttatggtt tttctaaaaa ctatagtacg tctatatacc     480
aaaggaaaca atataaaatc agttaatctg ataaattttg agtaaataat aaagttaact    540
ttgtacttac ctatatcaaa ctaattcaca aataaagta ataataacaa agaattttta     600
gtagatccac aatatacaca cacactatga gaatcataa tagagaattt taatgatttt     660
gtctaactca tagcaacaag tcgctttggc cgagtggtta aggcgtgtgc ctgctaagta    720
catgggctct gcccgcgaga gttcgaatct ctcaggcgac gtttcttttg ttttcggcca    780
taaaggaaaa agcccaatta acacgtctcg cttataagcc cataaagcaa acaatgggct    840
gtctctgtct cactcacaca cgcgttttcc tacttttga ctattttat aaccggcggg      900 tctgacttaa ttagggtttt ctttaataat cagacactct ctcactcgtt tcgtcaacat    960
tgaacacaga caaaaccgcg t                                              981

<210> SEQ ID NO 82
<211> LENGTH: 982
<212> TYPE: DNA
<213> ORGANISM: Arabidopsis thaliana
<220> FEATURE:
<221> NAME/KEY: misc_feature
<223> OTHER INFORMATION: Ceres Promoter construct YP0080 as found in
      Promoter Report #106
<220> FEATURE:
<221> NAME/KEY: misc_feature
<223> OTHER INFORMATION: T1 Mature Plant Expression: GFP expression
      observed in the vasculature of the inflorescence meristem, the
      Petal and Silique of the flower, the Medial vasculature in the
      silique, the Vascular bundle of the leaf and stem
<220> FEATURE:
<221> NAME/KEY: misc_feature
<223> OTHER INFORMATION: T2 Seedling Expression: GFP expression observed
      in the Rosette leaf, the Vascular of the hypocotyly, leaf and
      root, the Pericycle of the root and lateral root

<400> SEQUENCE: 82
aagcggcaat ttagtaagaa gtattcaatg tatcatttac caaaagtata tggttttggg    60
aagagttgtt agggatgtat tctttctaaa cagatgatat gacgatgttc ttgaaaacta    120
atgttaaaga cgggatctct cgcatcttca ctcgggagat atattaaacc gttgattgta    180
gttagccatg tacttagctt agtgcacaaa taatctgctg caagaaatct ttttctatta    240
taatatctct catttaaaca ttagaacata ttgtttaact tgttcttcta gaaataaaac    300
tgctaatttc ttatggtaaa ctattttcct ttagattgca caatcgaact cgaaaatcta    360
gtggagacta tgtgactatg tttatatata tgaaacctaa atcaaattat cccaataatt    420
gggagacaca aagaaaaaa agaaaacagg aaatcaaatc aaagataaa gagaaggtaa      480 aacaaaaggc aagaagcact aatgtttaat atttatagtt ttctccatta agaaaaagc     540 gatgatgtgt gtgttctcat cttttgtgaa agtatatata ttgcttttgc tcttctcaaa    600
agcaaaagac tcatccaaca acaacaacaa aaaaaaccct aaagctcaat ccaaaagacg    660
aagaatgcat tggatactac aacttctttt tcactttct ttcgaattta caattatgat     720
tttcacaata cagtgtattc aaaaataaat aaaaaaacga ggcatgaaaa taatgattat    780
cctcttcact tattaagcca ctcactataa gcagagcaac tccagaacat agtgagcccc    840
```

```
caaaacatta aagcatgatg atgtctaatg atgatgatct tcttcgttcc atttctctaa      900
atttttggga tttctgcgaa gacccttctt ctctttctct tctctgaact tcaagattcg      960
tgtcggacaa attttttgttt tt                                              982
```

<210> SEQ ID NO 83
<211> LENGTH: 987
<212> TYPE: DNA
<213> ORGANISM: Arabidopsis thaliana
<220> FEATURE:
<221> NAME/KEY: misc_feature
<223> OTHER INFORMATION: Ceres Promoter construct YP0122 as found in
      Promoter Report #107
<220> FEATURE:
<221> NAME/KEY: misc_feature
<223> OTHER INFORMATION: T2 Seedling Expression: GFP expression observed
      in the Epidermis of the root transition zone, the root and the
      cotyledon, the Vasculature of the cotyledon

<400> SEQUENCE: 83

```
agtttaatta tttgttatct atccaatcaa tttttttttc taaactgttt ggaccaatgt       60
acgtacgtac catccttttt gattttttt gtaaactaaa ttttcggatt agcaggttct       120
taataattga acgaagaaaa taagaatag aggtagacac ctgtagtatt ttcttggtca       180
gaccaataat ttataattca acgtcaaaga agaagaaaaa tataaaccat tatttcatta      240
tgacttacgt ataccaaaat acacaaatta aatgtataat tgtgaggcat tttatatgcg      300 ggaaaaata aaataaaaag aatattaata tttcttttga aaattgtaaa gcattttgac       360
ccacttgtga tatatatata tagatatata tagagagaga gattaaaaca ttgatggcta      420
gctatagagt ctatggcagg gtcatgatca cctatcttct gatctctgaa gagataccaa      480
tctgattttt tctcttccta ggtttaattt tattttacca ttttataatt ctttattttt      540
gcctgtagta caatttacag acccatacta aagaaaaat taaatttgt caaagtacaa       600 aacaaagaga gaggtgaagc cacacaatct cttttcttct ctctctctct gttatatctc      660
ttctgtttaa ttctttatt cttcttcgtc tatcttctcc tataatctct tctctctccc      720
tcttcaccta aagaataaga agaaaaataa ttcacatctt tatgcaaact actttcttgt      780
agggttttag gagctatctc tattgtcttg gttctgatac aaagttttgt aattttcatg      840
gtatgagaar atttgccttt ctattttgtt tattggttct ttttaacttt tcttggaga      900 tgggttcttg tagatcttaa tgaaacttct gttttgtcc caaaagagt tttctttttt      960 cttctcttct ttttggtttt tcaattc                                          987
```

<210> SEQ ID NO 84
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0226 as found in
      Promoter Report #108
<220> FEATURE:
<221> NAME/KEY: misc_feature
<223> OTHER INFORMATION: T1 Mature Plant Expression: GFP expression
      observed in the Vasculature of the flower and the Silique (Si)
<220> FEATURE:
<221> NAME/KEY: misc_feature
<223> OTHER INFORMATION: T2 Seedling Expression: GFP expression observed
      in the Vasculature of the hypocotyl and root

<400> SEQUENCE: 84

```
ctccttgata atgattttga tcaaaagtgt aatttccaca aaccaattgc gcctgcaaaa       60
```

```
gttttcaaag gatcatcaaa cataatgatg aatatctcat caccacgatt ttataataat      120
gcatcttttc ccaccatttt ttttccctca ctttctttta taatcttgtt cgacaacaat      180
catggtctaa ggaaaaagtt gaaaatatat attatcttag ttattagaaa agaaagataa      240
tcaaatggtc gatatgcaaa tggcatatga ccataaacga gtttgctagt ataaagaatg      300
atggccaacc tgttaaagag agactaaaat taggtctaaa atctaggagc aatgtaacca      360
atacatagta tatgaaatat aaaagttaat ttagattttt tgattagccc aaattaaaga      420
aaaatggtat ttaaaacaga gactcttcat cctaaaggct aaagcaatac aattttttggt     480 taagaaaaga aaaaaccac aagcggaaaa gaaacaaaa aaaactatat tatgatgcaa        540
cagcaacaca aagcaacacc ttgcacacac acatacaact gtaaacaagt ttcttgggac      600
tctctatttt ctcttgctgc ttgaaccaaa cacaacaacg atatcccaac gagagcacaa      660
caggtttgat tatgtcggaa gacaagtttt gagagaaaac aaacaatatt ttataacaaa      720
ggagaagact tttggttagg aaaaattggt atggccatta caagacatat gggtcccaat      780
tctcatcact ctctccacca ccaaaatcct cctctctctc tctctctttt actctgtttt      840
catcatctct ttctctcgtc tctctcaaac cctaaataca ctctttctct tcttgttgtc      900
tccattctct ctgtgtcatc aagcttcttt tttgtgtggg ttatttgaaa gacactttct      960
ctgctggtat cattggagtc tagggttttg ttattgaca                             999
```

<210> SEQ ID NO 85
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter construct YP0244 as found in
      Promoter Report #110
<220> FEATURE:
<221> NAME/KEY: misc_feature
<223> OTHER INFORMATION: T1 Mature Plant Expression: GFP expression
      observed in the pollen

<400> SEQUENCE: 85

```
ttgatttgat gtatagttac tatttaaagt cttatttgtg aaattttaca aatgttggaa       60
aaaagcattt tatggtgcta tatttgtcag tttcccttga ttatatatcc ttttgaaaag     120
taatgttttt tttatgtgtg tgtattcatg aaccttggaa aaactacaaa tcagatcatg     180
gtctgtttta ggtgaaaaat ttagaacaca gttacgcaag aaagatatcg gtaaattttt     240 gtttcttga atcgaaatta atcaaaaagt attttccatt atataacaac aactaatctc      300 tgttttttt tttttttttt aacaactaat ctcttatcaa aatgacacta cagaatcacg      360
attgtaaatc ttcaaaaggg cagtctgaaa aaatattcat gaggatgaga ttttattcat    420
tcatggttgt aagtaatcat tatgtaaagt ttaggataag gacgttcaaa atcatataaa    480
aaaactctac gaataaagtt tatagtctat catattgatt catatttcat agaaagttac    540
tggaaaacat tacacaagta ttctcgattt ttacgagttt gtttagtagt cgcaaaattt    600
tattttactt ttgagtatac gaacccataa gctgattttc tttccaagtt ccaataatga    660
tatcatagtg tactcttcat gaatgtttca agcatataat tataacgttc ataagtaaca    720
ttctactgca tgtttgttat tataaattaa ctaataatcg aacgtatgag ttttggttga    780
gattgttgtg ctcacgaaat gaaggactcg gtcaattcta aagcttaaaa taagaagctc    840
agatcttaaa actcgctttc gtcttcgtcc tccatttaag tttgcgattc ttttgctctt    900
ctttctctct cacatttttg tcccaaaaca ataaaaagaa acaataatag aaagtgttac    960
```

```
agaaaaagaa agaaaactat cattgaagtt gggaaggaga aa                      1002

<210> SEQ ID NO 86
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter construct YP0286 as found in
      Promoter Report #111
<220> FEATURE:
<221> NAME/KEY: misc_feature
<223> OTHER INFORMATION: T1 Mature Plant Expression: GFP expression
      observed in the Pedicel of the inflorescence meristem and the
      flower, the stem
<220> FEATURE:
<221> NAME/KEY: misc_feature
<223> OTHER INFORMATION: T2 Seedling Expression: GFP expression observed
      in the Epidermis of the Hypocotyl, Rosette leaf, Cotyledon, root,
      the Mesophyll and Vasculature of the cotyledon

<400> SEQUENCE: 86
gaaaacaatc ataggttacg ctattatcat cgaaaggtat gtgatgcata ttcccattga    60
accagatttc catatatttt atttgtaaag tgataatgaa tcacaagatg attcaatatt   120
aaaaatgggt aactcactt gacgtgtagt acgtggaaga atagttagct atcacgcata    180
catatatcta tgaataagtg tgtatgacat aagaaactaa aatatttacc taaagtccag   240
ttactcatac tgatttcatg catatatgta ttatttattt atttttaata aagaagcgat   300
tggtgttttc atagaaatca tgatagattg ataggtattt cagttccaca aatctagatc   360
tgtgtgctat acatgcatgt attaattttt tccccttaaa tcatttcagt tgataatatt   420
gctctttgtt ccaactttag aaaaggtatg aaccaacctg acgattaaca agtaaacatt   480
aattaatctt tatatgagat aaaaccgagg atatatatga ttgtgttgct gtctattgat   540
gatgtgtcga tattatgctt gttgtaccaa tgctcgagcc gagcgtgatc gatgccttga   600
caaactatat atgtttcccg aattaattaa gttttgtatc ttaattagaa taacatttt    660 atacaatgta atttctcaag cagacaagat atgtatccta tattaattac tatatatgaa   720
ttgccgggca cctaccagga tgtttcaaat acgagagccc attagtttcc acgtaaatca   780
caatgacgcg acaaaatcta gaatcgtgtc aaaactctat caatacaata atatatattt   840
caagggcaat ttcgacttct cctcaactca atgattcaac gccatgaatc tctatataaa   900
ggctacaaca ccacaaagga tcatcagtca tcacaaccac attaactctt caccactatc   960
tctcaatctc tcgtttcatt tcttgacgcg tgaaaa                             996

<210> SEQ ID NO 87
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter construct YP0289 as found in
      Promoter Report #112
<220> FEATURE:
<221> NAME/KEY: misc_feature
<223> OTHER INFORMATION: T1 Mature Plant Expression: GFP expression
      observed in the Endothelium, Stomium region, Pollen of the
      developing, mature and dehiscing anther
<220> FEATURE:
<221> NAME/KEY: misc_feature
<223> OTHER INFORMATION: T2 Seedling Expression: GFP expression observed
      in the Epidermis of the Cotyledon, cotyledon petiole and root,
      the Guard Cells of the coteledon, the Hypocotyl-root
      transition zone, the Root hair, the Trichomes of the Rosette leaf
```

-continued

<400> SEQUENCE: 87

```
atggactttt cttctattat atggtcaaac aattactgct caatgtattt gcgtatagag      60
catgtccaat accatgcctc atgatgtgag attgcgaggc ggagtcagag aacgagttaa     120
agtgacgacg ttttttttgtt tttttttgggc atagtgtaaa gtgatattaa aatttcatgg    180
ttggcaggtg actgaaaata aaaatgtgta taggatgtgt ttatatgcta gacggaaaaa     240
tagttactca actaatacag atctttataa agagtatata agtctatggt taatcatgaa     300
tggcaatata taagagtaga tgagatttat gtttatattg aaacaaggga aagatatgtg     360
taattgaaac aatggcaaaa tatatagtca aatcaaactg gtttctgata atatatgtgt    420
tgaatcaatg tatatcttgg tattcaaaac caaaacaact acaaccaatt tctttaaaaa    480
accagttgat ctaataacta cattttaata ctagtagcta ttagctgtat ttcataatca     540
atttcttgca ttaaaatttg aagtgggttt tgcatttaaa cttactcggt ttgtattaat     600
agactttcaa agattaaaag aaaactactg cattcagaga ataaagctat cttactaaac    660
actacttttta aagtttcttt tttcacttat taatcttctt atacaaatgg atctgtctct    720
ctgcatggca aaatacttac actaatttta ttttctttgt ttgataacaa atttatcggc    780
taagcatcac ttaaatttaa tacacgttat gaagactaaa accacgtcac actataagaa    840
ccttacaggc tgtcaaacac ccttccctac ccactcacat ctctccacgt ggcaatcttt    900
gatattgaca ccttagccac tacagctgtc acactcctct ctcggtttca aaacaacatc    960
tctggtataa atacctctgt atatctttat aaacccca                              998
```

<210> SEQ ID NO 88
<211> LENGTH: 984
<212> TYPE: DNA
<213> ORGANISM: Arabidopsis thaliana
<220> FEATURE:
<221> NAME/KEY: misc_feature
<223> OTHER INFORMATION: Ceres Promoter construct YP0015 as found in
      Promoter Report #116
<220> FEATURE:
<221> NAME/KEY: misc_feature
<223> OTHER INFORMATION: T1 Mature Plant Expression: GFP expression
      observed in the Abscission zone, Cortex, Epidermis and Guard cells
      of the flower, the Guard cells of the pedicle, and pre-fertilized
      silique the Abscission zone and Carpel of the mature silique
<220> FEATURE:
<221> NAME/KEY: misc_feature
<223> OTHER INFORMATION: T1 Mature Plant Expression: GFP expression
      observed in the Cortex and Epidermis of the carple, the Mesophyll,
      Vasculature and Epidermis of the leaf
<220> FEATURE:
<221> NAME/KEY: misc_feature
<223> OTHER INFORMATION: T2 Seedling Expression: GFP expression observed
      in the Root hair and Root transition of the Hypocotyl

<400> SEQUENCE: 88

```
ttgagcctta ttgttgttat tgactttttag ccaatagaaa gagatggaaa ttcaataatt     60
atccacaaaa ttccaaatca ttggtgtaca aaaagatcta aggctgttat atttccaaaa    120
aagaaagaaa agaaatgcaa caaatatgga ttaaactgtg gtttgtaaat tgagctttgc    180
atgaaaactt tatcactatg atttcactac tccatattta ttgactaaag tggcactaat    240
gaatttctta atcatgaaat cttgtatcaa aaagtactaa aataaacatg acattggcaa    300
ttaggaaaat tctaaattag aaattagtaa aaatgaaagg tgaaagggaa agatgatgat    360
atgaattggt tggtgaccag gagaaatgta tcccgatttt tgcagacact ttcagtgtcc    420
ccattcatat aattatggcc cacctcgtta agatttttca ttcaccacca taacaagatc    480
```

-continued

```
taagcttaga tttcatgtaa ttaaacatat aatatacttg ccaatactat ctaataaagt    540
atacttaagc aaaaattatt actctagtgt aaggcgatga aatataagtt tagttgaaaa    600
tttatgtcga tataacaaag tataatgaat taagaccttg gttttcgatt aacaaactaa    660
ttaaacacta gttttgccta ataaaaccgg gaatcgtatt caaaaccgaa cgacaaaaca    720
agggacaagt tgagagacaa aaccaaatca gcatctttct tccagaaatg tcatgaccac    780
atgacgtcat cttgacccct tcttcattgtg atatctgtgg ataaagcgca cgtgtttaat    840
tcacgaacct tcgtagtaac gaaaaatcca caactttcat atttttttaat tacccactaa    900 actaaaacaa atttggaaaa acatgaaaaa ctttttcttt ttttccaggt tcgtgaacct    960
cgtaccctct atataaacct ctta                                            984
```

<210> SEQ ID NO 89
<211> LENGTH: 970
<212> TYPE: DNA
<213> ORGANISM: Arabidopsis thaliana
<220> FEATURE:
<221> NAME/KEY: misc_feature
<223> OTHER INFORMATION: Ceres Promoter construct YP0230 as found in
      Promoter Report #118
<220> FEATURE:
<221> NAME/KEY: misc_feature
<223> OTHER INFORMATION: T1 Mature Plant Expression: GFP expression
      observed in the Vascular of the Petal in immature and mature
      flowers, the Guard cells of immature flowers, the anther and
      pollen mother cells
<220> FEATURE:
<221> NAME/KEY: misc_feature
<223> OTHER INFORMATION: T1 Mature Plant Expression: GFP expression
      observed in the Pollen during attachment, adhesion and hydration,
      the Seed coat of the ovule, the mature Embryo, the heart stage
      Embryo of the ovule, the Embryo sack of the pre-fertilized ovule
<220> FEATURE:
<221> NAME/KEY: misc_feature
<223> OTHER INFORMATION: T1 Mature Plant Expression: GFP expression
      observed in the Guard cells, Trichomes and Epidermis of the stem,
      the Guard cells of the leaf
<220> FEATURE:
<221> NAME/KEY: misc_feature
<223> OTHER INFORMATION: T2 Seedling Expression: GFP expression observed
      in the Epidermis and Guard cells of the hypocotyl apex, the Guard
      cells, Vascular and Mesophyll of the cotyledon, the Epidermis and
      Cortex of the root transition zone, the Cortex and Nucleus of the
      root

<400> SEQUENCE: 89

```
aatcattaaa tctttgatga gaaatatcca atctactaat gtatatcgat gatttaaatg    60
aaattactta tttgaacaca aaaataaatg aatttactaa taaataaata gcgtagttgc   120
gagcaagtgg ctaaaaaaat tacaaatcta gtttccattc tcagcggcgg ggtgcttgga   180
acgtcaccgt ttttttggaaa acgcaatctt cctcccttcc gggacgtctc accggaattt   240
tctcgctttt gtctactctc ctccatctcc gaggttctcc aagctcagct cctcttccca   300
tcattcatcc gaccgcctta tccggtcaga tcctttacgt atttctattt tcctgatcgt   360 cgattttttga gaaatgtaaa aacagatcgt ataaggcctc gaagttttta atttgaaagt   420
ggtatcgaaa tttttttggtc tttgattagg ttagggcacc gtagctctgg gtattgaatt   480
tgtagggttt tcctctggtt attggtcttt ggagcttggt aatttctgct gaattgattg   540 atccctttttc catcttttga agtaaagtct cgagctttcg tgtctcgatg tagatgaatt   600
ctattttgaa tatgagattt gataagacgt caattgctga taatttggag tctttgtgtc   660
tgaatttgtt catatgaagt tttctgaggg atgtgaattt tattgtctgc taattttgaa   720
```

-continued

```
acgttccttt tggaatttgg tttgtgagga gtcctagatc tttttctgtt aagtttcttg      780
cttgtaagtt ttctggatca cttgattgag tctagaatct agatagatta catgttcggt      840
ttgattcctt tggctgattt tccaaagttt tgttcaaatt tcaggagaac tacaaagagg      900
aaaccaagat ggttttgttt tgttagactc taccccttttt ccgattcaca tggtaaggac     960
attgaggtag                                                             970
```

<210> SEQ ID NO 90
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0120 as found in
      Promoter Report #119
<220> FEATURE:
<221> NAME/KEY: misc_feature
<223> OTHER INFORMATION: T1 Mature Plant Expression: GFP expression
      observed in the ovules of the pre-fertilized and fertilized
      silique, the Outer integument of the fertilized ovule, the
      maturing seed, the Seed coat of the mature seed

<400> SEQUENCE: 90

```
tagtttttga tttaatctac gttttcctta atcataaatg ggtaattatt agttttgca       60 aaatcaaaat ccaaaaattg ttctaaacac tgcaaccatt taaggcctat atcactcaga     120
aaatttctgg tgggagaact aatcgtttgt cctttctaaa tctcacatat tagaatttag     180
aattagtgtg ctacataaga atattagttc agctcggaac aactatttt tggtaaaaca     240 gagaacttaa acaaatgcat tatttttatca acatgcattt tgaattgaat ataaaatttc    300
ataattgtaa agacataaat tacataaaat tttacatgaa aaaatagata tagaaagaaa     360
atgaaactaa ctgatgatat gctctctaaa tttttaatc tcataacaag aattcaaatt      420
aattagttca tattttggt taatataaca tttacctgtc taagttggaa ctttcatttt       480
tttctgtttt gtttagtcag tattcttaat gtgaaacgga aagttgaatt tattcaaact     540
taaattcaat agcattaatt aaaggcgaaa gctattatct ctacatgtgg ttcaaactag     600
acatccaatt taattagctt attgacgttg aaatgttttc caaaactact atagtttggc    660
aatttgaaag atgcatcaga actactcaga caggtaaaag tagaacctct agctgtgtga   720
attgtatgtt agtccataaa gaacatcttg taaacttcat acttaagata tatattacaa     780
tatatacttg aatggtagat aaaaacgatt agtctgattg ctagcatact cacaactatt    840
tggaaatgag taagatattg gcattctaga gttactacta tggagacaaa agtcgaataa   900
aagagacctc acgtgaaaat gttacgagct agtaaaaaaa gcatttacac taacggtaaa    960
aaaagtatct ataaatgttt acacaaggta gtagtcatt                            999
```

<210> SEQ ID NO 91
<211> LENGTH: 989
<212> TYPE: DNA
<213> ORGANISM: Arabidopsis thaliana
<220> FEATURE:
<221> NAME/KEY: misc_feature
<223> OTHER INFORMATION: Ceres Promoter construct YP0261 as found in
      Promoter Report #120
<220> FEATURE:
<221> NAME/KEY: misc_feature
<223> OTHER INFORMATION: T1 Mature Plant Expression: GFP expression
      observed in the Epidermis and Vasculature of the Petal
<220> FEATURE:
<221> NAME/KEY: misc_feature
<223> OTHER INFORMATION: T2 Seedling Expression: GFP expression observed
      in the Epidermis and Guard cells of the rosette leaf primordia

```
<220> FEATURE:
<221> NAME/KEY: misc_feature
<222> LOCATION: (480)..(480)
<223> OTHER INFORMATION: n is a, c, t, g, unknown, or other

<400> SEQUENCE: 91
ttgtaaatta gttttatcgt agaagtacca aatcaagtga ttcaatggtt aaattaaggt      60
attaagttac atttgatatt taaaagtatc cagaccttca ttatagctca taagggttaa     120
aattttgtcg ttcttttgta tattcatggc aagctctaat tcatgactaa gtcacatttt     180
tcaaatatgt ttttagtttt tacttatgtt ggtaattagt ggatttatag ttaagttaaa     240
aagttggcga gttctagctt tgaaactcat ttagaaatat atatatatat atatatattc     300
aattttagta aattgttaat ctattctaat ggtgtaactg taacaaatga gaatgaaaaa     360
aatatactat tgtgaataaa accccacaca acacattact ataataagtt aaacttcttt     420
ttttataggc gcctggaaaa aaagaaaag caacaagagg gstgtgagga cgcatcaccn      480
ggtttcgtag cacacatgtg catttgtctc tttgctttt cggttttttt cttgccaatc      540
aatttatttt gttcctcaga aaaagaaaa tctaaaacca aaatatatat tataacctca      600
tttaataaac aacaaaaatg tttgttgaaa aaaaaaaagt ttttatttat cttgaccta      660 tttctttgaa gaaataaag cttggttatt aagaagtcc aagttagttg ccaccatcag      720
tggcataacg gtaaattaaa gccaacttcc tctaactaaa gttttctata aattcaacca     780
ctcacctccc actctaaaac ccaacaacat aatttcacat atctctcttt ctttctcttg     840
aaggaaagac gaagatctcc aagtcccaag tacgtaacta ctttctccat ctacattcaa     900
ttgtttctcc ttaatttctc tagtacatat ttacttgtgc tataagtaat tgatttata      960 tcacccatgt gcaggttgtt aacacaaga                                       989

<210> SEQ ID NO 92
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter construct YP0263 as found in
      Promoter Report #121
<220> FEATURE:
<221> NAME/KEY: misc_feature
<223> OTHER INFORMATION: T1 Mature Plant Expression: GFP expression
      observed in the Vasculature of the inflorescence meristem and the
      Pedicel and Receptacle, the Medial vasculature of the leaf, the
      stem, the Medial vasculature of the immature and mature silique
<220> FEATURE:
<221> NAME/KEY: misc_feature
<223> OTHER INFORMATION: T1 Mature Plant Expression: GFP expression
      observed in the Vasculature of the Anther, Abscission zone,
      Filament, Carpel, Filament, Funiculus, Ovule, Placenta, Root cap,
      Sepal, Silique
<220> FEATURE:
<221> NAME/KEY: misc_feature
<223> OTHER INFORMATION: T2 Seedling Expression: GFP expression
      observed in the Epidermis of the Rosette leaf of the seeding, the
      Cortex of the root, the vasculature of the seedling and cotyledon,
      the root tip

<400> SEQUENCE: 92
atctagctgt ggattccacc aaaattctgg cagggccatg atctaaaaac tgagactgcg      60
cgtgttgttt tgcagtgatt tgtatttcat atttgcacca tcctacacag tccacttggt     120
atcgtaacca aacataagga gaacctaatt acattattgt tttaatttcg tcaaactggt     180 ttttacccttt tagttacata gttgattctt catttgtttt agtagttatg gagcacaata     240
```

```
atgtgcaaca aagaaagatc atagtggatt aatatgttga gaggtcagaa attcttggtt    300
aacaaaaaaa agttacaagg actgagattt tgggtgggag aaagccatag cttttaaaac    360
atgattgaac ttaaaagtga tgttatggtt tgagggaaa aaggttgatg tcaactaaga    420
tagttgaagt aatgtcttaa actaaagtaa accaccggtc caaccgtggt ccggaagcat    480
ctctggtatg atttatccta aaaatcaaaa tagtagaaac atactttaaa tatatacatt    540
gatcggacga aaattgtaaa ctagtatagt ttcaaaaact agttgaacag gttatgtacc    600
ttaaacattt atttcaaact taaacactaa agaacatata tgaatagaag tttatataaa    660
ttactatata tctaccataa atctcttata attatgatgt cacgatgagg aagtgttgaa    720
acgttaaaat gccaaaatat aagcatgcga cggaattttg gcagaagatt gtagagttgt    780
aatctgtcgc aatcattact cgtgctagca tttttcattt tcccttcatt tgtggataac    840
gcacgatata acattctaca caccaacaag attctataaa aacgcaaagg ttgtctccat    900
agaatatcgt c                                                          911

<210> SEQ ID NO 93
<211> LENGTH: 863
<212> TYPE: DNA
<213> ORGANISM: Arabidopsis thaliana
<220> FEATURE:
<221> NAME/KEY: misc_feature
<223> OTHER INFORMATION: Ceres Promoter construct YP0003 as found in
      Promoter Report #123
<220> FEATURE:
<221> NAME/KEY: misc_feature
<223> OTHER INFORMATION: T1 Mature Plant Expression: GFP expression
      observed in the Guard cells of the flower, pedicel and silique,
      the Vasculature of the mature embryo and the cotyledons
<220> FEATURE:
<221> NAME/KEY: misc_feature
<223> OTHER INFORMATION: T2 Seedling Expression: GFP expression observed
      in the Root hair of the Hypocotyl and the root transition zone,
      the Epidermis of the upper and lower Root, the Vascular of the
      lower root

<400> SEQUENCE: 93
tggatctgct agatatatga gaacgaaaga accagaagct attagaggcg ggaggagata     60
tgtggggatg atttcagtgc aattccacga cgcaccattt ccactttcgt aacacctaaa    120
cgaccgcttc ggccgtataa aatcgcaaat gtttggtctc agtgtatttt tccaatttcc    180
aaatacatca attcaaatta tataatatct agtggcaatt ataagtatat catatatttt    240
caaaattaat taaaaagatt actaaattat gtttgactac aactattata atagttaaaa    300
acataaacaa aaacaaagaa actattttaa taaaaaaatc aagtaaacat taaaacataa    360
gcaaaaaata atgttaaaga aattattaat tattaattta ctaataatta atacctctat    420
aaattaattg ttagaggttt aacgtaattt ataaggaaaa ctaaagaaga ctttaaccca    480
taaagaaaaa aacaaagact gaattgaagg cccatattta gaagaagaga aagaagaccc    540
aaatatgata taaaatccag cccatttata tatttttatt ttgtttctgg aaggaaaata    600
agaaaatggc aaaaacgaaa taatctgaaa agtaaggtc ttttaccaaa aaggatatt     660 tttttataaa cagagcataa agttttcact tttcttctgc tcctttctcg tctctgtctt    720
cttcgtcctc attcgtttta aagcatcaaa atttcatcaa cccaaaatag attaaaaaaa    780
tctgtagctt tcgcatgtaa atctctcttt gaaggttcct aactcgttaa tcgtaactca    840
cagtgactcg ttcgagtcaa agt                                            863

<210> SEQ ID NO 94
```

```
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0356 as found in
      Promoter Report #125
<220> FEATURE:
<221> NAME/KEY: misc_feature
<223> OTHER INFORMATION: T1 Mature Plant Expression: GFP expression
      observed in the pedicel of the inflorescence meristem and the
      flower, the item below the inflorescence meristem, the Stigma
      of the flower, the Petal of the flower, the Style and Carpel of
      the silique
<220> FEATURE:
<221> NAME/KEY: misc_feature
<223> OTHER INFORMATION: T1 Mature Plant Expression: GFP expression
      observed in the Outer integument of the ovule, the Epidermis of
      the stem
<220> FEATURE:
<221> NAME/KEY: misc_feature
<223> OTHER INFORMATION: T2 Seedling Expression: GFP expression observed
      in the Epidermis of the hypocotyl, the root transition zone, the
      cotyledon and the rosette, the Trichomes of the rosette leave
      and trichome base cells

<400> SEQUENCE: 94
ttagttcatt gaaacgtcaa cttttactt gcaaccactt tgtaggacca ttaactgcaa      60
aataagaatt ctctaagctt cacaagggt tcgtttggtg ctataaaac attgttttaa     120 gaactggttt actggttcta taaatctata aatccaaata tgaagtatgg caataataat     180
aacatgttag cacaaaaaat actcattaaa ttcctaccca aaaaaaatct ttatatgaaa     240
ctaaaactta tatacacaat aatagtgata caaagtaggt cttgatattc aactattcgg     300
gattttctgg tttcgagtaa ttcgtataaa aggtttaaga tctattatgt tcactgaaat     360
cttaactttg ttttgtttcc agttttaact agtagaaatt gaaattttta aaaattgtta     420
cttacaataa aatttgaatc aatatcctta atcaaaggat cttaagacta gcacaattaa     480
aacatataac gtagaatatc tgaaataact cgaaaatatc tgaactaagt tagtagttt     540 aaaatataat cccggtttgg accgggcagt atgtacttca atacttgtgg gttttgacga     600
ttttggatcg gattgggcgg gccagccaga ttgatctatt acaaatttca cctgtcaacg     660
ctaactccga acttaatcaa agattttgag ctaaggaaaa ctaatcagtg atcacccaaa     720
gaaaacattc gtgaataatt gtttgctttc catggcagca aaacaaatag gacccaaata     780
ggaatgtcaa aaaaagaaa gacacgaaac gaagtagtat aacgtaacac acaaaaataa     840
actagagata ttaaaaacac atgtccacac atggatacaa gagcatttaa ggagcagaag     900
gcacgtagtg gttagaaggt atgtgatata attaatcggc ccaaatagat tggtaagtag     960
tagccgtcta tatcatccat actcatcata acttcaacct                          1000

<210> SEQ ID NO 95
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0374 as found in
      Promoter Report #126
<220> FEATURE:
<221> NAME/KEY: misc_feature
<223> OTHER INFORMATION: T1 Mature Plant Expression: GFP expression
      observed in the Chalaza Funiculus and Outer integument of the
      ovule primordial, the Chalaza in the pre-fertilized ovule, the
      Chalaza and Micropyle of the fertilized ovule and developing seed,
      the Chalaza of the mature seed
<220> FEATURE:
```

-continued

```
<221> NAME/KEY: misc_feature
<223> OTHER INFORMATION: T2 Seedling Expression: GFP expression observed
      in the Epidermis of the seedling root, the Vascular of the
      Hypocotyl and root transition zone, the Vascular and Pericycle of
      the root

<400> SEQUENCE: 95
aagacacccg taaatgttgt catgtagaag aaactagaaa cgttaaacgc atcaaatcaa     60
gaaattaaat tgaaggtaat ttttaacgcc gcctttcaaa tattcttcct aggagaggct    120
acaagacgcg tatttctttc gaattctcca aaccattacc attttgatat ataataccga    180
catgccgttg ataaagtttg tatgcaaatc gttcattggg tatgagcaaa tgccatccat    240
tggttcttgt aattaaatgg tccaaaaata gtttgttccc actactagtt actaatttgt    300
atcactctgc aaaataatca tgatataaac gtatgtgcta tttctaatta aaactcaaaa    360
gtaatcaatg tacaatgcag agatgaccat aaaagaacat taaaacacta cttccactaa    420
atctatgggg tgccttggca aggcaattga ataaggagaa tgcatcaaga tgatatagaa    480
aatgctattc agtttataac attaatgttt tggcggaaaa ttttctatat attagacctt    540
tctgtaaaaa aaaaaaaatg atgtagaaaa tgctattatg tttcaaaaat ttcgcactag    600
tataatacgg aacattgtag tttacactgc tcattaccat gaaaaccaag gcagtatata    660
ccaacattaa taaactaaat cgcgatttct agcaccccca ttaattaatt ttactattat    720
acattctctt tgcttctcga ataataaac ttctctatat cattctacat aataaataag     780
aaagaaatcg acaagatcta aatttagatc tattcagctt tttcgcctga gaagccaaaa    840
ttgtgaatag aagaaagcag tcgtcatctt cccacgtttg gacgaaataa aacataacaa    900
taataaaata ataaatcaaa tatataaatc cctaatttgt ctttattact ccacaatttt    960
ctatgtgtat atatataccc acctctctct tgtgtatttg                         1000

<210> SEQ ID NO 96
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter construct YP0377 as found in
      Promoter Report #127
<220> FEATURE:
<221> NAME/KEY: misc_feature
<223> OTHER INFORMATION: T1 Mature Plant Expression: GFP expression
      observed in the Petal, and Sepal of the flower, the flower bud
<220> FEATURE:
<221> NAME/KEY: misc_feature
<223> OTHER INFORMATION: T2 Seedling Expression: GFP expression observed
      in the Epidermis, Vasculature and Guard cells of the seedling
      apex, the Vasculature of the Cotyledon petiole, Hypocotyl and
      root, the Epidermis of the root and Cotyledon petiole

<400> SEQUENCE: 96
tataaaccat tcctataaca ccatatttaa acataacaat gaattgcttg gatttcaaac     60
tttattaaat ttggatttta aatttaatt tgattgaatt ataccccctt aattggataa     120
attcaaatat gtcaacttt tttttgtaag atttttttat ggaaaaaaaa attgattatt     180
cactaaaaag atgacaggtt acttataatt taatatatgt aaaccctaaa agaagaaaa     240 tagtttctgt tttcacttta ggtcttatta tctaaacttc tttaagaaaa tcgcaataaa    300
ttggtttgag ttctaacttt aaacacatta atatttgtgt gctatttaaa aaataattta    360
caaaaaaaaa aacaaattga cagaaaatat caggttttgt aataagatat ttcctgataa    420
atatttaggg aatataacat atcaaaagat tcaaattctg aaaatcaaga atggtagaca    480
```

-continued

```
tgtgaaagtt gtcatcaata tggtccactt ttctttgctc tataacccaa aattgaccct      540
gacagtcaac ttgtacacgc ggccaaacct ttttataatc atgctattta tttccttcat      600
ttttattcta tttgctatct aactgatttt tcattaacat gataccagaa atgaatttag      660
atggattaat tcttttccat ccacgacatc tggaaacact tatctcctaa ttaaccttac      720
ttttttttta gtttgtgtgc tccttcataa aatctatatt gtttaaaaca aaggtcaata      780
aatataaata tggataagta taataaatct ttattggata tttcttttt taaaaaagaa       840 ataaatcttt tttggatatt ttcgtggcag catcataatg agagactacg tcgaaaccgc      900
tggcaaccac ttttgccgcg tttaatttct ttctgaggct tatataaata gatcaaggg      960 gaaagtgaga tataatacag acaaaacaag agaaaaga                             998
```

<210> SEQ ID NO 97
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0380 as found in
      Promoter Report #128
<220> FEATURE:
<221> NAME/KEY: misc_feature
<223> OTHER INFORMATION: T1 Mature Plant Expression: GFP expression
      observed in the Flower of the inflorescence meristem, the Silique,
      Stamen, Petal, and Sepal of the immature flower, the Silique,
      Sepal and Receptacle of the mature flower, the Anther, the Valve
      margin of the silique
<220> FEATURE:
<221> NAME/KEY: misc_feature
<223> OTHER INFORMATION: T1 Mature Plant Expression: GFP expression
      observed in the Funiculus of the placenta and mature ovule, the
      ovule primordial and developing ovule, the Trichome, Epidermis,
      Nucleus, the Epidermis, Mesophylland Guard cells of the abaxial
      leaf
<220> FEATURE:
<221> NAME/KEY: misc_feature
<223> OTHER INFORMATION: T1 Mature Plant Expression: GFP expression
      observed in the the Mesophyll of the adaxial leaf, the Cortex,
      Epidermis and Guard cells of the stem
<220> FEATURE:
<221> NAME/KEY: misc_feature
<223> OTHER INFORMATION: T2 Seedling Expression: GFP expression observed
      in the seedling seedling apex, hypocotyl, cotyledon and root, the
      Rosette leaf, the Root, the Mesophyll, Epidermis and Guard cells
      of the leaf

<400> SEQUENCE: 97

```
acaagtacca ttcactttt tactttcaa tgtatacaat catcatgtga taaaaaaaa         60 aatgtaacca atcaacacac tgagatacgg ccaaaaatg gtaatacata aatgtttgta      120
ggttttgtaa tttaaatact ttagttaagt tatgatttta ttattttgc ttatcactta     180 tacgaaatca tcaatctatt ggtatctctt aatcccgctt tttaatttcc accgcacacg     240
caaatcagca aatggttcca gccacgtgca tgtgaccaca tattgtggtc acagtactcg     300
tccttttttt ttcttttgta atcaataaat ttcaatccta aaacttcaca cattgagcac     360
gtcggcaacg ttagctccta aatcataacg agcaaaaaag ttcaaattag ggtatatgat     420
caattgatca tcactacatg tctacataat taatatgtat tcaaccggtc ggtttgttga    480
tactcatagt taagtatata tgtgctaatt agaattagga tgaatcagtt cttgcaaaca     540
actacggttt catataatat gggagtgtta tgtacaaaat gaaagaggat ggatcattct     600
gagatgttat gggctcccag tcaatcatgt tttgctcgca tatgctatct tttgagtctc     660 ttcctaaaact catagaataa gcacgttggt ttttccacc gtcctcctcg tgaacaaaag     720
```

```
tacaattaca ttttagcaaa ttgaaaataa ccacgtggat ggaccatatt atatgtgatc      780
atattgcttg tcgtcttcgt tttcttttaa atgtttacac cactacttcc tgacacgtgt      840
ccctattcac atcatccttg ttatatcgtt ttacttataa aggatcacga acaccaaaac      900
atcaatgtgt acgtcttttg cataagaaga aacagagagc attatcaatt attaacaatt      960
acacaagaca gcgagattgt aaaagagtaa gagagagag                             999
```

```
<210> SEQ ID NO 98
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0381 as found in
      Promoter Report #129
<220> FEATURE:
<221> NAME/KEY: misc_feature
<223> OTHER INFORMATION: T1 Mature Plant Expression: GFP expression
      observed in the Pedicel of the inflorescence meristem,
      the lateral and medial Nectary in the flower,
      the modified stomata opening in the lateral nectary
<220> FEATURE:
<221> NAME/KEY: misc_feature
<223> OTHER INFORMATION: T2 Seedling Expression: GFP expression observed
      in the Vasculature of the Hypocotyl and root

<400> SEQUENCE: 98
cacggtcaaa gtattgctaa catggtcatt acattgaaaa agaaaattaa ttgtctttac      60
tcatgtttat tctatacaaa taaaaatatt aaccaaccat cgcactaaca aaatagaaat     120
cttattctaa tcacttaatt gttgacaatt aaatcattga aaaatacact taaatgtcaa     180
atattcgttt tgcatacttt tcaatttaaa tacatttaaa gttcgacaag ttgcgtttac     240
tatcatagaa aactaaatct cctaccaaag cgaaatgaaa ctactaaagc gacaggcagg     300
ttacataacc taacaaatct ccacgtgtca attaccaaga gaaaaaaga gaagataagc      360 ggaacacgtg gtagcacaaa aaagataatg tgatttaaat taaaaaacaa aaacaaagac     420
acgtgacgac ctgacgctgc aacatcccac cttacaacgt aataaccact gaacataaga     480
cacgtgtacg atcttgtctt tgttttctcg atgaaaacca cgtgggtgct caaagtcctt     540
gggtcagagt cttccatgat tccacgtgtc gttaatgcac caaacaaggg tactttcggt     600
attttggctt ccgcaaatta gacaaaacag ctttttgttt gattgatttt tctcttctct     660
ttttccatct aaattctctt tgggctctta atttctttt gagtgttcgt tcgagatttg      720
tcggagattt tttcggtaaa tgttgaaatt ttgtgggatt ttttttatt tctttattaa      780 actttttttt attgaattta taaaaaggga aggtcgtcat taatcgaaga aatggaatct     840
tccaaaattt gatatttgtc tgttttcttg ggatttgaat tgctctttat catcaagaat     900
ctgttaaaat ttctaatcta aaatctaagt tgagaaaaag agagatctct aatttaaccg     960
gaattaatat tctccgaccg aagttattat gttgcaggct                          1000
```

```
<210> SEQ ID NO 99
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0382 as found in
      Promoter Report #130
<220> FEATURE:
<221> NAME/KEY: misc_feature
<223> OTHER INFORMATION: T1 Mature Plant Expression: GFP expression
``` observed in the Nectary of the flower, the Vasculature of the
Sepal
<220> FEATURE:
<221> NAME/KEY: misc_feature
<223> OTHER INFORMATION: T2 Seedling Expression: GFP expression observed
in the Vasculature of the cotyledon and Rosette leaf,
the Epidermis and Root hair,
of the root, the seedling root and root cap

<400> SEQUENCE: 99

```
gcaaacaata atttatcgta agagtttttt taaaattcgt tggaacttgg aagggatttt      60
aaatattatt ttgttttcct tcatttttat aggttaataa ttgtcaagaa tacaactcga     120
tggaccaaaa taaaataata aaattcgtcg aatttggtaa agcaaaacgg tcgaggatag     180
ctaatattta tgcgaaaccc gttgtcaaag cagatgttca gcgtcacgca catgccgcaa     240
aaagaatata catcaacctc ttttgaactt cacgccgttt tttaggccca caataatgct     300
acgtcgtctt ctgggttcac cctcgttttt tttttaaact tctaaccgat aaaataaatg     360
gtccactatt tcttttcttc tctgtgtatt gtcgtcagag atggtttaaa agttgaaccg     420
aactataacg attctcttaa aatctgaaaa ccaaactgac cgattttctt aactgaaaaa     480
aaaaaaaaaa aaactgaatt taggccaact tgttgtaata tcacaaagaa aattctacaa     540
tttaattcat ttaaaaataa agaaaaattt aggtaacaat ttaactaagt ggtctatcta     600
aatcttgcaa attctttgac tttgaccaaa cacaacttaa gttgacagcc gtctcctctc     660
tgttgtttcc gtgttattac cgaaaatatca gaggaaagtc cactaaaccc caaatattaa     720
aaatagaaac attactttct ttacaaaagg aatctaaatt gatccctttc attcgtttca     780
ctcgtttcat atagttgtat gtatatatgc gtatgcatca aaaagtctct ttatatcctc     840
agagtcaccc aatcttatct ctctctcctt cgtcctcaag aaaagtaatt ctctgtttgt     900
gtagttttct ttaccggtga attttctctt cgttttgtgc ttcaaacgtc acccaaatca     960
ccaagatcga tcaaaatcga aacttaacgt ttcagaaga                             999
```

<210> SEQ ID NO 100
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0388 as found in
Promoter Report #131
<220> FEATURE:
<221> NAME/KEY: misc_feature
<223> OTHER INFORMATION: T1 Mature Plant Expression: GFP expression
observed in the Guard cells and Seed coat of the inflorescence
meristem, the Stamen of the flower, the Seed coat of the
developing seed, the Chalaza and Outer integument of aborted
ovules, Guard cells and Vasculature of the leaf
<220> FEATURE:
<221> NAME/KEY: misc_feature
<223> OTHER INFORMATION: T2 Seedling Expression: GFP expression observed
in the Epidermis of the seedling root

<400> SEQUENCE: 100

```
agaagtattc acgcaccaag gttatatttg tagtgacata ttctacaatt atcacatttt      60
tctcttatgt ttcgtagtcg cagatggtca attttttcta taataatttg tccttgaaca     120
caccaaactt tagaaacgat gatatatacc gtattgtcac gctcacaatg aaacaaacgc     180
gatgaatcgt catcaccagc taaaagccta aaacaccatc ttagttttca ctcagataaa     240
aagattattc gttccaacc tttctattga attgattagc agtgatgacg taattagtga     300
tagtttatag taaaacaaat ggaagtggta ataaatttac acaacaaaat atggtaagaa     360
```

```
tctataaaat aagaggttaa gagatctcat gttatattaa atgattgaaa gaaaaacaaa       420
ctattggttg atttccatat gtaatagtaa gttgtgatga aagtgatgac gtaattagtt       480
gtatttatag taaaacaaat taaaatggta aggtaaattt ccacaacaaa acttggtaaa       540
aatcttaaaa aaaaaaaaag aggtttagag atcgcatgcg tgtcatcaaa ggttctttt        600 cactttaggt ctgagtagtg ttagactttg attggtgcac gtaagtgttt cgtatcgcga       660
tttaggagaa gtacgtttta cacgtggaca caatcaacgg tcaagatttc gtcgtccaga      720
tagaggagcg atacgtcacg ccattcaaca atctcctctt cttcattcct tcattttgat      780
tttgagtttt gatctgcccg ttcaaaagtc tcggtcatct gcccgtaaat ataaagatga      840
ttatatttat ttatatcttc tggtgaaaga agctaatata aagcttccat ggctaatctt      900
gtttaagctt ctcttcttct tctctctcct gtgtctcgtt cactagtttt ttttcggggg      960
agagtgatgg agtgtgtttg ttgaatagtt ttgacgatca                           1000

<210> SEQ ID NO 101
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0396 as found in
      Promoter Report #133
<220> FEATURE:
<221> NAME/KEY: misc_feature
<223> OTHER INFORMATION: T1 Mature Plant Expression: GFP expression
      observed in the Style of the Silique, the Anther, Petal and Sepal
      of the flower, the anther locules, the Outer integument of the
      normal and aborted ovule, the Hydathode and Vasculature of the
      leaf
<220> FEATURE:
<221> NAME/KEY: misc_feature
<223> OTHER INFORMATION: T2 Seedling Expression: GFP expression observed
      in the Epidermis of the root

<400> SEQUENCE: 101
catagtaaaa gtgaatttaa tcatactaag taaaataaga taaaacatgt tatttgaatt        60
tgaatatcgt gggatgcgta tttcggtatt tgattaaagg tctggaaacc ggagctccta      120
taacccgaat aaaaatgcat aacatgttct tccccaacga ggcgagcggg tcagggcact      180
agggtcattg caggcagctc ataaagtcat gatcatctag gagatcaaat tgtatgtcgg      240
ccttctcaaa attacctcta agaatctcaa acccaatcat agaacctcta aaaagacaaa      300
gtcgtcgctt tagaatgggt tcggttttg gaaccatatt tcacgtcaat ttaatgttta      360
gtataatttc tgaacaacag aattttggat ttatttgcac gtatacaaat atctaattaa     420
taaggacgac tcgtgactat ccttacatta agtttcactg tcgaaataac atagtacaat     480
acttgtcgtt aatttccacg tctcaagtct ataccgtcat ttacggagaa agaacatctc     540 tgttttcat ccaaactact attctcactt tgtctatata tttaaaatta agtaaaaaag      600
actcaatagt ccaataaaat gatgaccaaa tgagaagatg gttttgtgcc agattttagg     660
aaaagtgagt caaggtttca catctcaaat ttgactgcat aatcttcgcc attaacaacg     720
gcattatata tgtcaagcca attttccatg ttgcgtactt ttctattgag gtgaaaatat     780
gggtttgttg attaatcaaa gagtttgcct aactaatata actacgactt tttcagtgac     840
cattccatgt aaactctgct tagtgtttca tttgtcaaca atattgtcgt tactcattaa    900
atcaaggaaa aatatacaat tgtataattt tcttatattt taaaattaat tttgatgtat   960 tacccctta taaataggct atcgctacaa caccaataac                           1000
```

<210> SEQ ID NO 102
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct PT0506 as found in
      Promoter Report #135
<220> FEATURE:
<221> NAME/KEY: misc_feature
<223> OTHER INFORMATION: T1 Mature Plant Expression: GFP expression
      observed in the Filament

<400> SEQUENCE: 102

```
aggacttcca ctactctttc ccacacgctc cagaccactg tttgctttcc tctgattaac      60
caatctcaat taaactacta atttataatt caagataatt agataaccaa tcttaaaatt     120
tggaatcttc ttccctcact tgatattaca aaaaaaaaac tgatttatca tacggttaat     180
tcaagaaaac agcaaaaaaa ttgcactata atgcaaaaca tcaattaatt acattcgatt     240
aaaaaatcat cattgaatct aaatggcct caaatctatt gagcatttgt catgtgccta      300
aaatggttca ggagttttac atctaatcac ataaaaagca aacaataacc aaaaaaattg     360
cattttagca aatcaaatac ttatatatat acgtatgatt aagcgtcatg actttaaaac     420
ctctgtaaaa ttttgattta tttttcgatg cttttatttt ttaaccaata gtaataaagt     480
ccaaatctta aatacgaaaa aatgtttctt tctaagcgac caacaaaatg gtccaaatca     540
cagaaaatgt tccataatcc aggcccatta agctaatcac caagtaatac attacacgtc     600
accaattaat acattacacg tacggccttc tctcttcacg agtaatatgc aaacaaacgt     660
acattagctg taatgtactc actcatgcaa cgtcttaacc tgccacgtat tacgtaatta     720
caccactcct tgttcctaac ctacgcattt cactttagcg catgttagtc aaaaaacaca     780
aacataaact acaaataaaa aaactcaaaa caaaacccaa tgaacgaacg gaccagcccc     840
gtctcgattg atggaacagt gacaacagtc ccgttttctc gggcataacg gaaacggtaa     900
ccgtctctct gtttcatttg caacaacacc attttataa ataaaaacac atttaaataa     960
aaaattatta aaacctcaaa aaatctctgt ttcttgttta                          1000
```

<210> SEQ ID NO 103
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct PT0511 as found in
      Promoter Report #136
<220> FEATURE:
<221> NAME/KEY: misc_feature
<223> OTHER INFORMATION: T1 Mature Plant Expression: GFP expression
      observed in the Anther and Vascular of the anther
<220> FEATURE:
<221> NAME/KEY: misc_feature
<223> OTHER INFORMATION: T2 Seedling Expression: GFP expression observed
      in the root and Vascular of the Pedicle

<400> SEQUENCE: 103

```
tttaattttg attctaaaga gttgtgacgg gtcatcacag attcttcgtt tttttataga      60
tagaaaagga ataacgttaa aagtatacaa attatatgca agagtcattc gaaagaatta     120
aataaagaga tgaactcaaa agtgatttta aattttaatg ataagaatat acatctcaca     180
gaaatctttt atttgacatg taaatccttg ttttcaccta tcttttgtta gtaaacaaga     240
```

```
atatttaatt tgagcctcac ttggaacgtg ataataatat acatcttatc ataattgcat      300
attttgcgga tagttttgc atggggagat taaaggctta ataaagcctt gaatttccga       360
ggggaggaat catgttttat acttgcaaac tatacaacca tctgcatcga taattggtgt     420
taatacatgc aaggattata cactaaaaca aatcatttat ttccttacaa aaagagagtc     480
gactgtgagt cacattctgt gacaaggaaa ggtcaagaac catcgctttt atcatcattc     540
tctttgctaa caacttacaa ccacacaaac gcaagagttc cattctcatg gagaagaaca     600
tattatgcaa ataatgtat gtcgatcgat agagaaaagg atccacaatt attgctccat     660
ctcaaaagct tctttagtac acgatacatg tatcatgtaa atagaaatat gaaagataca     720
atacacgacc cattctcata aagatagcaa catttcatgt tatgtaaaga gtcttcctta     780
ggacacatgc attaaaacta aggattacca acccacttac tcctcactcc aaccaaatat    840
caatcatcta ttttgggtcc ttcactcata agtcaactct catgccttcc tctataaata    900
ccgtacccta cgcatccctt agttctacat cacataaaaa caatcatagc aaaaacatat    960
atcctcaaat taattagatc tcatctatct ctaccctcga                         1000
```

<210> SEQ ID NO 104
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0262 as found in
      Promoter Report #141
<220> FEATURE:
<221> NAME/KEY: misc_feature
<223> OTHER INFORMATION: T1 Mature Plant Expression: GFP expression
      observed in Guard Cells that define the stomate

<400> SEQUENCE: 104

```
tacttcgtaa ggttaatata tgatatagtg ggcctgacaa aaatcatat gggcttgaca       60 aaatctatgt ttatatccag ttcggtccaa aattcgaaaa cataaacaat gtggaaagat     120
gtgttggcta atctgatacc atgtcaaaaa aacatagaag ttcttgtgag gtttcttgtt     180
tattcatgtg gaggcaattg cccttgtata caaggcttgt gaaagaagta aagaagataa     240
gtttaggaag aaggtggccc atgagggccc aatattcata tcattagtga aaagcatagg    300
aatttcaact tgtaatatta aaatcagtga taattgaata acattaatct ttttaagatt    360
tccaaattaa ttcaaatctt cattaagaaa taagatttag gaatactaaa aagctaaata    420
attatctaat tacttaaaat cagtaatgaa aattaatatt atactcccat agtatatttt    480
cttcactatg aatgaagttg agacttcaat tttgacaaat tcggtgttct ggaataacaa    540
aagaagtcaa agaaagaaaa ttagggagat agagtaaatt aaagttgaga caaatcagct    600
tcattttgtt tttcccaaat aataatatac agatagatct ttcggccccg gcgcattctc    660
tagatttgct catcaccacc tcgaaatttc tgctcgaagt tctccaaaac agttcattca    720
tctacattta ccagatcata ttcgtattca gtcgtctcta aattctcact aaatcaatcc    780
ttcctttgga taattccggt gtttgcgagg aatctgttga aatgattggt tagttcagtt    840
aaactctact tctaaaacta aatctgcatt caaatgtagt ctctagttct cgtacttgaa    900
gtagacttga ttcgatttga tttactgatt cgtggctttt gatttcacag gtcaattgga    960
aatctgagaa tccgtgtgac tattattgca gctggatcg                           999
```

<210> SEQ ID NO 105
<211> LENGTH: 999

```
<212> TYPE: DNA
<213> ORGANISM: Arabidopsis thaliana
<220> FEATURE:
<221> NAME/KEY: misc_feature
<223> OTHER INFORMATION: Ceres Promoter construct YP0275 as found in
      Promoter Report #142
<220> FEATURE:
<221> NAME/KEY: misc_feature
<223> OTHER INFORMATION: T2 Seedling Expression: GFP expression observed
      in the seedling root, Epidermis, Root cap and Root hair of the
      root

<400> SEQUENCE: 105
aaacattaat atgtagtaac tatgggcgta tgctttactt tttaaaatgg gcctatgcta       60
taattgaatg acaaggatta aacaactaat aaaattgtag atgggttaag atgacttatt      120
tttttactta ccaatttata aatgggcttc gatgtactga aatatatcgc gcctattaac      180
gaggccattc aacgaatgtt ttaagggccc tatttcgaca ttttaaagaa cacctaggtc      240
atcattccag aaatggatat tataggtttt agataatttc ccacgtttgg tttatttatc      300
tattttttga cgttgaccaa cataatcgtg cccaaccgtt tcacgcaacg aatttatata      360
cgaaatatat atattttcca aattaagata ccacaatcaa aacagctgtt gattaacaaa      420 gagattttt ttttttggtt ttgagttaca ataacgttag aggataaggt ttcttgcaac       480
gattaggaaa tcgtataaaa taaaatatgt tataattaag tgttttattt tataatgagt      540
attaatataa ataaaacctg caaaggata gggatattga ataataaaga gaaacgaaag       600
agcaatttta cttctttata attgaaatta tgtgaatgtt atgtttacaa tgaatgattc      660
atcgttctat atattgaagt aaagaatgag tttattgtgc ttgcataatg acgttaactt      720
cacatataca cttattacat aacatttatc acatgtgcgt ctttttttt ttttactttg       780 taaaatttcc tcactttaa gactttata acaattacta gtaaaataaa gttgcttggg        840
gctacaccct ttctccctcc aacaactcta tttatagata acattatatc aaaatcaaaa      900
catagtccct ttcttctata aaggttttt cacaaccaaa tttccattat aaatcaaaaa       960
ataaaaactt aattagtttt tacagaagaa agaaaaca                              999

<210> SEQ ID NO 106
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0337 as found in
      Promoter Report #143
<220> FEATURE:
<221> NAME/KEY: misc_feature
<223> OTHER INFORMATION: T2 Seedling Expression: GFP expression observed
      in the Epidermis and Root hair of the seedling root

<400> SEQUENCE: 106 taatttttt atttttggaa ctaacactta ttagtttagg tttccatcac ctatttaatt        60
cgtaattctt atacatgcat ataatagaga tacatatata caaatttatg atcatttttg      120
cacaacatgt gatctcattc attagtatgc attatgcgaa aacctcgacg cgcaaaagac      180
acgtaatagc taataatgtt actcatttat aatgattgaa gcaagacgaa acaacaaca       240 tatatatcaa attgtaaact agatatttct taaaagtgaa aaaaaacaaa gaaatataaa      300
ggacaatttt gagtcagtct cttaatatta aaacatatat acataaataa gcacaaacgt      360
ggttacctgt cttcatgcaa tgtggacttt agttatctca atcaaaatca aaataaaagg      420
tgtaatagtt ctcgtcattt ttcaaatttt aaaaatcaga accaagtgat ttttgtttga      480
```

-continued

```
gtattgatcc attgtttaaa caatttaaca cagtatatac gtctcttgag atgttgacat      540
gatgataaaa tacgagatcg tctcttggtt ttcgaatttt gaactttaat agttttcttt      600
tttagggaaa ctttaatagt tgtttatcat aagattagtc acctaatggt tacgttgcag      660
taccgaacca atttttacc cttttttcta aatgtggtcg tggcataatt tccaaaagag       720
atccaaaacc cggtttgctc aactgataag ccggtcggtt ctggtttgaa aaacaagaaa      780
taatctgaaa gtgtgaaaca gcaacgtgtc tcggtgtttc atgagccacc tgccacctca      840
ttcacgtcgg tcattttgtc gtttcacggt tcacgctcta gacacgtgct ctgtccccac      900
catgactttc gctgccgact cgcttcgctt tgcaaactca aacatgtgtg tatatgtaag      960
tttcatccta ataagcatct cttaccacat taattaaaaa                            1000
```

<210> SEQ ID NO 107
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter construct YP0384 as found in
      Promoter Report #144
<220> FEATURE:
<221> NAME/KEY: misc_feature
<223> OTHER INFORMATION: T2 Seedling Expression: GFP expression observed
      in the seedling Root, the Epidermis of the root

<400> SEQUENCE: 107

```
tttaaaaaat tggataaaac accgataaaa attcacattt gcaaatttta ttcagtcgga       60
atatatattt gaaacaagtt ttgaaatcca ttggacgatt aaaattcatt gttgagagga      120
taaatatgga tttgttcatc tgaaccatgt cgttgattag tgattgacta ccatgaaaaa      180
tatgttatga aaagtataac aacttttgat aaatcacatt tattaacaat aaatcaagac      240
aaaatatgtc aacaataata gtagtagaag atattaattc aaattcatcc gtaacaacaa      300
aaaatcatac cacaattaag tgtacagaaa aaccttttgg atatatttat tgtcgctttt      360
caatgatttt cgtgaaaagg atatatttgt gtaaaataag aaggatcttg acgggtgtaa      420
aaacatgcac aattcttaat ttagaccaat cagaagacaa cacgaacact tctttattat      480
aagctattaa acaaaatctt gcctatttg cttagaataa tatgaagagt gactcatcag       540
ggagtggaaa atatctcagg atttgctttt agctctaaca tgtcaaacta tctagatgcc      600
aacaacacaa agtgcaaatt cttttaatat gaaaacaaca ataatatttc taatagaaaa      660
ttaaaagggg aaataaaata tttttttaaa atatacaaaa gaagaaggaa tccatcatca      720 aagtttata aaattgtaat ataatacaaa cttgtttgct tccttgtctc tccctctgtc       780
tctctcatct ctcctatctt ctccatatat acttcatctt cacacccaaa actccacaca      840
aaatatctct ccctctatct gcaaattttc caaagttgca tcctttcaat ttccactcct      900
ctctaatata attcacattt tcccactatt gctgattcat ttttttttgt gaattatttc      960
aaacccacat aaaaaaatct tgtttaaat ttaaaacca                              999
```

<210> SEQ ID NO 108
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct PT0535 as found in
      Promoter Report #145
<220> FEATURE:

<221> NAME/KEY: misc_feature
<223> OTHER INFORMATION: T1 Mature Plant Expression: GFP expression
     observed in the Stem of the inflorescence meristem, the Pedicel,
     the Cortex of the Pedicel the Epidermis and Guard cell of the stem
<220> FEATURE:
<221> NAME/KEY: misc_feature
<223> OTHER INFORMATION: T2 Seedling Expression: GFP expression observed
     in the root transition zone of the Hypocotyle,
     the Epidermis of the lower root

<400> SEQUENCE: 108

```
tatcattatt gtactgcctg tcaattttt gattgtatct tttattcagc agcatcacat      60
tctccttcag tgtccttctc ttcttttctt tttcttttct ttttctttcc tcattaaacc    120
catacaattc tacggtaaat attatggatt tgcatacaaa ctctctaatt gtttgtttgg    180
gtactataat atgggtccc tataatatgt gtagcttaac tttaagatag aactaagtca    240
acaagatccg gagacaccat gtcaaagttc tatgttctta tgattagatg aacaaagtta   300
tgatttattc aagattatca cgattcgaac tagttctaaa cttgtaaacg taaaataata   360
aataacgttt gcaactacaa cactgaacat aaattaatga gtttgcttg atgtgttggt   420 taaaatttgg aatgggacaa taaaaagaag aagagaactg agagaagtgg tgggggaagt   480 gggaaccta acttccccac gtgacactaa cgagcaacgt taattgaata gtagtaggcc    540 cttttttgtag tacactcttt tatatatggt caccttttaa ttagtttgca atcacatac    600 ttttaaaatc ataaaagcaa ttaacgttgc tcgttggtgt catatgcgat tgtagttagt   660
ataatcgatc ttaattaaaa caaagtccat attaaaaatg accaaagtat gtaaaaataa   720
aatgttgaat tagcatatgg tcactgatct tttctatttt aagatttagt aaacctaaga   780
tgtatccgca agcctatagg gtttgatgtg gattactact agttacttt gtatgggctt    840 gaagaaactt cattgggcca caagaggga ggagtgagcg aagagcccaa attcaaacaa    900
aaggatatga gggttcaaat gttattataa aatatattgt ggccaatttg taaagaaact   960
tgataattac tttaaaagcc ccaacacaat tatctttaca                         1000
```

<210> SEQ ID NO 109
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter construct YP0385 as found in
     Promoter Report #146
<220> FEATURE:
<221> NAME/KEY: misc_feature
<223> OTHER INFORMATION: T1 Mature Plant Expression: GFP expression
     observed in the Abscission zone between the Pedicel and Sepal, the
     Abscission zone in the flower
<220> FEATURE:
<221> NAME/KEY: misc_feature
<223> OTHER INFORMATION: T2 Seedling Expression: GFP expression observed
     in the Epidermis of the seedling root

<400> SEQUENCE: 109

```
actcaacaat aggacaagcc aaaaaaattc caattattgt gttactctat tcttctaaat    60
ttgaacacta atagactatg acatatgagt atataatgtg aagtcttaag atattttcat   120
gtgggagatg aataggccaa gttggagtct gcaaacaaga agctcttgag ccacgacata   180
agccaagttg atgaccgtaa ttaatgaaac taaatgtgtg tggttatata ttagggaccc    240
atggccatat acacaatttt tgtttctgtc gatagcatgc gtttatatat atttctaaaa   300
aaactaacat atttactgga tttgagttcg aatattgaca ctaatataaa ctacgtacca   360
```

```
aactacatat gtttatctat atttgattga tcgaagaatt ctgaactgtt ttagaaaatt    420
tcaatacact taacttcatc ttacaacggt aaaagaaatc accactagac aaacaatgcc    480
tcataatgtc tcgaaccctc aaactcaaga gtatacattt tactagatta gagaatttga    540
tatcctcaag ttgccaaaga attggaagct tttgttacca aacttagaaa cagaagaagc    600
cacaaaaaaa gacaaaggga gttaaagatt gaagtgatgc atttgtctaa gtgtgaaagg    660
tctcaagtct caactttgaa ccataataac attactcaca ctccctttt ttttcttttt    720 ttttcccaaa gtacccttt taattccctc tataacccac tcactccatt ccctctttct    780
gtcactgatt caacacgtgg ccacactgat gggatccacc tttcctctta cccacctccc    840
ggtttatata aaccctttcac aacacttcat cgctctcaaa ccaactctct cttctctctt    900
ctctcctctc ttctacaaga agaaaaaaaa cagagccttt acacatctca aaatcgaact    960
tactttaacc accaaatact gattgaacac acttgaaa                            998
```

<210> SEQ ID NO 110
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0371 as found in
      Promoter Report #147
<220> FEATURE:
<221> NAME/KEY: misc_feature
<223> OTHER INFORMATION: T1 Mature Plant Expression: GFP expression
      observed in the Guard cell of the flower
<220> FEATURE:
<221> NAME/KEY: misc_feature
<223> OTHER INFORMATION: T2 Seedling Expression: GFP expression observed
      in the Epidermis and Root hairs of the seedling root

<400> SEQUENCE: 110

```
gatatatttg tttaataatg cctacgattc tgcgaagaca ggagaagcca tacctttcaa      60
tctaagccgt caacttgttc ccttacgtgg gatcctatta tacaatccaa cggttctaaa     120
tgagccacgc cttccagatc taacacagtc atgccttcta cagtctgcac cccttttttt    180
tttagtgttt tatctacatt ttttcctttg tgtttaattt tgtgccaaca tctataactt     240
acccctataa aaatattcaa ttatcacaga atacccacaa tcgaaaacaa aatttaccgg     300
aataatttaa ttaaagctgg actataatga caattccgaa actatcaagg aataaattaa     360
agaaactaaa aaactaaagg gcattagagt aaagaagcgg caacatcaga attaaaaaac     420
tgccgaaaaa ccaacctagt agccgtttat atgacaacac gtacgcaaag tctcggtaat     480
gactcatcag ttttcatgtg caaacatatt accccccatga aataaaaaag cagagaagcg     540
atcaaaaaaa tcttcattaa aagaaccta aatctctcat atccgccgcc gtctttgcct     600
cattttcaac accggtgatg acgtgtaaat agatctggtt ttcacggttc tcactactct     660
ctgtgatttt tcagactatt gaatcgttag gaccaaaaca agtacaaaga aactgcagaa     720
gaaaagattt gagagagata tcttacgaaa caaggtatat atttctcttg ttaaatcttt     780
gaaaatactt tcaaagtttc ggttggattc tcgaataagt taggttaaat agtcaatata     840
gaattataga taaatcgata cctttgtttt gttatcattc aatttttatt gttgttacga     900
ttagtaacaa cgtttagat cttgatctat atattaataa tactaatact ttgtttttt     960 ttgtttttt ttaatacat attttgcttt tggaagatca                            1000
```

<210> SEQ ID NO 111
<211> LENGTH: 1000

```
<212> TYPE: DNA
<213> ORGANISM: Arabidopsis thaliana
<220> FEATURE:
<221> NAME/KEY: misc_feature
<223> OTHER INFORMATION: Ceres Promoter construct PT0610 as found in
      Promoter Report #148
<220> FEATURE:
<221> NAME/KEY: misc_feature
<223> OTHER INFORMATION: T1 Mature Plant Expression: GFP expression
      observed in the flower, the silique, the pre-fertilized silique,
      the fertilized silique, the leaf, the stem

<400> SEQUENCE: 111
ttagtgaaat tatgacatta agtaaggttt tcttagttag ctaatgtatg gctattcaat    60
tgttatgtta ggctatttta gttagtatat gaatttaggc agtctatgca aatgatttcg   120
ttttcatttt ttcatatgta aacatcaaga tcaagtaacg ccattcgagt tgatattttt   180
tttttaaatt agtgtgtgta aattttggac cgcttatttg agtttgctaa tgaagttgca   240
tatatattac gttaaaccat aggcaaacta atttgaaaca tccgattcga tttcctgtaa   300
tttttcttgg ttaattgacc aaaatcaaga tcttcagaaa taaaataaaa gacgaaagaa   360
agctgtcgca aagcagattg tgttaaaaaa aagtggattg ggctcaaacg caacttgtcc   420
agcccgtgac aattacccta tacgcaagta agagtaacgt atcactggca aaagttggta   480
ttagttacga tatctttgtc atgggggcat gcatgggcat ggcttaagag ttaagcctta   540
agaagagtcc cacactcgtg actctcatga tcacttgttg tttcttacgg gcaaatacat   600
ttaactttat tcttcattta ttcacctata ttcttttgga taataacttt tctctatata   660
aaataacaaa catcgtacgt ttcatttatt tacaacaagc gatgagaatt aaaaggagac   720
cttaattgat gatactcttc ttttctctcg gttacaacgg gattattaca gataatgata   780
atctatatgg atgctgacgt ggaaaaacaa aatttggtga aacacgtcaa ttaagcacga   840
cttttccatg gctagtggct aagatcgttt catcacatgg ctatatcata taatacttgg   900
atgaattcaa aataaacgac tgagaaaatg tccacgtcac ggcgcaccgc tttggactta   960
agtctcctat aataaataca acaccaaaca ttgcattcca                        1000

<210> SEQ ID NO 112
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct PT0590 as found in
      Promoter Report #152
<220> FEATURE:
<221> NAME/KEY: misc_feature
<223> OTHER INFORMATION: T1 Mature Plant Expression: GFP expression
      observed in the flower bud, pedicel and silique
<220> FEATURE:
<221> NAME/KEY: misc_feature
<223> OTHER INFORMATION: T2 Seedling Expression: GFP expression observed
      in the seedling, the root transition zone, the rosette leaf, the
      lateral root, the root, lateral root initiation

<400> SEQUENCE: 112
attattcaat ttaataaaaa ttgagtcggc caatttaatg cgagacttct gtacaacgac    60
cctaaaagtg ggtttgataa atgaaacata ttgcaacaaa aaaatactag taataatgat   120
aaaatagtaa catgtcatgg cgcattgaat atcctacgaa ggtttagtgt ttacttttaa   180
aaaatcctaa tatgatacta gtacatatag ctagcttgcc ttgcttatgc tattgcatag   240
tctgtattaa taaatgatgt tatacatttc gatagagtaa cattttggga acatgagtga   300
```

```
acgtgcttga atcttcgtgc ccttgacgtc agaagctagt aattttaaat actaattaac        360
attcatacaa attaacagat acaatgtact atatcataat tcgtttccgt aacacaacgc        420
aacaatttga aagtagatgt actttagtac ttagttagtg tgcaccaaaa aaaaaagatg        480
tagttagtta gtaaggggtt aaatgtttta atttattaag aaaacttaaa ttcattaaat        540
gttagaaaaa gtctaattag tttatattcg aacactgtgc tcaaaattaa aaagtcaact        600
attttagact atagagttta ttaattaata ataaattcga taaatcaccg tattattttc        660
ttcaacgaca agtagccgtg aagacacggg agcgaagaga gataaacaga agatgaagaa        720
gaagatcaat gtcataatct tcagggagat aaatccgtaa tctttattaa tcaaggttaa        780
tccttttttt tttcttcatc ttaattcttt gcgtcttcct tttctattta tcacgagatc        840
tgtctttctt tttcctcttc tttctctctc ttctctctga agacagtact tgtttctgtc        900
cggcgttaaa agcttcggtg gtggtctctt gacttctctg agaagaagaa aaggaagctg        960
agtctcattt tagattcagc tcacgaggaa gtgacgacga                             1000
```

<210> SEQ ID NO 113
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct PT0629 as found in
      Promoter Report #154
<220> FEATURE:
<221> NAME/KEY: misc_feature
<223> OTHER INFORMATION: T1 Mature Plant Expression: GFP expression
      observed in the Guard cells of the pedicel and leaf, the Root
      apical meristem and Suspensor of the late torpedo stage in the
      ovule, the Suspensor of the ovule
<220> FEATURE:
<221> NAME/KEY: misc_feature
<223> OTHER INFORMATION: T2 Seedling Expression: GFP expression observed
      in the Guard cells and Vasculature of the seedling, the
      Vasculature of the cotyledon and root, the root transition zone,
      the Root Cap of the root tip

<400> SEQUENCE: 113

```
tttaagcata tcaaatgtga aaattggtct taggttatga tgtatatcct tatatagtaa         60
aagtatatta gtctaaaaat ttagatttaa aaagtgaact aaaatttaaa agcaagctga        120
attacataaa tcaagtgaca attgtaattt gttgtgacat ttgtaagttc ataatggtac        180
gtgtcacgct atgttaatta agtttgaaat atgagatgta agaaaaaagt gatcaaaaat        240
taagttcttt tggagcgtta agtccaaagg tcaattagag cgcaatatca gtccagaaaa        300
gtggatgaaa aatgtccatc catccatcga gaaatatgct taaagtaaac gcttactttt        360
caagcgacct tcacggtatt gccgcagtca aaaatacgcg gcgactgttt ggttggtata        420
gtgacgaccc actctcacgc ggattcatta atttcctatc acaaataaga aaaagaaac        480 gtgaaattaa tttgttaagt aacaaaaaca aagaaaaag gaaactgaca agaaacgcta        540
aagtggttcc ttccttgtac tcaaaaaaac gttaatttac agctcagaat aagttttct        600 gtttaccgta atttcgaccc aatatttta cgaataacaa tttagtccaa aacctctttg        660
atatattgca atttaatacc ctaattaagt cttcttatct agtaatttgg ttttatttcc        720
atgacctaca atataagata atagtcatta gtgctagata taaagactga attagggtat        780
ataagatata tggaatgcta agattacaaa gagatagaga atcaaaaaaa ggaaagaatt        840
aaggggcaaa tatgaaataa ttaaaaacaa gggagccaaa ggaacaatgt aagaaaagca        900
ataaaattaa aaacaaaacc ctcaaaaaga agaaagcgga gactcgttag cttttttcctg       960
```

```
cctcctataa attgaacgcg acttgcagaa cctttcctca                    1000
```

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct PT0642 as found in
      Promoter Report #160
<220> FEATURE:
<221> NAME/KEY: misc_feature
<223> OTHER INFORMATION: T1 Mature Plant Expression: GFP expression
      observed in the Endosperm of the ovules at torpedo stage of the
      embryo and in mature ovules
<220> FEATURE:
<221> NAME/KEY: misc_feature
<223> OTHER INFORMATION: T2 Seedling Expression: GFP expression observed
      in the Epidermis of the seedling, hypocotyl, cotyledon and Root

<400> SEQUENCE: 114

```
ttgaacatcc ttaatttgaa ccataaaaaa tatgacatta actatctgat taattttcac      60
ttaagggatg gttagttaag ttacattgga ttaaaaatgg tattagtaga ccaattagaa     120
catgtatgcc attttttgtt tacaaaaacc tttttaagtg gtatttataa gacttgctca     180
atttcattca aaagaacatg aaatggatgg actagtttta atggcaataa cccacacaat     240
tactcatatt tggttcaaca aacttctatt tcggttcact tattaatttt ccatctatat     300
atgaatcata taatatgatt aatttacaca agttcacacg gccacgtaaa atgtaactgt     360
cttcaagttg tgcacataaa gagggtagtt tcgaagataa cgggtcaacg aaagggtaaa     420
agagtaaatt gcatagaacg cggccaaatt aaaagccccc aattgggata aaagtcatcg     480
ccgtctctta ggtgtcaaat ctcaactgtc taaaaacatt aaaagcttcg ttggggtagt     540
tgcatcttcc ctctctaata caaaacttat tttatccagt tttagtttcg attttttcatt    600
tgttaacatg ttttcatttt tcttttaatg ttaatagcct ttttatttgg aaaatgaaaa     660
caatttcaca atttaattct aaattaccat ttctaaaaaa tagaaataat ataaataata    720
atattgaata atacatggac taaaaaatta tagtactgtc ctaaacaaaa ttgcttgact    780
agattgaaca gaaatgtttt ttgatgtctt actagtttga acaatttatt tgctaacatt    840
attctctttg tatatttctt aaaaacccat atttttttcct taaatatttc ccatttcccc   900
taactacatt caatagctaa gtctctctct ccctctctct ttctctctca ctcaaaaatt    960
tcccattaaa ttctcaaatt ttctccaact ttttaggcca                          1000
```

<210> SEQ ID NO 115
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct PT0623 as found in
      Promoter Report #161
<220> FEATURE:
<221> NAME/KEY: misc_feature
<223> OTHER INFORMATION: T1 Mature Plant Expression: GFP expression
      observed in the inflorescence meristem, the inflorescence
      meristem, the flower, the stamen, the pre-fertilized silique, the
      unfertilized stigma, the pre-fertilized ovule, the fertilized
      ovule, the developing seed
<220> FEATURE:
<221> NAME/KEY: misc_feature
<223> OTHER INFORMATION: T1 Mature Plant Expression: GFP expression
      observed in the developing seed, the early mature seed, the Seed
      coat, the embryo, the Leaf, the stem <220> FEATURE:
<221> NAME/KEY: misc_feature
<223> OTHER INFORMATION: T2 Seedling Expression: GFP expression observed
      in the leaf, the seedling, the root tip

<400> SEQUENCE: 115

```
aaagttattg acattttgaa aggaccgtaa atattaccaa aaaactgacg gagttaggat      60
cggccacgta gaaagggaca agagagaaac agtcacggac tcggccagac taagtatggg     120
cctgtctgaa tccaaactca gctaagttcc aaaagcataa agagagatgt gtaatgaaat     180
gaacgtattc tagaaacgaa agcaatgtta tgctttgttt ttgagccaca tgttttttggg    240 agatggagag aatctttttt acgtttttaa cctaacccac ttggcacttg gccaaaaaag    300
tgagaagaaa ctgtggcgaa tgagtaggcc acgccatgga ctttgttcct tgtccttcaa    360
aagttaaatt tatgttatgc gtggggacaa tctaagcaac gtggttcctt taaatatcgc    420
agcttcctct tttacacttt tggagcctac gtgttttgtt ttggaccggc caaatacacg    480
agtcagtcag tttagaaata atttggatgt ccaaaaatct tggagatcca aataaaataa    540
ttagcatgtt ttagttcata agaatatgaa atgtagataa actgtctata ttaattttttc    600 catagaattg gctttttatc gaggtgatgt acttaatgac tttgttgatt actactcgta    660
taacaataaa gaatatgata ctatgtgaga cttataatga atttggtgtg tgttaattaa    720
tccagttgaa acagtttaat aacaaatcag aataaaaatt gtagtaagaa aatttgaacg    780
ctgatccttc aacctagata gtgaacctt caaatactat atgattcacg tgtaatgttt    840
ttgaccgttg gttattttg tgtgaactat attaacttat caatatcgaa aggctaaata     900
agtaaataac taaagaaag ttcaggaaac aactcgacct aatgacctat catttctgat    960
cacccgtcct ataaatacat acgtaagatc attcgttact                       1000
```

<210> SEQ ID NO 116
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct PT0613 as found in
      Promoter Report #163
<220> FEATURE:
<221> NAME/KEY: misc_feature
<223> OTHER INFORMATION: T1 Mature Plant Expression: GFP expression
      observed in the silique, the pollen, the embryo, the stem,
<220> FEATURE:
<221> NAME/KEY: misc_feature
<223> OTHER INFORMATION: T2 Seedling Expression: GFP expression observed
      in the Epidermis, Root hair, Cortex and Hypocotyl in the root tip

<400> SEQUENCE: 116

```
ttaatactaa cattgtagaa agccacaaaa aagaaattga aatgtgagta gatgctgagt      60
cagaggtttg gtcaatacac aacagctaat tgagataata ttatacacgt cacgatgact    120
tgttttttct cctcccaact tgttaatttc tttattctta aaattaaacc atcgcaaaaa    180
cagaagaaca cagctgtttt tctcgactcc caatttctat tttgctgcta aggacatttc    240
atttcattat ttcccaattc aggactcctt agattttcct aaatttgttt tcctaacttg    300
ctctctctca ttctaacatt ttctcatttt tttagattat cttgtacttt ttagtagatt    360
attttatcag gttttacaaa catacattga cattctaaaa agggcttcta aaaattcagt    420
gtggaatgct gatatactaa aaaaaggtca tgcaaaatta tctacgattt atctaaaatt    480
agataatttg ccatatataa ctattaacta ataatcgatc ctttgatttt ttgtttagat    540
```

```
aaaacgaaac agctatatct ttttttttg ttatcggatt ttaatcgaat aaaagctgaa      600
aaataacagt tatatcttct tctttttaa ctaatgaaac agttatatct aaacaaaca       660 acagaaacag taaatatta atgcaaatcc gcgtcaagag ataaatttta acaaactaat      720
aacaattgag ataagattag cgcaaaagaa actctaattt tagagcgtgt aaacacaaac    780
acgtcttgaa agtaaacgtg aattacacgc ttctaaaacg agcgtgagtt ttggttataa    840
cgaagatacg gtgaagtgtg acacctttct acgttaattt cagtttgagg acacaactca    900
agttatgttt gatatctaag gacttgcact gtctccaaat ctgcaggaag gactttttga    960
ttggatcaat ataaatacca tctccattct cgtctccttc                          1000

<210> SEQ ID NO 117
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter construct YP0093 as found in
      Promoter Report #261
<220> FEATURE:
<221> NAME/KEY: misc_feature
<223> OTHER INFORMATION: T1 Mature Plant Expression: GFP expression
      observed in Chalaza, Funiculus, Petals, Receptacle, Sepals,
      Silique, Stamen, Placenta, Micropyle
<220> FEATURE:
<221> NAME/KEY: misc_feature
<223> OTHER INFORMATION: T2 Seedling Expression: GFP expression observed
      in Cotyledons, Hypocotyl, Root Hair, Vascular bundle, Vascular

<400> SEQUENCE: 117
atgatgaaca ttctacatat ataattatta tgtttaagca cttagacagc ataaattctt     60
tctaattata taaatctaac cttgttacat tgtacatcta taaattactt gaagaaataa   120
cgagttctat ttcttttaa aaattaaaaa tactatacca tatctcagtg attaagttga    180
accaaaaggt acggaggaga aacaagcatt tgattcttcc ttatttatt ttattcatct    240 ctcactaatg atggtggaga aaaaagaaa ataccttaaca aacaaatata tattgtcata   300
caaaaatatt tctatatttt tagttaatta gtttatattc ctcactttc agggcttata    360 taagaaagtg agcaaacaca aatcaaaatg cagcagcaaa tactatcatc acccatctcc   420
ttagttctat tttataattc ctcttctttt tgttcatagc tttgtaatta tagtcttatt   480
tctctttaag gctcaataag aggaggtact attactacac ttctctctac tttacttgt    540 atttagcat taaaatccta aaatccgttt taaattcaaa ataaaactta gagatgttta    600
atctcgattc ggttttcgg ctttaggaga ataattatat gaaattagta tggatatctt    660
tactagtttc cattcaaatg attctgattt caatctaata ctctcactct ttaattaaac   720
tatatgtagt gtaatttcac actgttaaat ttctaccatg tcatgtatat tagagttgca   780
tagaaaattg taaacatcc atttgaattc gaatgaaaca aatgttttta aaataaaatt    840
ttggttttta aaagaaaaat ctaaaactga attatatcgt ttaaccaagt tgtaaaagtc   900
ataaaacgta gtatccttgta aatcgctctt ccacggtcca aatagacttc tagtaataaa   960
caagtaaaac taattttggt ttcttactaa ttttcacaga                        1000
```

What is claimed is:

1. An isolated nucleic acid molecule that modulates transcription, wherein the nucleic acid molecule is SEQ ID NO:6 or a fragment thereof having promoter activity.

2. The isolated nucleic acid molecule of claim 1, wherein said nucleic acid functions as a promoter.

3. The isolated nucleic acid molecule of claim 1, wherein said nucleic acid molecule modulates transcription during particular developmental times or in response to a stimuli or in a particular cell, tissue, or organ as set forth in the Sequence Listing-Miscellaneous Feature.

4. A vector construct comprising:
a) a first nucleic acid that modulates transcription wherein the nucleic acid molecule is SEQ ID NO:6 or a fragment thereof having promoter activity; and
b) a second nucleic acid having to be transcribed,
wherein said first and second nucleic acid molecules are heterologous to each other and are operably linked together.

5. A host cell comprising an isolated nucleic acid molecule according to claim 1, wherein said nucleic acid molecule is flanked by exogenous sequence.

6. A host cell comprising a vector construct of claim 4.

7. A method of modulating transcription by combining, in an environment suitable for transcription:
a) a first nucleic acid molecule that modulates transcription wherein the nucleic acid molecule is SEQ ID NO:6 or a fragment thereof having promoter activity; and
b) a second molecule to be transcribed;
wherein the first and second nucleic acid molecules are heterologous to each other and operably linked together.

8. The method according to claim 7, wherein said first nucleic acid molecule modulates transcription during the particular developmental times or in response to a stimuli or in a particular cell tissue, or organ as set forth in the Sequence Listing-Miscellaneous Feature wherein said first nucleic acid molecule is inserted into a plant cell and said plant cell is regenerated into a plant.

9. A plant comprising a vector construct according to claim 4.

* * * * *